United States Patent
Chen et al.

(10) Patent No.: US 7,612,212 B2
(45) Date of Patent: Nov. 3, 2009

(54) SUBSTITUTED HYDANTOINS

(75) Inventors: Shaoqing Chen, Bridgewater, NJ (US); Nicholas J. S. Huby, Scotch Plains, NJ (US); Norman Kong, West Caldwell, NJ (US); Steven Gregory Mischke, Florham Park, NJ (US); John Anthony Moliterni, Bloomfield, NJ (US); Hong Wang, Nutley, NJ (US); Zhuming Zhang, Hillsborough, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 367 days.

(21) Appl. No.: 11/657,800

(22) Filed: Jan. 25, 2007

(65) Prior Publication Data

US 2007/0197617 A1 Aug. 23, 2007

Related U.S. Application Data

(60) Provisional application No. 60/775,658, filed on Feb. 22, 2006, provisional application No. 60/861,105, filed on Nov. 27, 2006.

(51) Int. Cl.
   *C07D 233/02* (2006.01)
   *A61K 31/4166* (2006.01)
(52) U.S. Cl. ................... 548/317.1; 514/389
(58) Field of Classification Search .............. 548/317.1; 514/389
   See application file for complete search history.

(56) References Cited

FOREIGN PATENT DOCUMENTS

| WO | WO 99/01426 | 1/1999 |
|----|-------------|--------|
| WO | WO 99/05117 | 2/1999 |
| WO | WO-99/05117 | * 2/1999 |
| WO | WO 01/83478 | 11/2001 |
| WO | WO 2004/024715 | 3/2004 |
| WO | WO 2006/018188 | 2/2006 |
| WO | WO 2006/029862 | 3/2006 |

OTHER PUBLICATIONS

CAS Abstract 1931:37702, Locquin et al. Bulletin de la Societe Chimique de France (1931), vol. 49, pp. 595-600.*
CAS Abstract 1931:37701, Policard, Andrew. Bulletin de la Societe Chimique de France (1931), vol. 4, pp. 607-612.*
Hyun et al., J. Liq. Chrom. Rel. Technol., 25, pp. 573-588 (2002).
Böhme et al., J. Med. Chem., 23, pp. 405-412 (1980).
Salituro et al., J. Am. Chem. Soc., 112, pp. 760-770 (1990).
Shimizu et al., J. Chem. Soc. Chem. Commun., 867-868 (1986).
Chemical Abstract Service XP002428310.

* cited by examiner

*Primary Examiner*—Rei-Tsang Shiao
*Assistant Examiner*—Janet L Coppins
(74) *Attorney, Agent, or Firm*—George W. Johnston; Patricia S. Rocha-Tramaloni; David E. Wildman

(57) ABSTRACT

The present invention relates to compounds of the formula

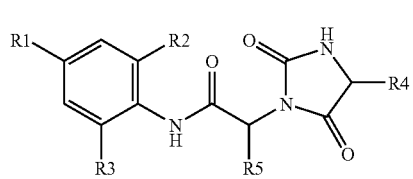

methods for the preparation thereof, and methods for their use. The compounds are useful in treating diseases characterized by the hyperactivity of MEK. Accordingly the compounds are useful in the treatment of diseases, such as cancer, cognitive and CNS disorders, and inflammatory/autoimmune diseases.

16 Claims, No Drawings

SUBSTITUTED HYDANTOINS

PRIORITY TO RELATED APPLICATIONS

This application claims the benefit of U.S. Provisional Application No. 60/775,658, filed Feb. 22, 2006 and U.S. Provisional Application No. 60/861,105, filed Nov. 27, 2006, which is hereby incorporated by reference in its entirety.

FIELD OF THE INVENTION

The present invention relates to hydantoin derivatives and their use as inhibitors of the two protein kinases commonly known as MEK1 and MEK2 for the treatment of human diseases such as cancer. MEK is a commonly used abbreviation for MAP kinase/ERK kinase which is in turn an abbreviation for mitogen activated protein/extracellular signal regulated kinase kinase. MEK is also sometimes referred to as MAPK kinase or MAP kinase kinase.

BACKGROUND OF THE INVENTION

Cancer is a disease characterized by the proliferation of malignant cells and tumors which have the potential for unlimited growth, local expansion and systemic metastasis. This uncontrolled growth is derived from abnormalities in the signal transduction pathways and the response to various growth factors, which differ from those found in normal cells. The abnormalities include changes in the intrinsic activity or in the cellular concentration of one or more signaling proteins in the signaling cascade. These changes are frequently caused by genetic mutations or overexpression of intracellular signaling proteins which can lead to spurious mitogenic signals within the cells.

The mitogen activated protein (MAP) kinase pathway represents one of the best characterized signaling pathways involved in the development and progression of human cancers. This pathway, via the Ras/Raf/MEK/ERK signal cascade, is responsible for transmitting and amplifying mitogenic signals from the cell surface to the nucleus where activated transcription factors regulate gene expression and determine cell fate. The constitutive activation of this pathway is sufficient to induce cellular transformation. Dysregulated activation of the MAP kinase pathway due to aberrant receptor tyrosine kinase activation, Ras mutations or Raf mutations has frequently been found in human cancers, and represents a major factor determining abnormal growth control. In human malignances, Ras mutations are common, having been identified in about 30% of cancers. The Ras family of GTPase proteins (proteins which convert guanosine triphosphate to guanosine diphosphate) relay signals from activated growth factor receptors to downstream intracellular partners. Prominent among the targets recruited by active membrane-bound Ras are the Raf family of serine/threonine protein kinases. The Raf family is composed of three related kinases (A-, B- and C-Raf) that act as downstream effectors of Ras. Ras-mediated Raf activation in turn triggers activation of MEK1 and MEK2 (MAP/ERK kinases 1 and 2) which in turn phosphorylate ERK1 and ERK2 (extracellular signal-regulated kinases 1 and 2) on both tyrosine-185 and threonine-183. Activated ERK1 and ERK2 translocate and accumulate in the nucleus, where they can phosphorylate a variety of substrates, including transcription factors that control cellular growth and survival. Given the importance of the Ras/Raf/MEK/ERK pathway in the development of human cancers, the kinase components of this signaling cascade are emerging as potentially important targets for the modulation of disease progression in cancer and other proliferative diseases.

MEK1 and MEK2 are members of a larger family of dual-specificity kinases (MEK1-7) that phosphorylate threonine and tyrosine residues of various MAP kinases. MEK1 and MEK2 are encoded by distinct genes, but they share high homology (80%) both within the C-terminal catalytic kinase domains and most of the N-terminal regulatory region. Oncogenic forms of MEK1 and MEK2 have not been found in human cancers, but constitutive activation of MEK has been shown to result in cellular transformation. In addition to Raf, MEK can also be activated by other oncogenes as well. So far, the only known substrates of MEK1 and MEK2 are ERK1 and ERK2. This unusual substrate specificity in addition to the unique ability to phosphorylate both tyrosine and threonine residues places MEK1 and MEK2 at a critical point in the signal transduction cascade which allows it to integrate many extracellular signals into the MAPK pathway.

Previously reported studies with the MEK inhibitor 2-(2-chloro-4-iodo-phenylamino)-N-cyclopropylmethoxy-3,4-difluoro-benzamide, also known as Cl-1040 (PCT publication No. WO 99/01426) provide further evidence that MEK1 and MEK2 represent an attractive target for pharmacological intervention in cancer or other human diseases characterized by the hyperactivity of MEK and diseases regulated by the MAPK pathway.

Substituted hydantoins have previously been reported as glucokinase activators (PCT publication No. WO 01/83478).

SUMMARY OF THE INVENTION

This invention relates to compounds of formula I:

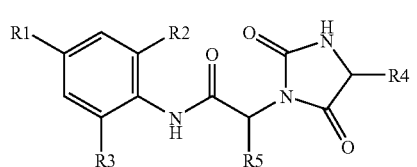

or pharmaceutically acceptable salts thereof, wherein R1, R2, R3, R4, R5, R6, R7, and R8 are described in this application. These compounds inhibit the enzymes MEK 1 and MEK2, protein kinases that are components of the MAP kinase signal transduction pathway and as such the compounds will have anti-hyperproliferative cellular activity.

DETAILED DESCRIPTION OF THE INVENTION

The present invention is directed to compounds of formula I:

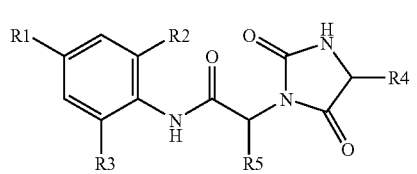

wherein:

R1 is selected from the group consisting of bromo, iodo, ethynyl, cycloalkyl, alkoxy, azetidinyl, acetyl, heterocycyl, cyano, straight-chained alkyl and branched-chain alkyl;

R2 is selected from the group consisting of hydrogen, chlorine, fluorine, and alkyl;

R3 is selected from the group consisting of hydrogen, chlorine, and fluorine;

R4 is selected from the group consisting of hydrogen, optionally substituted aryl, alkyl, and cycloalkyl;

R5 is selected from the group consisting of hydrogen and

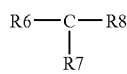

wherein R6 is selected from the group consisting of hydroxyl, alkoxy, cycloalkyl, optionally substituted alkyl, optionally substituted aryl, and optionally substituted heteroaryl;

R7 and R8 are independently selected from the group consisting of hydrogen and optionally substituted alkyl; or R6 and R7 can together form a cycloalkyl group and R8 is hydrogen;

and pharmaceutically acceptable salts or esters thereof.

In one aspect the invention is directed to compounds of formula I where R1 is iodo, ethynyl, or cyclopropyl.

In another aspect the invention is directed to compounds of formula I where R2 is hydrogen, chlorine, or fluorine.

In another aspect the invention is directed to compounds of formula I where R3 is hydrogen.

In another aspect the invention is directed to compounds of formula I where R8 is hydrogen or methyl.

In another aspect the invention is directed to compounds of formula I where R4 is substituted aryl.

In another aspect the invention is directed to compounds of formula I where R1 is iodo, ethynyl, or cyclopropyl, R2 is hydrogen, fluorine, chlorine, or methyl, R3 is hydrogen, R4 is optionally substituted aryl, R5 is

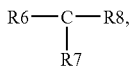

R6 is alkoxy, cycloalkyl, or optionally substituted aryl, R7 is hydrogen, and R8 is hydrogen or methyl.

In another aspect the invention is directed to compounds of formula I where R1 is iodo, ethynyl, or cyclopropyl, R2 is hydrogen, fluorine, or chlorine, R3 is hydrogen, R4 is optionally substituted phenyl, R5 is

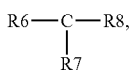

R6 is optionally substituted phenyl, R7 is hydrogen, and R8 is methyl.

In another aspect the invention is directed to compounds of formula 1 where R1 is iodo, R2 is fluorine or chlorine, R3 is hydrogen, R4 is phenyl substituted by alkoxy, R5 is

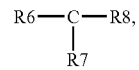

R6 is phenyl, R7 is hydrogen, and R8 is methyl.

In another aspect the invention is directed to compounds of formula 1 where R1 is iodo, R2 is fluorine or chlorine, R3 is hydrogen, R4 is phenyl substituted by 2,3-dihydroxy-propoxy or 2-hydroxy ethoxy, R5 is

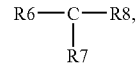

R6 is phenyl, R7 is hydrogen, and R8 is methyl.

Preferred compounds of the invention are:
(2S,3S)—N-(4-Bromo-phenyl)-2-[(R)-4-(4-methoxy-phenyl)-2,5-dioxo-imidazolidin-1-yl]-3-phenyl-butyramide;
(2S,3S)—N-(4-Iodo-phenyl)-2-[(R)-4-(4-methoxy-phenyl)-2,5-dioxo-imidazolidin-1-yl]-3-phenyl-butyramide;
(2S,3S)—N-(2-Fluoro-4-iodo-phenyl)-2-{(R)-4-[4-(2-hydroxy-ethoxy)-phenyl]-2,5-dioxo-imidazolidin-1-yl}-3-phenyl-butyramide;
(2S,3S)—N-(4-Ethynyl-2-fluoro-phenyl)-2-{(R)-4-[4-(2-hydroxy-ethoxy)-phenyl]-2,5-dioxo-imidazolidin-1-yl}-3-phenyl-butyramide;
(2R,3S)—N-(4-Ethynyl-2-fluoro-phenyl)-2-{(R)-4-[4-(2-hydroxy-ethoxy)-phenyl]-2,5-dioxo-imidazolidin-1-yl}-3-phenyl-butyramide;
(2S,3S)—N-(2-Chloro-4-iodo-phenyl)-2-{(R)-4-[4-(2-hydroxy-ethoxy)-phenyl]-2,5-dioxo-imidazolidin-1-yl}-3-phenyl-butyramide;
(2S,3S)-2-{(R)-4-[4-(2-Hydroxy-ethoxy)-phenyl]-2,5-dioxo-imidazolidin-1-yl}-N-(4-iodo-2-methyl-phenyl)-3-phenyl-butyramide;
(2S,3S)—N-(2-Chloro-4-iodo-phenyl)-2-{(R)-4-[4-((R)-2,3-dihydroxy-propoxy)-phenyl]-2,5-dioxo-imidazolidin-1-yl}-3-phenyl-butyramide;
(2S,3S)—N-(2-Chloro-4-iodo-phenyl)-2-{(R)-4-[4-((S)-2,3-dihydroxy-propoxy)-phenyl]-2,5-dioxo-imidazolidin-1-yl}-3-phenyl-butyramide;
(2S,3S)-2-{(R)-2,5-Dioxo-4-[4-(2-oxo-2-pyrrolidin-1-yl-ethoxy)-phenyl]-imidazolidin-1-yl}-N-(2-fluoro-4-iodo-phenyl)-3-phenyl-butyramide;
(2S,3S)-2-((R)-2,5-Dioxo-4-thiophen-3-yl-imidazolidin-1-yl)-N-(4-iodo-phenyl)-3-phenyl-butyramide;
(S)-2-[(R)-4-(2,3-Dihydro-benzo[1,4]dioxin-6-yl)-2,5-dioxo-imidazolidin-1-yl]-N-(2-fluoro-4-iodo-phenyl)-3-phenyl-propionamide;
(S)-2-[(R)-4-(4-Acetylamino-phenyl)-2,5-dioxo-imidazolidin-1-yl]-N-(2-fluoro-4-iodo-phenyl)-3-phenyl-propionamide;
(4-{(R)-1-[(1S,2S)-1-(2-Fluoro-4-iodo-phenylcarbamoyl)-2-phenyl-propyl]-2,5-dioxo-imidazolidin-4-yl}-phenoxymethyl)-phosphonic acid dimethyl ester;
(2S,3S)—N-(2-Fluoro-4-iodo-phenyl)-2-((R)-4-isopropyl-2,5-dioxo-imidazolidin-1-yl)-3-phenyl-butyramide;
(S)—N-(2-Fluoro-4-iodo-phenyl)-2-{(R)-4-[4-(2-hydroxy-ethoxy)-phenyl]-2,5-dioxo-imidazolidin-1-yl}-3-methyl-butyramide;

(S)—N-(2-Fluoro-4-iodo-phenyl)-2-[(R)-4-(4-methoxy-phenyl)-2,5-dioxo-imidazolidin-1-yl]-3-o-tolyl-propionamide;

(S)—N-(2-Fluoro-4-iodo-phenyl)-2-[(R)-4-(4-methoxy-phenyl)-2,5-dioxo-imidazolidin-1-yl]-3-m-tolyl-propionamide;

(S)—N-(2-Fluoro-4-iodo-phenyl)-2-[(R)-4-(4-methoxy-phenyl)-2,5-dioxo-imidazolidin-1-yl]-3-p-tolyl-propionamide; and (S)—N-(4-Cyclopropyl-2-fluoro-phenyl)-3-(4-fluoro-phenyl)-2-{(R)-4-[4-(2-hydroxy-1-hydroxymethyl-ethoxy)-phenyl]-2,5-dioxo-imidazolidin-1-yl}-propionamide.

"Alkyl" denotes a straight-chained, branched or cyclic saturated aliphatic hydrocarbon. Preferably, alkyl denotes a lower alkyl group i.e., a C1-C6 alkyl group and includes methyl, ethyl, propyl, isopropyl, butyl, t-butyl, 2-butyl, pentyl, hexyl, and the like. Generally, lower alkyl is preferably C1-C4 alkyl, and more preferably C1-C3 alkyl. Examples of cycloalkyl groups are moieties having 3 to 10, preferably 3 to 7 carbon atoms including cyclopropyl, cyclopentyl and cyclohexyl groups.

"Trihaloalkyl" means an alkyl group in which the three hydrogens of one of the terminal carbon atoms are replaced by halogen, e.g., trifluoromethyl, trichloromethyl, 1,1,1-trifluoroethyl, 1,1,1-trichloropropyl, and the like. "Trihalo lower alkyl" denotes a trihaloalkyl group with one to six carbon atoms, preferably one to three carbon atoms.

"Aryl" means a monovalent, monocyclic or bicyclic, aromatic carbocyclic or heterocyclic radical, preferably a 6-10 member aromatic ring system. Preferred aryl groups include, but are not limited to, phenyl, naphthyl, tolyl, xylyl, thienyl, furyl, indolyl, pyrrolyl, pyridinyl, oxy-pyridinyl, pyrazinyl, oxazolyl, thiaxolyl, quinolinyl, pyrimidinyl, imidazole and tetrazolyl. Aryl groups can be optionally mono-, di- or tri-substituted by, for example, lower alkyl, cycloalkyl, e.g., cyclopropyl, trihalo-lower alkyl, e.g., trifluoromethyl, hydroxyl, alkoxy, especially lower alkoxy, mono or dihydroxyl-substituted alkoxy, acetamido, methoxyacetamido, dimethylaminoacetamido, halogen, e.g., fluoro, chloro, or bromo, aniline derivatives, amide derivatives of the aniline derivatives and methanesulfonyl. When two or more substituents are present on an aryl or heteroaryl ring they may also be present in the form of a fused ring. Such fused rings include, but are not limited to, 3,4-methylenedioxyphenyl and 3,4-ethylenedioxyphenyl.

"Heteroatom" means an atom selected from N, O and S.

"Heterocyclyl" means a group having four to six carbon atoms and at least one heteroatom.

"Alkoxy or lower alkoxy" refers to any of the above lower alkyl groups attached to an oxygen atom. Typical lower alkoxy groups include methoxy, ethoxy, isopropoxy or propoxy, butyloxy, cyclopropyl methoxy, and the like. Further included within the meaning of alkoxy are multiple alkoxy side chains, e.g. ethoxy ethoxy, methoxy ethoxy, methoxy ethoxy ethoxy, methyl oxetanyl methoxy and the like. Also included are substituted alkoxy side chains, e.g., hydroxyethoxy, dihydroxypropoxy, dimethylamino ethoxy, diethylamino ethoxy, phosphoryl methoxy, dimethoxy-phosphoryl methoxy, carbamoyl methoxy, methyl and dimethyl carbamoyl methoxy, carbamoyl ethoxy, methyl and dimethyl carbamoyl ethoxy, azetidinyl carbamoyl ethoxy, oxopyrrolidinyl ethoxy, bishydroxyethylcarbamoyl methoxy, morpholinyl methoxy, morpholinyl ethoxy, piperazinyl methoxy, piperazinyl ethoxy, lower-alkyl piperazine ethoxy, oxo-pyrrolidinyl ethoxy, and the like.

"Pharmaceutically acceptable ester" refers to a conventionally esterified compound of formula I having a carboxyl group, which esters retain the biological effectiveness and properties of the compounds of formula I and are cleaved in vivo (in the organism) to the corresponding active carboxylic acid.

Information concerning esters and the use of esters for the delivery of pharmaceutical compounds is available in Design of Prodrugs. Bundgaard Hans ed. (Elsevier, 1985). See also, Ansel et. al., Pharmaceutical Dosage Forms and Drug Delivery Systems (6th Ed. 1995) at pp. 108-109; Krogsgaard-Larsen, et al., Textbook of Drug Design and Development (2d Ed. 1996) at pp. 152-191.

"Pharmaceutically acceptable salt" refers to conventional acid-addition salts or base-addition salts that retain the biological effectiveness and properties of the compounds of the present invention and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, trifluoro acetic acid and the like. Sample base-addition salts include those derived from ammonium, potassium, sodium and, quaternary ammonium hydroxides, such as for example, tetramethylammonium hydroxide. Chemical modification of a pharmaceutical compound (i.e. drug) into a salt is a technique well known to pharmaceutical chemists to obtain improved physical and chemical stability, hygroscopicity, flowability and solubility of compounds. See, e.g., Ansel et al., Pharmaceutical Dosage Forms and Drug Delivery Systems (6th Ed. 1995) at pp. 196 and 1456-1457.

"Pharmaceutically acceptable," such as pharmaceutically acceptable carrier, excipient, etc., means pharmacologically acceptable and substantially non-toxic to the subject to which the particular compound is administered.

"Substituted," as in substituted aryl or heteroaryl, means that the substitution can occur at one or more positions and, unless otherwise indicated, that the substituents at each substitution site are independently selected from the specified options.

"Therapeutically effective amount or effective amount" means an amount of at least one designated compound that significantly inhibits proliferation and/or prevents differentiation of a human tumor cell, including human tumor cell lines.

The compounds of the present invention are useful in the treatment or control of cell proliferative disorders such as inflammatory/autoimmune disorders, e.g., restenosis, cognative disorders, e.g., dementia and Alzeheimer's disease, CNS disorders, e.g., neuropathic pain and, in particular, oncological disorders. These compounds and formulations containing said compounds may be useful in the treatment or control of solid tumors, such as, for example, breast, colon, lung and prostate tumors.

The compounds of formula I as well as their salts have at least two asymmetric carbon atoms and therefore may be present as mixtures of different stereoisomers. The various isomers can be isolated by known separation methods, e.g., chromatography.

A therapeutically effective amount of a compound in accordance with this invention means an amount of compound that is effective to prevent, alleviate or ameliorate symptoms of disease or prolong the survival of the subject being treated. Determination of a therapeutically effective amount is within the skill in the art.

The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 10 mg to about 10,000 mg, preferably from about 200 mg to about 1,000 mg, should be appropriate, although the upper limit may be exceeded when indicated. The daily dosage can be administered as a single dose or in divided doses, or for parenteral administration, it may be given as one or more bolus injections or as a continuous infusion.

Pharmaceutical preparations useful in the practice of the invention, i.e., comprising the compounds of the invention can be administered internally, such as orally (e.g. in the form of tablets, coated tablets, dragées, hard and soft gelatin capsules, solutions, emulsions or suspensions), nasally (e.g. in the form of nasal sprays) or rectally (e.g. in the form of suppositories). However, the administration can also be effected parentally, such as intramuscularly or intravenously (e.g. in the form of injection solutions). Moreover, administration can be effected topically (e.g. in the form of ointments, creams or oils).

The compounds of formula (I) and their pharmaceutically acceptable salts and esters can be processed with pharmaceutically inert, inorganic or organic adjuvants for the production of tablets, coated tablets, dragées and hard gelatin capsules. Lactose, polyvinylpyrrolidone, hydroxypropylmethylcellulose, hydroxypropylcellulose, microcrystalline cellulose, corn starch or derivatives thereof, talc, stearic acid or its salts etc. can be used, for example, as such adjuvants for tablets, dragées and hard gelatin capsules.

Suitable adjuvants for soft gelatin capsules, are, for example, vegetable oils, waxes, fats, semi-solid substances and liquid polyols, etc. Suitable adjuvants for the production of solutions and syrups are, for example, water, polyols, saccharose, invert sugar, glucose, etc. Suitable adjuvants for injection solutions are, for example, water, alcohols, polyols, glycerol, vegetable oils, etc. Suitable adjuvants for suppositories are, for example, natural or hardened oils, waxes, fats, semi-solid or liquid polyols, etc. Suitable adjuvants for topical preparations are glycerides, semi-synthetic and synthetic glycerides, hydrogenated oils, liquid waxes, liquid paraffins, liquid fatty alcohols, sterols, polyethylene glycols and cellulose derivatives.

Moreover, the pharmaceutical preparations can contain preservatives, solubilizers, viscosity-increasing substances, stabilizers, wetting agents, emulsifiers, sweeteners, colorants, flavors, salts for varying the osmotic pressure, buffers, masking agents or antioxidants. They can also contain other therapeutic substances.

Reaction Schemes

The compounds claimed in the present invention (compounds of general formula 1) can be prepared using the general reaction sequence set out in Scheme 1.

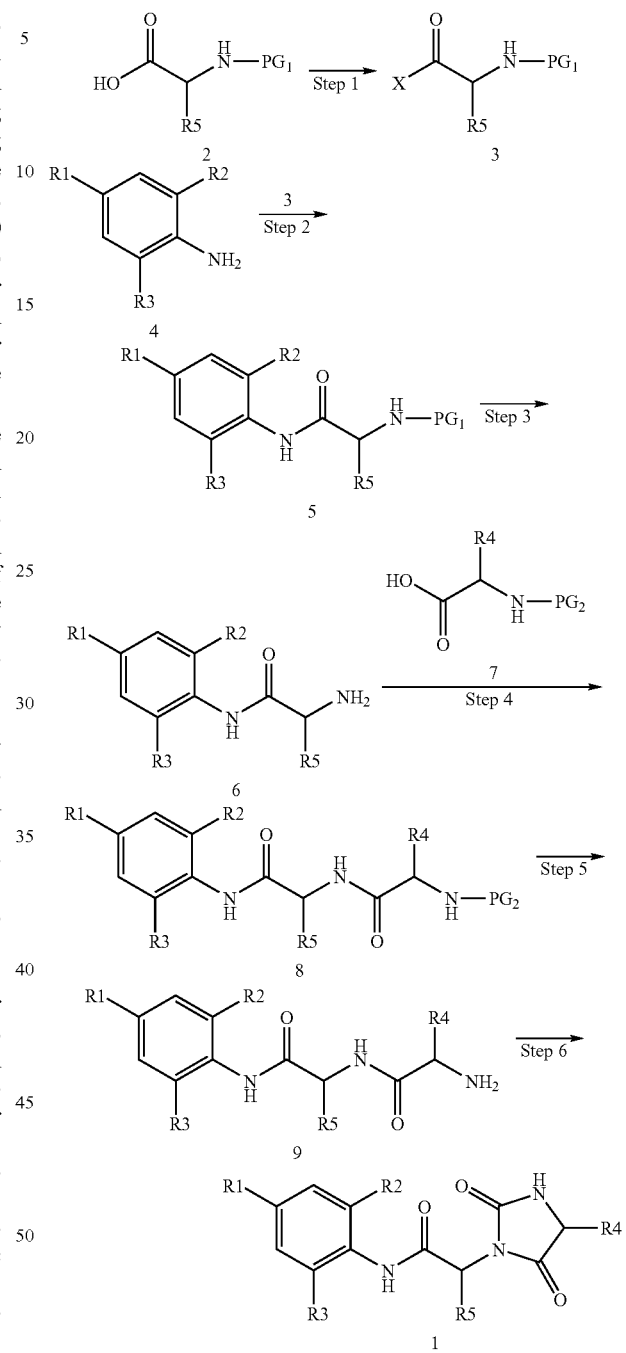

Step 1: A compound containing an α-amino acid functional group of general formula 2 is converted in to a reactive acylating species of general formula 3 which is suitable for use in step 2 of the synthetic sequence. Step 1 is most conveniently performed on an α-amino acid which bears a protecting group (PG1) on the α-amine nitrogen. A suitable choice for protecting group PG1 is one which renders the α-amine nitrogen inert to the reaction conditions employed during steps 1 and 2 of the synthetic sequence but which may be removed during step 3 of the synthetic sequence without causing undesired modifications to the rest of the compound when exposed to the conditions required for the removal of the protecting group. Preferred choices for protecting group PG1 may be made by reference to organic chemistry text books (e.g. Protective Groups in Organic Synthesis, Theodora W. Greene et al.), the original chemistry literature, or would be generally known to one knowledgeable in the art of organic synthesis. In particular carbamate-based protecting groups, e.g. tert-butyloxycarbonyl and 9H-fluoren-9-ylmethoxycarbonyl, are preferred but other amine-protecting groups may also be effective.

The choice of which reactive acylating agent of general formula 3 to form is dependent upon both compatibility with potentially reactive functional groups present elsewhere in compounds of general formula 3 and the reactivity and selectivity of the acylating agent of general formula 3 for acylation of the aniline derivative of general formula 4. This reaction yields the desired amide bond present in compounds of general formula 5. Typical reactive acylating agents which may be employed in step 2 are acyl halides (3, X=halogen) and acid anhydrides (3, X=O—C(O)R). Preferred choices for the acylating agents of general formula 3 are the acyl halides, in particular acyl fluorides (3, X=fluorine), acyl chlorides (3, X=chlorine) and acyl bromides (3, X=bromine). Additional choices for acylating agents of general formula 3 may also be suitable for use in step 2 and would be apparent to one knowledgeable in the art of organic synthesis.

In the case where compounds of general formula 2 contain a chiral center at the α-carbon, the preferred stereochemistry is S.

Step 2: An aniline derivative of general formula 4 is combined with a pre-formed acylating agent of general formula 3 to form amide derivatives of general formula 5.

It will be apparent to one skilled in the art of organic synthesis that by use of known peptide coupling reaction techniques it may be possible to prepare compounds of general formula 5 directly from compounds of general formula 2 and general formula 4 without having to pre-form a reactive acylating agent of general formula 3. Typical peptide coupling reagents which may be employed for the direct conversion of compounds of general formula 2 and general formula 4 to compounds of general formula 5 include diimide based reagents e.g. dicyclohexylcarbodiimide, (3-dimethylamino-propyl)-ethyl-carbod iim ide hydrochloride; or uronium based reagents, e.g. O-benzotriazol-1-yl-N,N,N',N'-tetramethyluronium hexaflurorophosphate or O-benzotriazol-1-yl-N,N,N',N'-bis(tetramethylene)uronium hexaflurorophosphate. Alternative peptide coupling reagents may also effective in performing this conversion. Selection of alternative peptide coupling reagents may be made by reference to the original chemistry literature or would be generally known to one knowledgeable in the art of organic synthesis.

Step 3: This step in the synthetic sequence entails the removal of protecting group PG1 from compounds of general formula 5 to form amine-containing compounds of general formula 6 in preparation for subsequent elaboration. As mentioned above the choice of protecting group PG1 and conditions used during step 3 for removal of PG1 is influenced by what other potentially reactive functional groups are present in compounds of general formula 5 and the requirement of avoiding undesired reactions elsewhere in the starting material or product of the reaction, i.e., compounds of general formulae 5 and 6, respectively. In the case where the amine-protecting group PG1 present in compounds of general formula 5 is tert-butyloxycarbonyl, the protecting group can be removed under acidic conditions such as trifluoroacetic acid in dichloromethane or hydrochloric acid in p-dioxane. Removal of the tert-butyloxycarbonyl group under acidic conditions initially liberates the corresponding salt of the compound of general formula 6, from which the free amine of general formula 6 can be liberated after treatment with base. In the case where the amine-protecting group PG1 present in compounds of general formula 5 is 9H-fluoren-9-ylmethoxycarbonyl, the protecting group can be removed under basic conditions such as piperidine in dichloromethane.

Step 4: Compounds of general formula 8 are obtained by combining amines of general formula 6 with a compound containing an α-amino acid functional grouping. Step 4 is most conveniently performed on compounds of general formula 7 which contain an α-amino acid which bears a protecting group (PG2) on the α-amine nitrogen. The criteria for choice of the protecting group PG2 are the same as described for the choice of protecting group PG1 in step 1. In particular carbamate-based protecting groups, e.g. tert-butyloxycarbonyl, are preferred but other amine-protecting groups may also be effective.

In the case where compounds of general formula 7 contain a chiral center at the α-carbon, the preferred stereochemistry is R.

Step 5: This step in the synthetic sequence entails the removal of protecting group PG2 from compounds of general formula 8 to form amine-containing compounds of general formula 9 prior to completion of the synthetic sequence. The choice of conditions for effecting removal of protecting group PG2 from compounds of general formula 8 is based both upon the chemical reactivity of protecting group PG2 and the nature and reactivity of other functional groups present in the starting material and product of the reaction performed in step 5, i.e., compounds of general formula 8 and 9, respectively. In the case where the amine-protecting group PG2 present in compounds of general formula 8 is tert-butyloxycarbonyl, the protecting group can be removed under acidic conditions such as trifluoroacetic acid in dichloromethane, hydrochloric acid in p-dioxane or in neat formic acid. Removal of the tert-butyloxycarbonyl group under acidic conditions initially liberates the corresponding salt of the compound of general formula 9, from which the free amine of general formula 9 can be liberated after treatment with base.

Step 6: Compounds of general formula 1 as are claimed in the present invention can be obtained from compounds of general formula 9 by cyclization in the presence of phosgene or an equivalent reagent, i.e. a carbonyl group directly attached to two displaceable groups. A preferred reagent for effecting the cyclization of compounds of general formula 9 to compounds of general formula 1 is trichloromethyl chloroformate which functions in the reaction mixture as two equivalents of phosgene. Cyclization of compounds of general formula 9 with trichloromethyl chloroformate is generally rapid and is typically performed at low temperature (<0° C.) and in the presence of a carefully controlled amount of base to neutralize acid formed during the cyclization but to avoid unnecessary isomerization of the potentially labile chiral center on the newly formed hydantoin ring.

It will be apparent to one knowledgeable in the art of organic synthesis that when one or more of the substituents labeled R1 through R5, or substituents included in their definitions, in the compounds shown in Scheme 1 are in and of themselves chemically reactive groups, or contains chemically reactive groups, then additional modification of the compounds of general formula 1 through 9 which contain those reactive groups may be possible. The point in the synthetic sequence at which modification of the chemically reactive groups takes place may be chosen such that the newly elaborated group is chemically inert to the reagents to be employed during the remaining steps of the synthetic sequence and does not interfere with the remaining steps in the synthetic sequence shown in Scheme 1. Alternatively, if the newly elaborated group is not chemically inert or can interfere with the remaining steps in the synthetic sequence it may be necessary to temporarily mask the reactive functional group with an appropriate protecting group or to derivatize the functional group into a moiety which is stable to the remaining transformations in the synthetic sequence and will be present in the final product of the reaction sequence. If a protecting group is introduced which is not required in the final compound of general structure 1 then it may either be removed under the conditions remaining in the synthetic sequence shown in Scheme 1 or by introduction of an additional deprotection step into the synthetic sequence depending upon the nature of the protecting group employed.

The reaction conditions for the above reactions can vary to a certain extent.

Methods to perform the above described reactions and processes would be apparent to those of ordinary skill in the art based on the present disclosure, or can be deduced in analogy from the examples. Starting materials are commercially available or can be made by methods analogous to those described in the Examples.

The following examples shall illustrate preferred embodiments of the present invention but are not intended to limit the scope of the invention.

EXAMPLE 1

(2S,3S)—N-(4-Bromo-phenyl)-2-[(R)-4-(4-methoxy-phenyl)-2,5-dioxo-imidazolidin-1-yl]-3-phenyl-butyramide

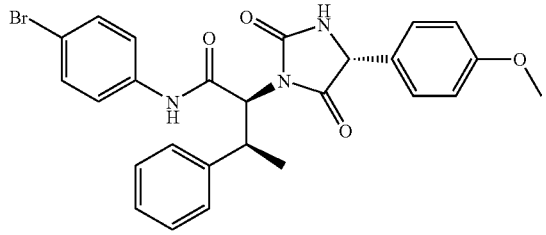

Step 1: To a solution of (2S,3S)-2-tert-butoxycarbonylamino-3-phenyl-butyric acid (838 mg, 3.0 mmol) in dichloromethane (10 mL) at −35° C. was added dry pyridine (255 μL, 3.15 mmol) and cyanuric fluoride (375 μL, 4.5 mmol) under an atmosphere of dry argon. The mixture was stirred for 1.5 hours while maintaining the temperature between −35 and −25° C. A small amount of ice was added to the reaction mixture and the mixture stirred vigorously for 15 minutes. The organic layer was decanted away from the aqueous solution and the aqueous layer extracted with dichloromethane (2×10 mL). The combined organic layers were washed with ice cold water (15 mL), dried over sodium sulfate, filtered and concentrated in vacuo to give (1-fluorocarbonyl-2-phenyl-propyl)-carbamic acid tert-butyl ester which was used in the subsequent step without further purification.

Step 2: To a solution of 4-bromoaniline (97% purity) (177 mg, 1.0 mmol) and N-methyl morpholine (220 μL, 2.0 mmol) in dry tetrahydrofuran (3 mL) was added a solution of (1-fluorocarbonyl-2-phenyl-propyl)-carbamic acid tert-butyl ester (≈1.5 mmol) in dry tetrahydrofuran (2 mL+1 mL to rinse addition funnel in to reaction mixture) and a catalytic amount of dimethyl-pyridin-4-yl-amine. The mixture was heated to reflux under an atmosphere of dry argon for 3 hours and then cooled to ambient temperature. The reaction mixture was concentrated in vacuo and the residue taken up in ethyl acetate. The organic solution was washed sequentially with water (once), 1.5 M aqueous potassium hydrogen sulfate solution (once), water (three times), brine (once), dried over sodium sulfate, filtered and concentrated in vacuo to give (1S,2S)-1-(4-bromo-phenylcarbamoyl)-2-phenyl-propyl]-carbamic acid tert-butyl ester which was used in the subsequent step without further purification (530 mg).

LC-MS: Obs Mass (M+H$^+$), 433/435; Calcd. Mass, 433/435 for $C_{21}H_{26}BrN_2O^+$.

Step 3: To a solution of (1S,2S)-1-(4-bromo-phenylcarbamoyl)-2-phenyl-propyl]-carbamic acid tert-butyl ester (530 mg, ≈1 mmol) in dichloromethane (12 mL) at 0° C. under an atmosphere of dry argon was added trifluoroacetic acid (8 mL, 108 mmol) and the mixture stirred at 0° C. for 1.5 hours. The reaction mixture was concentrated in vacuo and the residue suspended in ice cold water. The aqueous suspension was neutralized with saturated aqueous sodium hydrogen carbonate solution (12 mL) then extracted with dichloromethane (three times). The combined organic extracts were dried over sodium sulfate, filtered and concentrated in vacuo to give (2S,3S)-2-amino-N-(4-bromo-phenyl)-3-phenyl-butyramide which was used in the subsequent step without further purification (334 mg).

LC-MS: Obs Mass (M+H$^+$)=333/335; Calcd. Mass, 333/335 for $C_{16}H_{18}BrN_2O^+$.

Step 4: To a solution of (2S,3S)-2-amino-N-(4-bromo-phenyl)-3-phenyl-butyramide (167 mg, ≈0.5 mol) in N,N-dimethylformamide (3 mL) at 0° C. was added (R)-tert-butyloxycarbonylamino-4-methoxyphenylglycine (155 mg, 0.55 mmol) (prepared according to the procedure of Hyun, M. H., et al., J. Liq. Chrom. & Rel. Technol. 2002, 25, 573-588), N,N-diisopropylethylamine (350 μL, 2.0 mmol), N-hydroxybenzotriazole (82 mg, 0.6 mmol), O-benzotriazol-1-yl-N,N,N',N'-tetramethyluronium hexafluorophosphate (227 mg, 0.6 mmol) and a catalytic amount of dimethyl-pyridin-4-yl-amine and the mixture stirred under an atmosphere of dry argon and allowed to slowly warm to ambient temperature overnight. The reaction mixture was poured into ice/water (20 mL), extracted with ethyl acetate (2×10 mL), the combined organic extracts washed with water (3×10 mL), brine (10 mL), dried over sodium sulfate, filtered and concentrated in vacuo. The crude product was purified by chromatography over silica gel eluted with 2:1 v/v hexanes/ethyl acetate to give [[(1S,2S)-1-(4-bromo-phenylcarbamoyl)-2-phenyl-propylcarbamoyl]-((R)-4-methoxy-phenyl)-methyl]-carbamic acid tert-butyl ester as a colorless solid (154 mg, 52%).

LC-MS: Obs Mass (M−H$^-$), 594/596; Calcd. Mass, 594/596 for $C_{30}H_{33}BrN_3O_5^-$.

Step 5: To a solution of [[(1S,2S)-1-(4-bromo-phenylcarbamoyl)-2-phenyl-propylcarbamoyl]-((R)-4-methoxy-phenyl)-methyl]-carbamic acid tert-butyl ester (150 mg, 0.25 mmol) in dichloromethane (10 mL) at 0° C. under an atmosphere of dry argon was added trifluoroacetic acid (6 mL, 81 mmol) and the mixture stirred at 0° C. for 1.5 hours. The reaction mixture was concentrated in vacuo and the residue suspended in ice cold water. The aqueous suspension was neutralized with saturated aqueous sodium hydrogen carbonate solution (12 mL) then extracted with dichloromethane (three times). The combined organic extracts were dried over sodium sulfate, filtered and concentrated in vacuo to give (2S,3S)-2-[(R)-2-amino-2-(4-methoxy-phenyl)-acetylamino]-N-(4-bromo-phenyl)-3-phenyl-butyramide which was used in the subsequent step without further purification (124 mg).

LC-MS: Obs Mass (M+H$^+$), 496/498; Calcd. Mass, 496/498 for $C_{25}H_{26}BrN_3O_3^+$.

Step 6: To a solution of diphosgene (20 μL, 0.17 mmol) in 1:1 v/v toluene/tetrahydrofuran (16 mL total) at −35° C. under an atmosphere of dry argon was added a solution of (2S,3S)-2-[(R)-2-amino-2-(4-methoxy-phenyl)-acetylamino]-N-(4-bromo-phenyl)-3-phenyl-butyramide (120 mg, 0.24 mmol) and N,N-diisopropylethylamine (210 μL, 1.2 mmol) in tetrahydrofuran (8 mL) dropwise with stirring over 10 minutes. After an additional 45 minutes ice was added and the reaction mixture stirred vigorously and warmed to ambient temperature. The reaction mixture was poured into water, extracted with ethyl acetate (twice) and the combined organic layers were washed sequentially with water (twice), 0.1 M aqueous hydrochloric acid, water, saturated aqueous sodium hydrogen carbonate, water and brine, then dried over sodium sulfate, filtered and concentrated in vacuo. The crude product was purified by chromatography over silica gel eluted with 2:1 v/v hexanes/ethyl acetate. The isolated product was dissolved in a small volume of dichloromethane and then precipitated by dropwise addition to a vigorously stirred large volume of petroleum ether. The precipitated solid was isolated by filtration and dried in vacuo to give (2S,3S)—N-(4-bromo-phenyl)-2-[(R)-4-(4-methoxy-phenyl)-2,5-dioxo-imidazolidin-1-yl]-3-phenyl-butyramide as a colorless solid (87 mg, 69%).

HRMS: Obs. Mass (M+H$^+$), 522.1021. Calcd. Mass, 522.1023 for $_{26}H_{25}BrN_3O_4^+$.

EXAMPLE 2

(2S,3S)—N-(4-Bromo-2-fluoro-phenyl)-2-{(R)-4-[4-((R)-2,3-dihydroxy-propoxy)-phenyl]-2,5-dioxo-imidazolidin-1-yl}-3-phenyl-butyramide

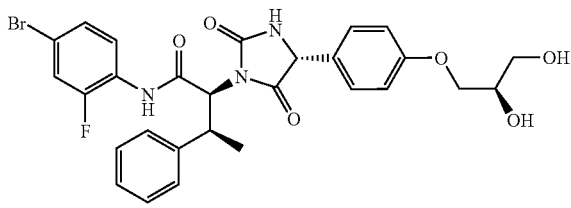

Prepared by the same method as described in example 1 except that (i) 4-bromo-2-fluoroaniline was used in place of 4-bromoaniline in step 2, and (ii) (R)-tert-butoxycarbonylamino-[4-((S)-2,2-dimethyl-[1,3]dioxolan-4-ylmethoxy)-phenyl]-acetic acid was used in place of (R)-tert-butyloxycarbonylamino-4-methoxyphenylglycine in step 4. (R)-tert-Butoxycarbonylamino-[4-((S)-2,2-dimethyl-[1,3]dioxolan-4-ylmethoxy)-phenyl]-acetic acid was prepared and used as described in example 114.

HRMS: Obs Mass (M+H$^+$), 600.1137. Calcd. Mass, 600.1140 for $C_{28}H_{28}BrFN_3O_6^-$.

EXAMPLE 3

(2S,3S)—N-(4-Bromo-2-chloro-phenyl)-2-{(R)-4-[4-(2-hydroxy-ethoxy)-phenyl]-2,5-dioxo-imidazolidin-1-yl}-3-phenyl-butyramide

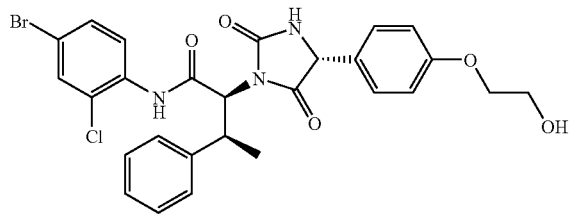

Step 1: 4-Bromo-2-chloro-aniline (325 mg, 1.58 mmol) and (S,S)-2-tert-butoxycarbonylamino-3-phenyl-butyric acid (440 mg, 1.58 mmol) in pyridine (5 mL) were cooled to −30° C. Phosporus oxychloride (0.158 mL, 1.7 mmol) was added and stirred at −20° C. for 2 hours. The mixture was poured into ice water and extracted with ethyl acetate (3×). The combined organic extracts were washed with water, brine, dried over sodium sulfate and concentrated in vacuo. The residue was dissolved in dichloromethane (5 mL) at 0° C. and trifluoroacetic acid (3 mol) added. Stirring was continued for 2 hours at 0° C. The mixture was evaporated and the residue dissolved in ether. The ether solution was basified with saturated aqueous sodium bicarbonate and extracted with ether. The organic extracts were washed with brine, dried over sodium sulfate and evaporated to give (2S,3S)-2-amino-N-(4-bromo-2-chloro-phenyl)-3-phenyl-butyramide (325 mg, 55%).

Step 2: To a solution of (2S,3S)-2-amino-N-(4-bromo-2-chloro-phenyl)-3-phenyl-butyramide (320 mg, 0.87 mmol) in N,N-dimethylformamide (3 mL) at 0° C. was added (R)-tert-butoxycarbonylamino-[4-(2-tert-butoxy-ethoxy)-phenyl]-acetic acid (320 mg, 0.87 mmol) (prepared as described in example 48 for the preparation of (R)-tert-butoxycarbonylamino-{4-[2-(tetrahydro-pyran-2-yloxy)-ethoxy]-phenyl}-acetic acid except that 2-(2-bromo-ethoxy)-2-methyl-propane was used in place of 2-(2-bromo-ethoxy)-tetrahydropyran), N,N-diisopropylethylamine (0.71 mL, 2.0 mmol), N-hydroxybenzotriazole (82 mg, 0.6 mmol), O-benzotriazol-1-yl-N,N,N',N'-tetramethyluronium hexafluorophosphate (227 mg, 0.6 mmol). After 30 minutes, the reaction mixture was poured into ice/water (20 mL), extracted with ethyl acetate (2×10 mL), the combined organic extracts washed with water (3×10 mL), brine (10 mL), dried over sodium sulfate, filtered and concentrated in vacuo to give [[(1S,2S)-1-(4-bromo-2-chloro-phenylcarbamoyl)-2-phenyl-butylcarbamoyl]-((R)-4-(tert-butoxy-ethoxy)-phenyl)-methyl]-carbamic acid tert-butyl ester as a white solid (560 mg). The ester was suspended in acetonitrile (5 mL) in a ice bath. 4 M hydrogen chloride in p-dioxane (2 mL) was added and the mixture stirred for 1.5 hours. The mixture was evaporated and triturated with ether/hexanes. The solid was filtered and partitioned between saturated aqueous sodium bicarbonate and dichloromethane. The organic layer was separated and washed with brine and dried over sodium sulfate. Evaporation of the solvents gave [[(1S,2S)-1-(4-bromo-2-chloro-phenylcarbamoyl)-2-phenyl-butylcarbamoyl]-((R)-4-(tert-butoxy-ethoxy)-phenyl)-methyl]-carbamic acid as a white solid (346 mg, 72%).

Step 3: [[(1S,2S)-1-(4-Bromo-2-chloro-phenylcarbamoyl)-2-phenyl-butylcarbamoyl]-((R)-4-(tert-butoxy-ethox(-phenyl)-methyl]-carbamic acid (344 mg, 0.56 mmol) and diisopropyl ethyl amine (0.40 mL, 2.25 mmol) were added to diphosgene (47 μL, 0.39 mmol) in tetrahydrofuran (5 mL) and toluene (5 mL) at −78° C. The mixture was stirred and warmed slowly from −78 to −30° C. over 1.5 hours and then diluted with ethyl acetate and washed with water. The organic layer was washed with brine, dried over sodium sulfate and evaporated. The residue was triturated with hexanes to give N-(4-bromo-2-chloro-phenyl)-2-{4-[4-(2-tert-butoxy-ethoxy)-phenyl]-2,5-dioxo-imidazolidin-1-yl}-3-phenyl-butyramide (300 mg, 84%).

Step 4: N-(4-Bromo-2-chloro-phenyl)-2-{4-[4-(2-tert-butoxy-ethoxy)-phenyl]-2,5-dioxo-imidazolidin-1-yl}-3-phenyl-butyramide (300 mg) was dissolved in dichloromethane (2 mL) and acetonitrile (2 mL) in an ice bath. Trimethylsilyl chloride (0.36 mL, 2.8 mmol) was added followed by sodium iodide (352 mg, 2.35 mmol). The mixture was stirred at 0° C. for 1.5 hours and then diluted with ethyl acetate. The mixture was washed with aqueous sodium bisulfite, washed with brine, dried over sodium sulfate and concentrated in vacuo. Trituration of the residue with hexanes gave N-(4-bromo-2-chloro-phenyl)-2-{4-[4-(2-hydroxy-ethoxy)-phenyl]-2,5-dioxo-imidazolidin-1-yl}-3-phenyl-butyramide (210 mg, 76%).

HRMS: Obs Mass (M+H$^+$), 586.0739. Calcd. Mass, 586.0739 for $C_{27}H_{26}BrClN_3O_5^+$.

EXAMPLE 4

(S)—N-(4-Iodo-phenyl)-2-[(R)-4-(4-methoxy-phenyl)-2,5-dioxo-imidazolidin-1-yl]-3-phenyl-propionamide

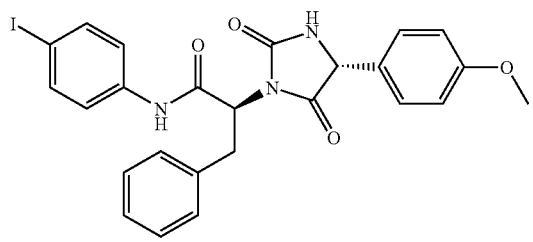

Prepared by the same method as described in example 1 except that (i) (S)-2-tert-butoxycarbonylamino-3-phenyl-propionic acid was used in place of (2S,3S)-2-tert-butoxycarbonylamino-3-phenyl-butyric acid in step 1, (ii) 4-iodoaniline was used in place of 4-bromoaniline in step 2, and (iii) the trifluoroacetic acid salt of (S)-2-amino-N-(4-iodo-phenyl)-3-phenyl-propionamide was isolated in step 3 and used directly in step 4 with 1.0 equivalent of triethylamine and (3-dimethylamino-propyl)-ethyl-carbodiimide hydrochloride as the coupling reagent in place of O-benzotriazol-1-yl-N,N,N',N'-tetramethyluronium hexaflurorophosphate.

HRMS: Obs Mass (M+H$^+$), 556.0726. Calcd. Mass, 556.0728 for $C_{25}H_{23}IN_3O_4^+$.

EXAMPLE 5

(2S,3S)—N-(4-Iodo-phenyl)-2-[(R)-4-(4-methoxy-phenyl)-2,5-dioxo-imidazolidin-1-yl]-3-phenyl-butyramide

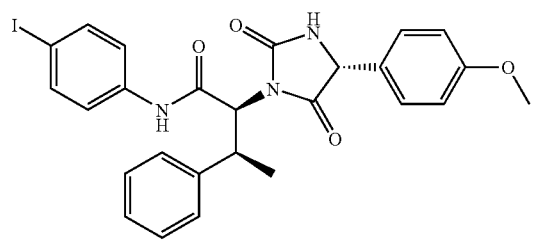

Prepared by the same method as described in example 1 except that 4-iodoaniline was used in place of 4-bromoaniline in step 2 and (3-dimethylamino-propyl)-ethyl-carbodiimide hydrochloride was used as the coupling reagent in place of O-benzotriazol-1-yl-N,N,N',N'-tetramethyluronium hexaflurorophosphate in step 4.

HRMS: Obs. Mass (M+H$^+$), 570.0883. Calcd. Mass, 570.0884 for $C_{26}H_{25}IN_3O_4^+$.

EXAMPLE 6

(2S,3S)-2-{(R)-4-[4-(2-Hydroxy-ethoxy)-phenyl]-2,5-dioxo-imidazolidin-1-yl}-N-(4-iodo-phenyl)-3-phenyl-butyramide

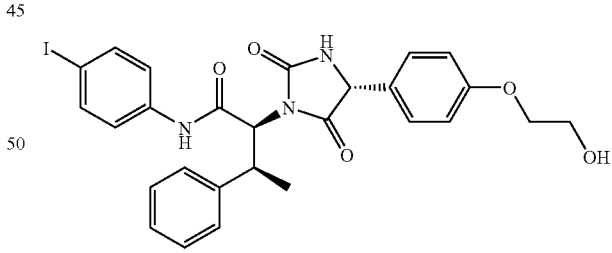

Prepared by the same method as described in example 48 except that (i) 4-iodoaniline was used in place of 2-fluoro-4-iodoaniline in step 2, and (ii) (3-dimethylamino-propyl)-ethyl-carbodiimide hydrochloride was used as the coupling reagent in place of O-benzotriazol-1-yl-N,N,N',N'-tetramethyluronium hexaflurorophosphate in step 4.

HRMS: Obs Mass (M+H$^+$), 600.0987 Calcd. Mass, 600.0990 for $C_{27}H_{27}IN_3O_5^+$.

EXAMPLE 7

(2S,3S)-2-{(R)-4-[4-(2-Ethoxy-ethoxy)-phenyl]-2,5-dioxo-imidazolidin-1-yl}-N-(4-iodo-phenyl)-3-phenyl-butyramide

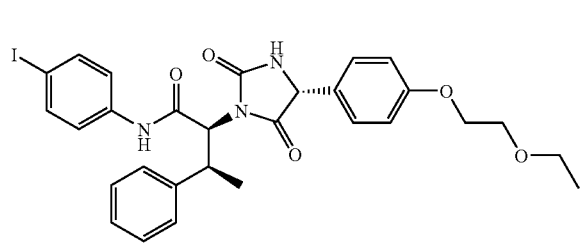

Prepared by the same method as described in example 1 except that (i) 4-iodoaniline was used in place of 4-bromoaniline in step 2 and (ii) (R)-tert-butoxycarbonylamino-{4-ethoxy-ethoxy]-phenyl}-acetic acid was used in place of (R)-tert-butyloxycarbonylamino-4-methoxyphenylglycine in step 4. (R)-tert-Butoxycarbonylamino-{4-ethoxy-ethoxy]-phenyl}-acetic acid was prepared as described in example 48 except that 1-bromo-2-ethoxy-ethane was used in place of 2-(2-bromo-ethoxy)-tetrahydropyran.

HRMS: Obs Mass (M+H$^+$), 628.1305. Calcd. Mass, 628.1303 for $C_{29}H_{31}IN_3O_5^+$.

EXAMPLE 8

(2S,3S)—N-(4-Iodo-phenyl)-2-((R)-4-{4-[2-(2-methoxy-ethoxy)-ethoxy]-phenyl}-2,5-dioxo-imidazolidin-1-yl)-3-phenyl-butyramide

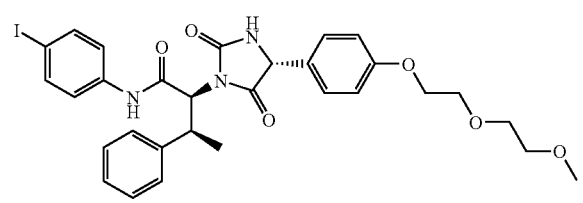

Prepared by the same method as described in example 7 except that (R)-tert-butoxycarbonylamino-{4-[2-(2-methoxy-ethoxy)-ethoxy]-phenyl}-acetic acid was used in place of (R)-tert-butoxycarbonylamino-{4-ethoxy-ethoxy]-phenyl}-acetic acid. (R)-tert-Butoxycarbonylamino-{4-[2-(2-methoxy-ethoxy)-ethoxy]-phenyl}-acetic acid was prepared as described in example 48 except that 1-(2-bromo-ethoxy)-2-methoxy-ethane was used in place of 2-(2-bromo-ethoxy)-tetrahydropyran.

HRMS: Obs Mass (M+H$^+$), 658.1410. Calcd. Mass, 658.1409 for $C_{30}H_{33}IN_3O_6^+$.

EXAMPLE 9

(2S,3S)—N-(4-Iodo-phenyl)-2-[(R)-4-(4-methylcarbamoylmethoxy-phenyl)-2,5-dioxo-imidazolidin-1-yl]-3-phenyl-butyramide

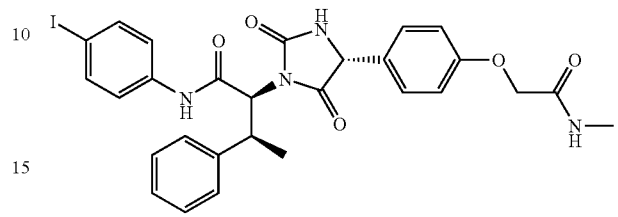

Prepared by the same method as described in example 5 except that (R)-tert-butoxycarbonylamino-(4-methylcarbamoylmethoxy-phenyl)-acetic acid was used in place of (R)-tert-butyloxycarbonylamino-4-methoxyphenylglycine in step 4. (R)-tert-Butoxycarbonylamino-(4-methylcarbamoylmethoxy-phenyl)-acetic acid was prepared by a method similar to that used for the preparation of (R)-tert-butyloxycarbonylamino-4-methoxyphenylglycine in example 1 except that 2-chloro-N-methyl-acetamide was used in place of iodomethane.

HRMS: Obs Mass (M+H$^+$), 627.1096. Calcd. Mass, 627.1099 for $C_{28}H_{28}IN_4O_5^+$.

EXAMPLE 10

(2S,3S)-2-{(R)-4-[4-(2-Azetidin-1-yl-2-oxo-ethoxy)-phenyl]-2,5-dioxo-imidazolidin-1-yl}-N-(4-iodo-phenyl)-3-phenyl-butyramide

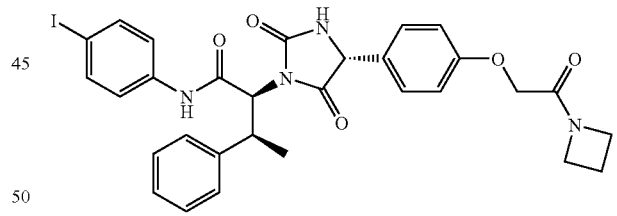

Prepared by the same method as described in example 1 except that (i) 4-iodoaniline was used in place of 4-bromoaniline in step 2 and (ii) (R)-[4-(2-azetidin-1-yl-2-oxo-ethoxy)-phenyl]-tert-butoxycarbonylamino-acetic acid was used in place of (R)-tert-butyloxycarbonylamino-4-methoxyphenylglycine. (R)-[4-(2-Azetidin-1-yl-2-oxo-ethoxy)-phenyl]-tert-butoxycarbonylamino-acetic acid was prepared by a method similar to that used for the preparation of (R)-tert-butyloxycarbonylamino-4-methoxyphenylglycine in example 1 except that 1-azetidin-1-yl-2-chloro-ethanone was used in place of iodomethane.

HRMS: Obs Mass (M+H$^+$), 653.1258. Calcd. Mass, 658.1256 for $C_{30}H_{30}IN_4O_5^+$.

EXAMPLE 11

(2S,3S)—N-(4-Iodo-phenyl)-2-{(R)-4-[4-(2-morpholin-4-yl-2-oxo-ethoxy)-phenyl]-2,5-dioxo-imidazolidin-1-yl}-3-phenyl-butyramide

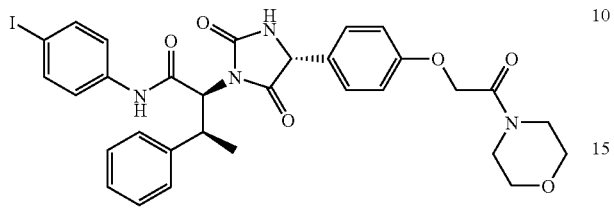

Prepared by the same method as described in example 1 except that (i) 4-iodoaniline was used in place of 4-bromoaniline in step 2 and (ii) (R)-tert-butoxycarbonylamino [4-(2-morpholin-4-yl-2-oxo-ethoxy)-phenyl]-acetic acid was used in place of (R)-tert-butyloxycarbonylamino-4-methoxyphenylglycine. (R)-tert-Butoxycarbonylamino[4-(2-morpholin-4-yl-2-oxo-ethoxy)-phenyl]-acetic acid was prepared by a method similar to that used for the preparation of (R)-tert-butyloxycarbonylamino-4-methoxyphenylglycine in example 1 except that 2-chloro-1-morpholin-4-yl-ethanone was used in place of iodomethane.

HRMS: Obs Mass (M+H$^+$), 683.1363. Calcd. Mass, 683.1361 for $C_{31}H_{32}IN_4O_6^+$.

EXAMPLE 12

(2S,3S)-2-[4-(3-Fluoro-4-methoxy-phenyl)-2,5-dioxo-imidazolidin-1-yl]-N-(4-iodo-phenyl)-3-phenyl-butyramide, isomer 1

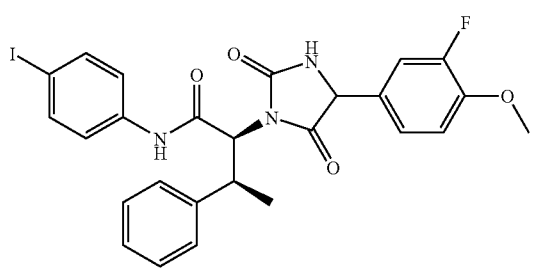

Prepared by the same method as described in example 1 except that (i) 4-iodoaniline was used in place of 4-bromoaniline in step 2, (ii) tert-butoxycarbonylamino-[3-fluoro-4-methoxy-phenyl]-acetic acid was used in place of (R)-tert-butyloxycarbonylamino-4-methoxyphenylglycine in step 4, and (iii) after step 5 the 2 diastereomers were separated by chromatography using silica gradient eluted between 0.2 and 1.5% v/v methanol in dichloromethane. The fractions containing the second eluted component were collected and taken forward in to step 6. tert-Butoxycarbonylamino-[3-fluoro-4-methoxy-phenyl]-acetic acid was prepared as described in WO 2006/029862.

HRMS: Obs Mass (M+H$^+$), 588.0790. Calcd. Mass, 588.0790 for $C_{26}H_{24}FIN_3O_4^+$.

EXAMPLE 13

(2S,3S)-2-[4-(3-Fluoro-4-methoxy-phenyl)-2,5-dioxo-imidazolidin-1-yl]-N-(4-iodo-phenyl)-3-phenyl-butyramide, isomer 2

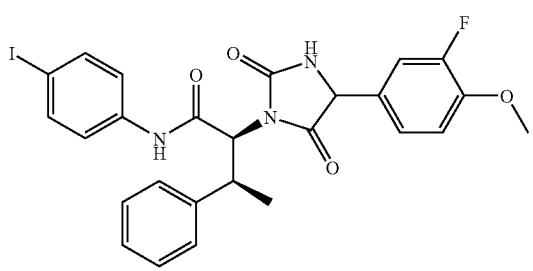

Prepared by the same method as described in example 12 except that during the chromatographic separation of the diastereomers after step 5 the first eluted component was collected and taken forward in to step 6.

HRMS: Obs Mass (M+H$^+$), 588.0785. Calcd. Mass, 588.0790 for $C_{26}H_{24}FIN_3O_4^+$.

EXAMPLE 14

(2S,3S)-2-((R)-2,5-Dioxo-4-thiophen-3-yl-imidazolidin-1-yl)-N-(4-iodo-phenyl)-3-phenyl-butyramide

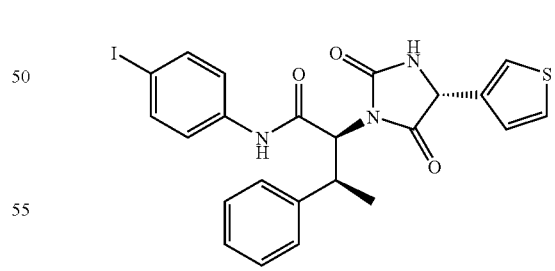

Prepared by the same method as described in example 5 except that (R)-tert-butoxycarbonylamino-thiophen-3-yl-acetic acid was used in place of (R)-tert-butyloxycarbonylamino-4-methoxyphenylglycine.

HRMS: Obs. Mass (M+H$^+$), 546.0339. Calcd. Mass, 546.0343 for $C_{23}H_{21}IN_3O_3S^+$.

EXAMPLE 15

(S)-2-(2,5-Dioxo-imidazolidin-1-yl)-N-(2-fluoro-4-iodo-phenyl)-3-p-tolyl-propionamide

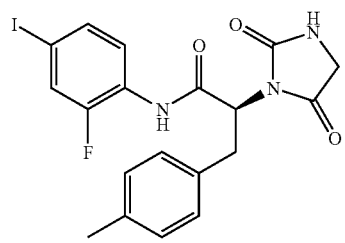

Prepared by the same method as described in example 1 except that (i) (S)-2-tert-butoxycarbonylamino-3-p-tolyl-propionic acid was used in place of (2S,3S)-2-tert-butoxycarbonylamino-3-phenyl-butyric acid in step 1, (ii) 2-fluoro-4-iodoaniline was used in place of 4-bromoaniline in step 2, and (iii) tert-butyloxycarbonylamino-glycine was used in place of (R)-tert-butyloxycarbonylamino-4-methoxyphenylglycine in step 4.

HRMS: Obs Mass (M+H$^+$), 482.0372. Calcd. Mass, 482.0372 for $C_{19}H_{18}FIN_3O_3^+$.

EXAMPLE 16

(S)-2-(2,5-Dioxo-imidazolidin-1-yl)-N-(2-fluoro-4-iodo-phenyl)-3-(4-fluoro-phenyl)-propionamide

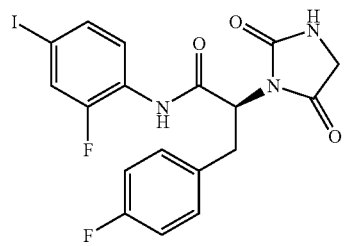

Prepared by the same method as described in example 1 except that (i) (S)-2-tert-butoxycarbonylamino-3-(4-fluoro-phenyl)-propionic acid was used in place of (2S,3S)-2-tert-butoxycarbonylamino-3-phenyl-butyric acid in step 1, (ii) 2-fluoro-4-iodoaniline was used in place of 4-bromoaniline in step 2, and (iii) tert-butyloxycarbonylamino-glycine was used in place of (R)-tert-butyloxycarbonylamino-4-methoxyphenylglycine in step 4.

HRMS: Obs Mass (M+H$^+$), 486.0116. Calcd. Mass, 486.0121 for $C_{18}H_{15}F_2IN_3O_3^+$.

EXAMPLE 17

(S)-2-(2,5-Dioxo-imidazolidin-1-yl)-N-(2-fluoro-4-iodo-phenyl)-3-o-tolyl-propionamide

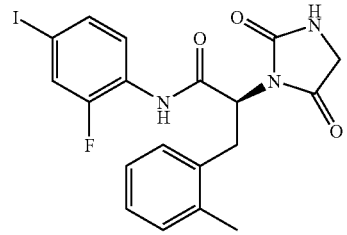

Prepared by the same method as described in example 1 except that (i) (S)-2-tert-butoxycarbonylamino-3-o-tolyl-propionic acid was used in place of (2S,3S)-2-tert-butoxycarbonylamino-3-phenyl-butyric acid in step 1, (ii) 2-fluoro-4-iodoaniline was used in place of 4-bromoaniline in step 2, and (iii) tert-butyloxycarbonylamino-glycine was used in place of (R)-tert-butyloxycarbonylamino-4-methoxyphenylglycine in step 4.

HRMS: Obs Mass (M+Na$^+$), 504.0190. Calcd. Mass, 504.0191 for $C_{19}H_{17}FIN_3NaO_3^+$.

EXAMPLE 18

(S)—N-(2-Fluoro-4-iodo-phenyl)-2-[(R)-4-(4-methoxy-phenyl)-2,5-dioxo-imidazolidin-1-yl]-3-phenyl-propionamide

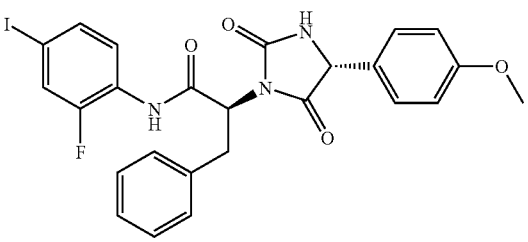

Prepared by the same method as described in example 4 except that 2-fluoro-4-iodoaniline was used in place of 4-iodoaniline in step 2.

HRMS: Obs Mass (M+H$^+$), 574.0629. Calcd. Mass, 574.0634 for $C_{25}H_{22}FIN_3O_4^+$.

EXAMPLE 19

(S)-2-[(R)-4-(4-Ethoxy-phenyl)-2,5-dioxo-imidazolidin-1-yl]-N-(2-fluoro-4-iodo-phenyl)-3-phenyl-propionamide

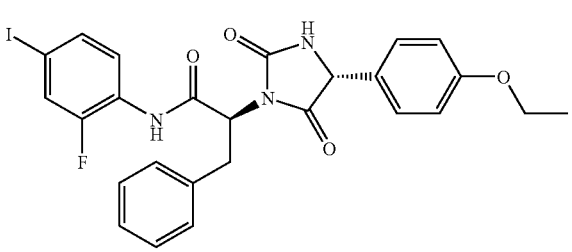

Prepared by the same method as described in example 1 except that (i) (S)-2-tert-butoxycarbonylamino-3-phenyl-propionic acid was used in place of (2S,3S)-2-tert-butoxycarbonylamino-3-phenyl-butyric acid in step 1, (ii) 2-fluoro-4-iodoaniline was used in place of 4-bromoaniline in step 2, and (iii) (R)-tert-butyloxycarbonylamino-4-ethyoxyphenylglycine was used in place of (R)-tert-butyloxycarbonylamino-4-methoxyphenylglycine in step 4. (R)-tert-Butyloxycarbonylamino-4-ethyoxyphenylglycine was prepared as described in example 48 except that ethyl iodide was used in place of 2-(2-bromo-ethoxy)-tetrahydropyran.

HRMS: Obs Mass (M+Na$^+$), 610.0605. Calcd. Mass, 610.0609 for $C_{26}H_{23}FIN_3NaO_4{}^+$.

EXAMPLE 20

(S)—N-(2-Fluoro-4-iodo-phenyl)-2-{(R)-4-[4-(2-hydroxy-ethoxy)-phenyl]-2,5-dioxo-imidazolidin-1-yl}-3-phenyl-propionamide

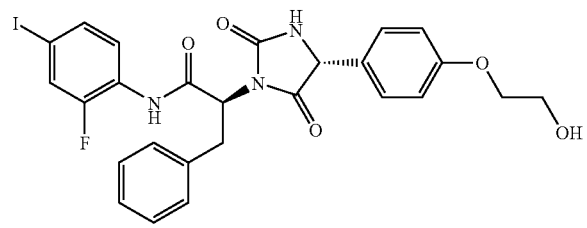

Prepared by the same method as described in example 18 except that (R)-tert-butoxycarbonylamino-{4-[2-(tetrahydro-pyran-2-yloxy)-ethoxy]-phenyl}-acetic acid was used in place of (R)-tert-butyloxycarbonylamino-4-methoxyphenylglycine in step 4.

HRMS: Obs Mass (M+H$^+$), 604.0738. Calcd. Mass, 604.0739 for $C_{26}H_{24}FIN_3O_5{}^+$.

EXAMPLE 21

(S)—N-(2-Fluoro-4-iodo-phenyl)-2-{(R)-4-[4-(2-methoxy-ethoxy)-phenyl]-2,5-dioxo-imidazolidin-1-yl}-3-phenyl-propionamide

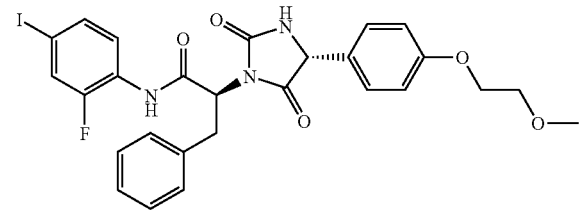

Prepared in a similar way as described in example 1 except that (i) (S)-2-tert-butoxycarbonylamino-3-phenyl-propionic acid was used in place of (2S,3S)-2-tert-butoxycarbonylamino-3-phenyl-butyric acid in step 1, (ii) 2-fluoro-4-iodoaniline was used in place of 4-bromoaniline in step 2, and (iii) (R)-tert-butoxycarbonylamino-[4-(methoxy-ethoxy)-phenyl]-acetic acid was used in place of (R)-tert-butoxycarbonylamino-[4-methoxy-phenyl]-acetic acid in step 4. (R)-tert-Butoxycarbonylamino-[4-(methoxy-ethoxy)-phenyl]-acetic acid was prepared as described in example 80.

HRMS: Obs Mass (M+H$^+$), 618.0896. Calcd. Mass, 618.0896 for $C_{27}H_{26}FIN_3O_5{}^+$.

EXAMPLE 22

(S)-2-{(R)-4-[4-(2-Ethoxy-ethoxy)-phenyl]-2,5-dioxo-imidazolidin-1-yl}-N-(2-fluoro-4-iodo-phenyl)-3-phenyl-propionamide

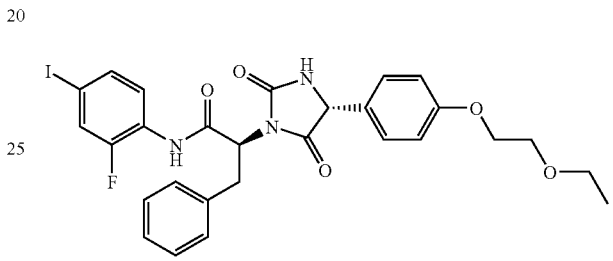

Prepared by the same method as described in example 18 except that (R)-tert-butoxycarbonylamino-[4-(2-ethoxy-ethoxy)-phenyl]-acetic acid was used in place of (R)-tert-butyloxycarbonylamino-4-methoxyphenylglycine in step 4.

HRMS: Obs Mass (M+Na$^+$), 654.0874. Calcd. Mass, 654.0871 for $C_{28}H_{27}FIN_3NaO_5{}^+$.

EXAMPLE 23

(S)—N-(2-Fluoro-4-iodo-phenyl)-2-((R)-4-{4-[2-(2-hydroxy-ethoxy)-ethoxy]-phenyl}-2,5-dioxo-imidazolidin-1-yl)-3-phenyl-propionamide

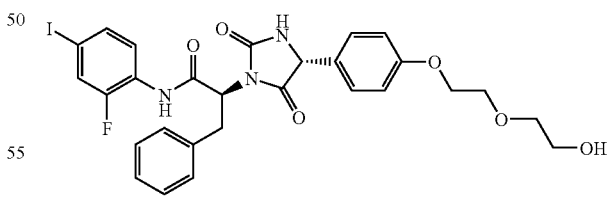

Prepared by the same method as described in example 18 except that (R)-tert-butoxycarbonylamino-(4-{2-[2-(tetrahydro-pyran-2-yloxy)-ethoxy]-ethoxy}-phenyl)-acetic acid was used in place of (R)-tert-butyloxycarbonylamino-4-methoxyphenylglycine in step 4.

HRMS: Obs Mass (M+Na$^+$), 670.0819. Calcd. Mass, 670.0821 for $C_{28}H_{27}FIN_3NaO_6{}^+$.

EXAMPLE 24

(S)—N-(2-Fluoro-4-iodo-phenyl)-2-((R)-4-{4-[2-(2-methoxy-ethoxy)-ethoxy]-phenyl}-2,5-dioxo-imidazolidin-1-yl)-3-phenyl-propionamide

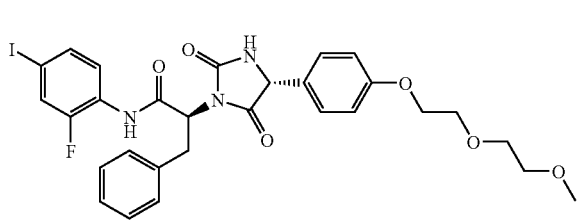

Prepared by the same method as described in example 1 except that (i) (S)-2-tert-butoxycarbonylamino-3-phenyl-propionic acid was used in place of (2S,3S)-2-tert-butoxycarbonylamino-3-phenyl-butyric acid in step 1, (ii) 2-fluoro-4-iodoaniline was used in place of 4-bromoaniline in step 2, and (iii) (R)-tert-butoxycarbonylamino-[4-(methoxy-ethoxy-ethoxy)-phenyl]-acetic acid was used in place of (R)-tert-butoxycarbonylamino-[4-methoxy-phenyl]-acetic acid in step 4. (R)-tert-Butoxycarbonylamino-[4-(methoxy-ethoxy-ethoxy)-phenyl]-acetic acid was prepared as described in example 48 except that 1-(2-bromo-ethoxy)-2-methoxy-ethane was used in place of 2-(2-bromo-ethoxy)-tetrahydro-pyran.

LC-MS: Obs Mass (M+H$^+$), 662.13. Calcd. Mass, 662.12 for $C_{29}H_{30}FIN_3O_6^+$.

EXAMPLE 25

(S)-2-{(R)-4-[4-((R)-2,3-Dihydroxy-propoxy)-phenyl]-2,5-dioxo-imidazolidin-1-yl}-N-(2-fluoro-4-iodo-phenyl)-3-phenyl-propionamide

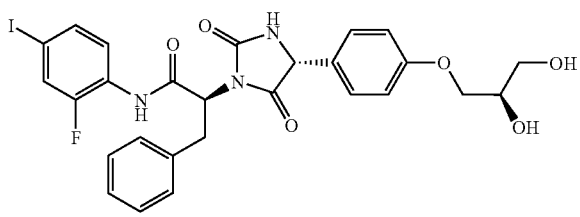

Prepared by the same method as described in example 2 except that (i) 2-fluoro-4-iodoaniline was used in place of 4-bromo-2-fluoro-aniline, and (ii)((S)-2-tert-butoxycarbonylamino-3-phenyl-propionic acid was used in place of (2S,3S)-2-tert-butoxycarbonylamino-3-phenyl-butyric acid.

HRMS: Obs Mass (M+H$^+$), 634.0839. Calcd. Mass, 634.0845 for $C_{27}H_{26}FIN_3O_6^+$.

EXAMPLE 26

(S)-2-[(R)-4-(4-Acetylamino-phenyl)-2,5-dioxo-imidazolidin-1-yl]-N-(2-fluoro-4-iodo-phenyl)-3-phenyl-propionamide

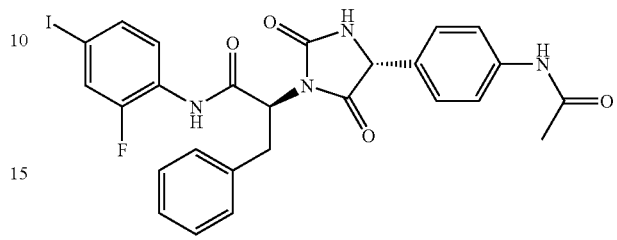

Prepared by the same method as described in example 29 except that (2R)-(4-acetylamino-phenyl)-tert-butoxycarbonylamino-acetic acid was used in place of (2R)-tert-butoxycarbonylamino-(2,3-dihydro-benzo[1,4]dioxin-6-yl)-acetic acid. (2R)-(4-acetylamino-phenyl)-tert-butoxycarbonylamino-acetic acid was prepared as follows:

(1) To a suspension of (2R)-amino-phenyl-acetic acid (10.0 g, 66.2 mmol) in water (300 mL) was added sodium hydroxide (2.65 g, 66.3 mmol). After stirring for 2 minutes acetic anhydride (12.5 mL, 132.2 mmol) was added and the mixture stirred at ambient temperature for 15 minutes. The reaction mixture was acidified to pH=1 with 1M aqueous hydrochloric acid and the colorless precipitate of (2R)-acetylamino-phenyl-acetic acid collected by filtration and dried (10.24 g, 80%).

LC-MS: Obs. Mass, 194. Calcd. Mass, 194 for $C_{10}H_{12}NO_3^+$.

(2) (2R)-Acetylamino-phenyl-acetic acid (9.7 g, 50.5 mmol) was dissolved in concentrated sulfuric acid (25 mL) at −10° C. and concentrated nitric acid (4.2 mL, 100 mmol) added dropwise with stirring while maintaining the temperature below 0° C. After stirring for 30 minutes at −10° C. the reaction mixture was poured onto ice (150 g) and after thawing, filtration and drying (2R)-acetylamino-(4-nitro-phenyl)-acetic acid was obtained as a colorless solid (8.75 g, 73%).

LC-MS: Obs. Mass, 239. Calcd. Mass, 194 for $C_{10}H_{11}N_2O_5^+$.

(3) (2R)-Acetylamino-(4-nitro-phenyl)-acetic (500 mg, 2.10 mmol) was heated to 100° C. under reflux in 2M aqueous hydrochloric acid for 3.5 hours. The reaction mixture was cooled to ambient temperature and half of the reaction mixture was dried by lyophilization. The residue from lyophilization was suspended in water (2 mL), and treated with saturated aqueous sodium carbonate solution to obtain a solution with pH=10. p-Dioxane (6 mL) was added to the aqueous mixture followed by di-tert-butyldicarbonate (368 μL, 1.6 mmol) and the mixture stirred at ambient temperature for 3 hours. The reaction mixture was acidified with 20% w/v aqueous citric acid solution then extracted with ethyl acetate (three times), the combined organic layers dried over sodium sulfate, filtered and concentrated in vacuo. The residue was purified by chromatography over silica gel gradient eluted using 0 to 10% v/v methanol in dichloromethane to afford (2R)-tert-butoxycarbonylamino-(4-nitro-phenyl)-acetic acid as a colorless oil (372 mg, >100%).

LC-MS: Obs. Mass, 297. Calcd. Mass, 297 for $C_{13}H_{17}N_2O_6^+$.

To a solution of (2R)-tert-butoxycarbonylamino-(4-nitrophenyl)-acetic acid (350 mg, <1.18 mmol) in absolute ethanol (15 mL) was added a small amount of 10% palladium on carbon and the mixture stirred under an atmosphere of hydrogen for 16 hours. The reaction mixture was filtered through a pad of Celite and the Celite eluted with absolute ethanol. The filtrate was concentrated in vacuo then purified by chromatography over silica gel gradient eluted between 0 and 7% v/v methanol in dichloromethane. (2R)-(4-Amino-phenyl)-tert-butoxycarbonylamino-acetic acid was obtained as a yellow oil (146 mg, 46%).

LC-MS: Obs. Mass, 267. Calcd. Mass, 267 for $C_{13}H_{19}N_2O_4^+$.

(4) To a solution of (2R)-(4-amino-phenyl)-tert-butoxycarbonylamino-acetic acid (100 mg, 0.376 mmol) in dichloromethane (2 mL) was added pyridine (36 μL, 0.45 mmol) and acetic anhydride (42 μL, 0.44 mmol) and the mixture stirred at ambient temperature for 2 hours. The reaction mixture was diluted with dichloromethane, washed with 1M aqueous citric acid solution, brine, dried over sodium sulfate, filtered and concentrated in vacuo. The residue was purified by chromatography over silica gel gradient eluted from 0 to 10% v/v methanol in dichloromethane to afford (2R)-(4-acetylamino-phenyl)-tert-butoxycarbonylamino-acetic acid as a yellow solid (59 mg, 51%).

LC-MS: Obs. Mass, 307. Calcd. Mass, 307 for $C_{15}H_{19}N_2O_5^-$.

LC-MS: Obs. Mass (M+H+), 601. Calcd. Mass, 601 for $C_{26}H_{23}FIN_4O_4^+$.

EXAMPLE 27

(S)—N-(2-Fluoro-4-iodo-phenyl)-2-{(R)-4-[4-(2-methoxy-acetylamino)-phenyl]-2,5-dioxo-imidazolidin-1-yl}-3-phenyl-propionamide

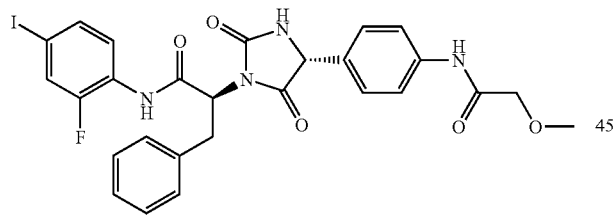

Prepared by the same method as described in example 1 except that (i) 2-fluoro-4-iodoaniline was used in place of 4-bromoaniline in step 2, (ii) O-benzotriazol-1-yl-N,N,N',N'-bis(tetramethylene)uronium hexaflurorophosphate was used as the coupling reagent in place of O-benzotriazol-1-yl-N,N,N',N'-tetramethyluronium hexaflurorophosphate in step 4, and (iii) (R)-tert-butoxycarbonylamino-[4-(2-methoxy-acetylamino)-phenyl]-acetic acid was used in place of (R)-tert-butyloxycarbonylamino-4-methyoxyphenyl-glycine in step 4. (R)-tert-Butoxycarbonylamino-[4-(2-methoxy-acetylamino)-phenyl]-acetic acid was prepared by the same method as described for preparation of (R)-(4-acetylamino-phenyl)-tert-butoxycarbonyl-amino-acetic acid in example 26 except that methoxy-acetyl chloride was used in place of acetic anhydride in step 5.

LC-MS: Obs. Mass (M+H+), 631. Calcd. Mass, 631 for $C_{27}H_{25}FIN_4O_5^+$.

EXAMPLE 28

(S)-2-{(R)-4-[4-(2-Dimethylamino-acetylamino)-phenyl]-2,5-dioxo-imidazolidin-1-yl}-N-(2-fluoro-4-iodo-phenyl)-3-phenyl-propionamide

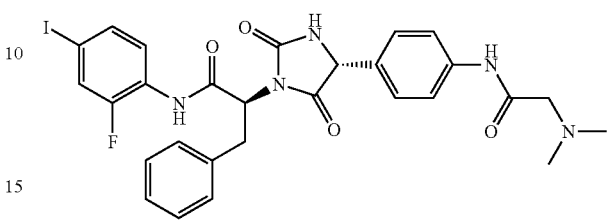

Prepared by the same method as described in example 1 except that (i) 2-fluoro-4-iodoaniline was used in place of 4-bromoaniline in step 2, (ii) O-benzotriazol-1-yl-N,N,'N',N-bis(tetramethylene)uronium hexaflurorophosphate was used as the coupling reagent in place of O-benzotriazol-1-yl-N,N,N',N'-tetramethyluronium hexaflurorophosphate in step 4, and (iii) and (R)-tert-butoxycarbonylamino-[4-(2-dimethylamino-acetylamino)-phenyl]-acetic acid was used in place of (R)-tert-butyloxycarbonylamino-4-methyoxyphenyl-glycine in step 4. (R)-tert-Butoxycarbonylamino-[4-(2-dimethylamino-acetylamino)-phenyl]-acetic acid was prepared by the same method as described for preparation of (R)-(4-acetylamino-phenyl)-tert-butoxycarbonyl-amino-acetic acid in example 26 except that 2-dimethylamino-acetyl chloride was used in place of acetic anhydride in step 5.

LC-MS: Obs. Mass (M+H+), 644. Calcd. Mass, 644 for $C_{28}H_{28}FIN_5O_4^+$.

EXAMPLE 29

(S)-2-[(R)-4-(2,3-Dihydro-benzo[1,4]dioxin-6-yl)-2,5-dioxo-imidazolidin-1-yl]-N-(2-fluoro-4-iodo-phenyl)-3-phenyl-propionamide

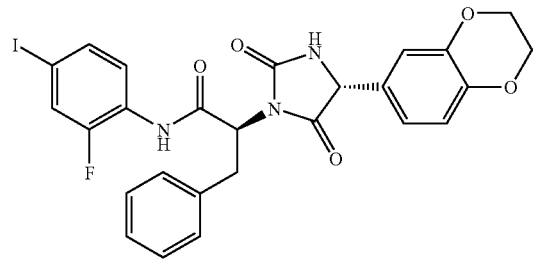

Prepared by the same method as described in example 18 except that (i) (2S)-2-tert-butoxycarbonylamino-3-phenyl-propionic acid was used in place of (2S,3S)-2-tert-butoxycarbonylamino-3-phenyl-butyric acid in step 1, and (ii) (2R)-tert-butoxycarbonylamino-(2,3-dihydro-benzo[1,4]dioxin-6-yl)-acetic acid (prepared according to the procedure of Bohme, E. H. W. et al., *J. Med. Chem.* 1980, 23, 405-412), was used in place of (R)-tert-butoxycarbonylamino-{4-[2-(tetrahydro-pyran-2-yloxy)-ethoxy]-phenyl}-acetic acid in step 4.

HRMS: Obs. Mass (M+H+), 602.0587. Calcd. Mass, 602.0583 for $C_{26}H_{22}FIN_3O_5^+$.

EXAMPLE 30

(S)—N-(2-Fluoro-4-iodo-phenyl)-2-[(R)-4-(4-methoxy-phenyl)-2,5-dioxo-imidazolidin-1-yl]-3-p-tolyl-propionamide

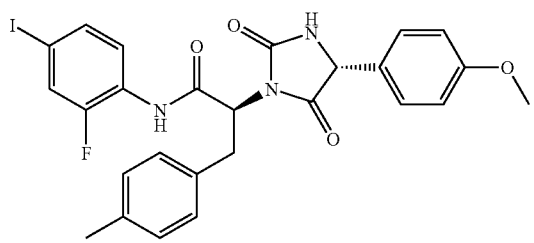

Prepared by the same method as described in example 1 except that (i) (S)-2-tert-butoxycarbonylamino-3-p-tolyl-propionic acid was used in place of (2S,3S)-2-tert-butoxycarbonylamino-3-phenyl-butyric acid in step 1, and (ii) 2-fluoro-4-iodoaniline was used in place of 4-bromoaniline in step 2.

HRMS: Obs. Mass (M+Na$^+$), 610.0613. Calcd. Mass, 610.0609 for $C_{26}H_{23}FIN_3NaO_4^+$.

EXAMPLE 31

(S)—N-(2-Fluoro-4-iodo-phenyl)-3-(4-fluoro-phenyl)-2-[(R)-4-(4-methoxy-phenyl)-2,5-dioxo-imidazolidin-1-yl]-propionamide

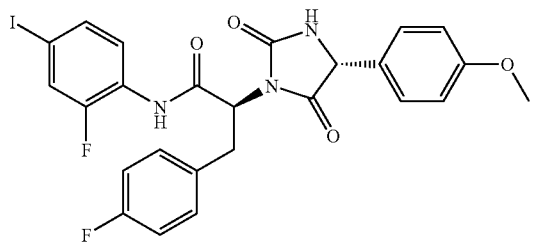

Prepared by the same method as described in example 4 except that (i) (S)-2-tert-butoxycarbonylamino-3-(4-fluorophenyl)-propionic acid was used in place of (S)-2-tert-butoxycarbonylamino-3-phenyl-propionic acid in step 1, and (ii) 2-fluoro-4-iodoaniline was used in place of 4-iodoaniline in step 2.

HRMS: Obs Mass (M+H$^+$), 592.0539. Calcd. Mass, 592.0540 for $C_{25}H_{21}F_2N_3O_4^+$.

EXAMPLE 32

(S)-3-(4-Chloro-phenyl)-N-(2-fluoro-4-iodo-phenyl)-2-[(R)-4-(4-methoxy-phenyl)-2,5-dioxo-imidazolidin-1-yl]-propionamide

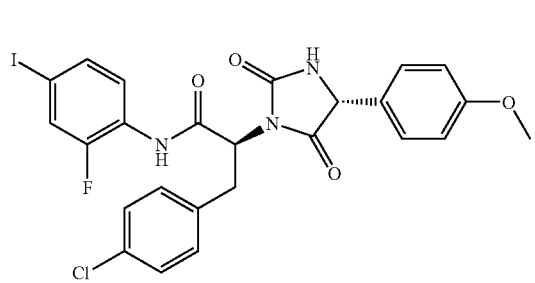

Prepared by the same method as described in example 1 except that (i) (S)-2-tert-butoxycarbonylamino-3-p-chloro-propionic acid was used in place of (2S,3S)-2-tert-butoxycarbonylamino-3-phenyl-butyric acid in step 1, and (ii) 2-fluoro-4-iodoaniline was used in place of 4-bromoaniline in step 2.

HRMS: Obs Mass (M+H$^+$), 608.0241. Calcd. Mass, 608.0244 for $C_{25}H_{21}ClFIN_3O_4^+$.

EXAMPLE 33

(S)-3-(4-Cyano-phenyl)-N-(2-fluoro-4-iodo-phenyl)-2-[(R)-4-(4-methoxy-phenyl)-2,5-dioxo-imidazolidin-1-yl]-propionamide

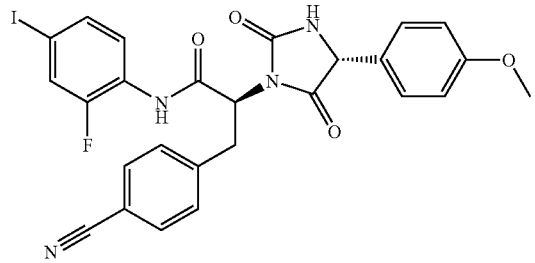

Prepared by the same method as described in example 1 except that (i) (S)-2-tert-butoxycarbonylamino-3-(4-cyanophenyl)-propionic acid was used in place of (2S,3S)-2-tert-butoxycarbonylamino-3-phenyl-butyric acid in step 1, and (ii) 2-fluoro-4-iodoaniline was used in place of 4-bromoaniline in step 2.

HRMS: Obs Mass (M+H$^+$), 599.0575. Calcd. Mass, 599.0586 for $C_{26}H_{21}FIN_4O_4^+$.

EXAMPLE 34

(S)—N-(2-Fluoro-4-iodo-phenyl)-3-(4-methoxy-phenyl)-2-[(R)-4-(4-methoxy-phenyl)-2,5-dioxo-imidazolidin-1-yl]-propionamide

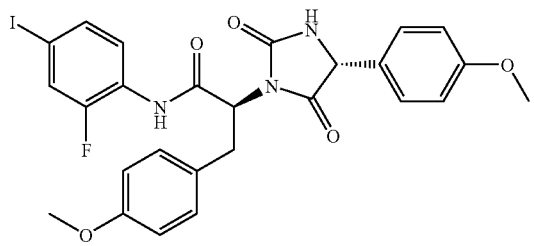

Prepared by the same method as described in example 1 except that (i) (S)-2-tert-butoxycarbonylamino-3-(4-methoxy-phenyl)-propionic acid was used in place of (2S,3S)-2-tert-butoxycarbonylamino-3-phenyl-butyric acid in step 1, and (ii) 2-fluoro-4-iodoaniline was used in place of 4-bromoaniline in step 2.

HRMS: Obs Mass (M+H$^+$), 604.0739. Calcd. Mass, 604.0739 for $C_{26}H_{24}FIN_3O_5^+$.

EXAMPLE 35

(S)—N-(2-Fluoro-4-iodo-phenyl)-2-[(R)-4-(4-methoxy-phenyl)-2,5-dioxo-imidazolidin-1-yl]-3-(4-trifluoromethyl-phenyl)-propionamide

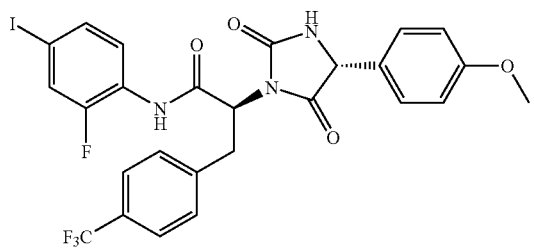

Prepared by the same method as described in example 1 except that (i) (S)-2-tert-butoxycarbonylamino-3-(4-trifluoromethyl-phenyl)-propionic acid was used in place of (2S,3S)-2-tert-butoxycarbonylamino-3-phenyl-butyric acid in step 1, and (ii) 2-fluoro-4-iodoaniline was used in place of 4-bromoaniline in step 2.

HRMS: Obs Mass (M+H$^+$), 642.0507. Calcd. Mass, 642.0508 for $C_{26}H_{21}F_4, N_3O_4^+$.

EXAMPLE 36

(S)—N-(2-Fluoro-4-iodo-phenyl)-3-(3-fluoro-phenyl)-2-[(R)-4-(4-methoxy-phenyl)-2,5-dioxo-imidazolidin-1-yl]-propionamide

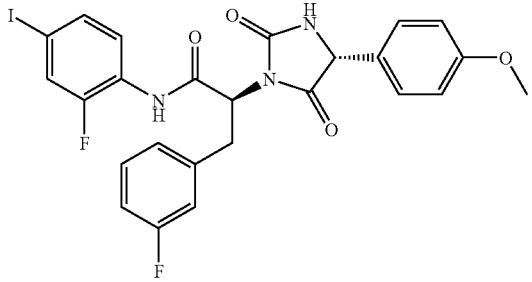

Prepared by the same method as described in example 1 except that (i) (S)-2-tert-butoxycarbonylamino-3-(3-fluoro-phenyl)-propionic acid was used in place of (2S,3S)-2-tert-butoxycarbonylamino-3-phenyl-butyric acid in step 1, and (ii) 2-fluoro-4-iodoaniline was used in place of 4-bromoaniline in step 2.

HRMS: Obs Mass (M+Na$^+$), 614.0350. Calcd. Mass, 614.0359 for $C_{25}H_{20}F_2, N_3NaO_4^+$.

EXAMPLE 37

(S)—N-(2-Fluoro-4-iodo-phenyl)-2-[(R)-4-(4-methoxy-phenyl)-2,5-dioxo-imidazolidin-1-yl]-3-m-tolyl-propionamide Prepared by the same method as described in example 1 except that (i) (S)-2-tert-butoxycarbonylamino-3-m-tolyl-propionic acid was used in place of (2S,3S)-2-tert-butoxycarbonylamino-3-phenyl-butyric acid in step 1, and (ii) 2-fluoro-4-iodoaniline was used in place of 4-bromoaniline in step 2.

HRMS: Obs. Mass (M+Na$^+$), 610.0607. Calcd. Mass, 610.0609 for $C_{26}H_{23}FIN_3NaO_4^+$.

EXAMPLE 38

(S)—N-(2-Fluoro-4-iodo-phenyl)-2-[(R)-4-(4-methoxy-phenyl)-2,5-dioxo-imidazolidin-1-yl]-3-o-tolyl-propionamide

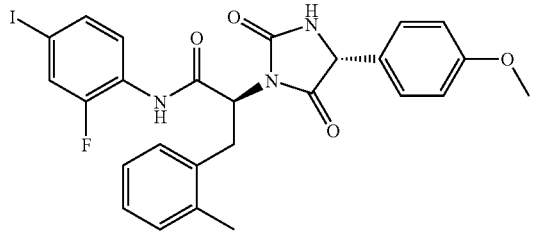

Prepared by the same method as described in example 1 except that (i) (S)-2-tert-butoxycarbonylamino-3-o-tolyl-propionic acid was used in place of (2S,3S)-2-tert-butoxycarbonylamino-3-phenyl-butyric acid in step 1, and (ii) 2-fluoro-4-iodoaniline was used in place of 4-bromoaniline in step 2.

HRMS: Obs. Mass (M+H$^+$), 588.0791. Calcd. Mass, 588.0790 for $C_{26}H_{24}FIN_3O_4{}^+$.

EXAMPLE 39

(S)—N-(2-Fluoro-4-iodo-phenyl)-3-(2-methoxy-phenyl)-2-[(R)-4-(4-methoxy-phenyl)-2,5-dioxo-imidazolidin-1-yl]-propionamide

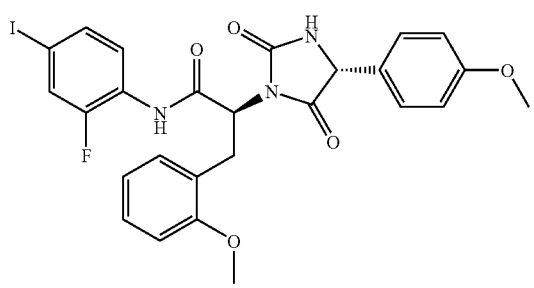

Prepared by the same method as described in example 4 except that (i) (S)-2-tert-butoxycarbonylamino-3-(2-methoxy-phenyl)-propionic acid was used in place of (S)-2-tert-butyloxycarbonylamino-3-phenyl-propionic acid in step 1, and (ii) 2-fluoro-4-iodoaniline was used in place of 4-iodoaniline in step 2.

HRMS: Obs Mass (M+H$^+$), 604.0745 Calcd. Mass, 604.0739 for $C_{26}H_{24}FIN_3O_5{}^+$.

EXAMPLE 40

(S)—N-(2-Fluoro-4-iodo-phenyl)-2-{(R)-4-[4-(2-hydroxy-ethoxy)-phenyl]-2,5-dioxo-imidazolidin-1-yl}-3-(2-methoxy-phenyl)-propionamide

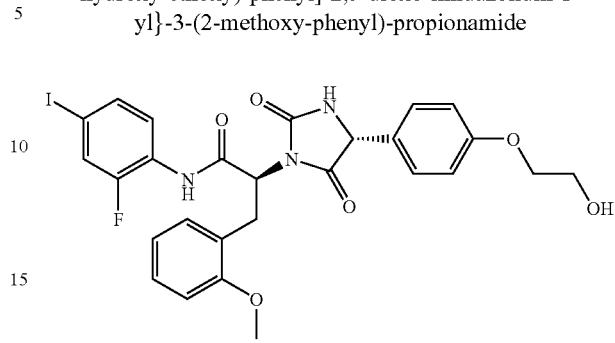

Prepared by the same method as described in example 39 except that (i) (R)-tert-butoxycarbonylamino-{4-[2-(tetrahydro-pyran-2-yloxy)-ethoxy]-phenyl}-acetic acid (prepared as described in example 48) was used in place of (R)-tert-butyloxycarbonylamino-4-methoxyphenylglycine in step 4, and (ii) step 6 was performed as described in example 48.

HRMS: Obs Mass (M+H$^+$), 634.0842 Calcd. Mass, 634.0845 for $C_{27}H_{26}FIN_3O_6{}^+$.

EXAMPLE 41

N-(2-Fluoro-4-iodo-phenyl)-2-[(R)-4-(4-methoxy-phenyl)-2,5-dioxo-imidazolidin-1-yl]-3-(2-trifluoromethyl-phenyl)-propionamide, isomer 1

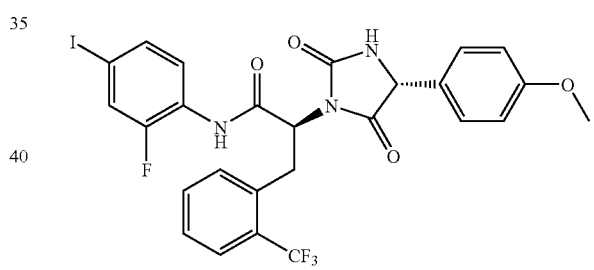

Prepared by the same method as described in example 4 except that (i) (S)-2-tert-butoxycarbonylamino-3-(2-trifluoromethyl-phenyl)-propionic acid was used in place of (S)-2-tert-butoxycarbonylamino-3-phenyl-propionic acid in step 1, (ii) 2-fluoro-4-iodoaniline was used in place of 4-iodoaniline in step 2, (iii) the trifluoroacetic acid salt of (S)-2-amino-N-(2-fluoro-4-iodo-phenyl)-3-(2-trifluoromethyl-phenyl)-propionamide was isolated in step 3 and used directly in step 4 with 1.0 equivalent of triethylamine and (3-dimethylaminopropyl)-ethyl-carbodiimide hydrochloride as the coupling reagent in place of O-benzotriazol-1-yl-N,N,N',N'-tetramethyluronium hexaflurorophosphate, and (iv) after performing step 5, the diastereomers (resulting from racemization in step 2) of 2-[(R)-2-amino-2-(4-methoxy-phenyl)-acetylamino]-N-(2-fluoro-4-iodo-phenyl)-3-(2-trifluoromethyl-phenyl)-propionamide were separated by chromatography over silica gel gradient eluted between 40 and 60% v/v ethyl acetate in hexane. The slower moving component was collected and after concentration in vacuo carried on to step 6.

HRMS: Obs Mass (M+H$^+$), 642.0502 Calcd. Mass, 642.0508 for $C_{26}H_{21}F_4, N_3O_4{}^+$.

EXAMPLE 42

N-(2-Fluoro-4-iodo-phenyl)-2-[(R)-4-(4-methoxy-phenyl)-2,5-dioxo-imidazolidin-1-yl]-3-(2-trifluoromethyl-phenyl)-propionamide, isomer 2

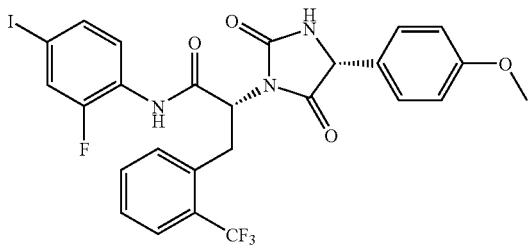

Prepared by the same method as described in example 41 except that the faster moving component from the chromatographic separation of the diastereomers of 2-[(R)-2-amino-2-(4-methoxy-phenyl)-acetylamino]-N-(2-fluoro-4-iodo-phenyl)-3-(2-trifluoromethyl-phenyl)-propionamide was collected and after concentration in vacuo carried on to step 6.

HRMS: Obs Mass (M+Na$^+$), 664.0327 Calcd. Mass, 664.0327 for $C_{26}H_{20}F_4, N_3NaO_4^+$.

EXAMPLE 43

(S)—N-(2-Fluoro-4-iodo-phenyl)-2-{(R)-4-[4-(2-hydroxy-ethoxy)-phenyl]-2,5-dioxo-imidazolidin-1-yl}-3-naphthalen-2-yl-propionamide

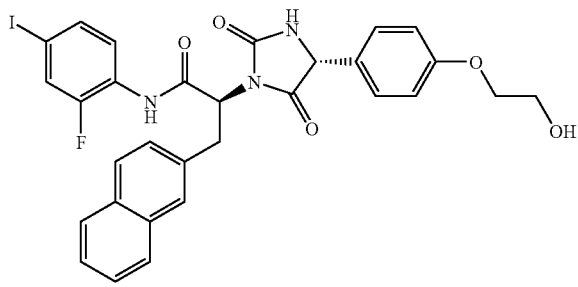

Prepared by the same method as described in example 48 except that (i) steps 1-2 described below were performed in place of the steps 1-3 described in example 48, and (ii) O-benzotriazol-1-yl-N,N,N',N'-bis(tetramethylene)uronium hexaflurorophosphate was used as the coupling reagent in place of O-benzotriazol-1-yl-N,N,N',N'-tetramethyluronium hexaflurorophosphate in step 4.

Step 1: To a solution of (S)-2-(9H-fluoren-9-ylmethoxycarbonylamino)-3-naphthalen-2-yl-propionic acid (1.0 g, 2.30 mmol) and 2-fluoro-4-iodoaniline (434 mg, 1.84 mmol), triphenylphosphine (0.94 g, 3.45 mmol) and pyridine (0.39 mL, 4.60 mmol) in dichloromethane (10 mL) at 0° C. was added N-bromosuccinimide (0.61 mg, 3.45 mmol) in two portions under an atmosphere of dry nitrogen. The mixture was stirred for 2 hours at 0° C. The reaction mixture was purified by chromatography over silica gel gradient eluted from 100% dichloromethane up to 10% methanol/90% dichloromethane over 30 minutes. Concentration of the product containing fractions gave [(S)-1-(2-fluoro-4-iodo-phenylcarbamoyl)-2-naphthalen-2-yl-ethyl]-carbamic acid 9H-fluoren-9-ylmethyl ester as a yellow solid foam (1.05 g, 70%).

LC-MS: Obs. Mass (M+H$^+$), 657. Calcd. Mass, 657 for $C_{34}H_{27}FIN_2O_3^+$.

Step 2: To a solution of [(S)-1-(2-fluoro-4-iodo-phenylcarbamoyl)-2-naphthalen-2-yl-ethyl]-carbamic acid 9H-fluoren-9-ylmethyl ester (1.05 g, 1.60 mmol) in dichloromethane (24 mL) was added piperidine (6 mL) and the mixture stirred at room temperature for 1 hour. After removal of the solvent, the residue was purified by chromatography over silica gel gradient eluted from 100% hexane up to 40% ethyl acetate/60% hexane in 30 minutes. Concentration of the product containing fractions gave (S)-2-amino-N-(2-fluoro-4-iodo-phenyl)-3-naphthalen-2-yl-propionamide as a yellow solid (390 mg, 56%).

LC-MS: Obs. Mass (M+H$^+$), 435. Calcd. Mass, 435 for $C_{19}H_{17}FIN_2O+$.

LC-MS: Obs. Mass (M+H$^+$), 654. Calcd. Mass, 654 for $C_{30}H_{26}FIN_3O_5^+$.

EXAMPLE 44

(2S,3S)-2-((R)-2,5-Dioxo-4-phenyl-imidazolidin-1-yl)-N-(2-fluoro-4-iodo-phenyl)-3-phenyl-butyramide

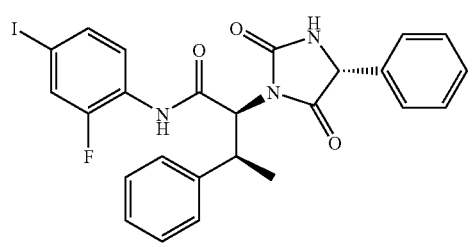

Prepared by the same method as described in example 1 except that (i) 2-fluoro-4-iodoaniline was used in place of 4-bromoaniline in step 2, and (ii) (R)-tert-butoxycarbonylamino phenyl-acetic acid was used in place of (R)-tert-butoxycarbonylamino [4-methoxy-phenyl]-acetic acid in step 4.

HRMS: Obs Mass (M+Na$^+$), 580.0492. Calcd. Mass, 580.0504 for $C_{25}H_{21}FIN_3NaO_3^+$.

EXAMPLE 45

(2S,3S)—N-(2-Fluoro-4-iodo-phenyl)-2-[(R)-4-(4-methoxy-phenyl)-2,5-dioxo-imidazolidin-1-yl]-3-phenyl-butyramide)

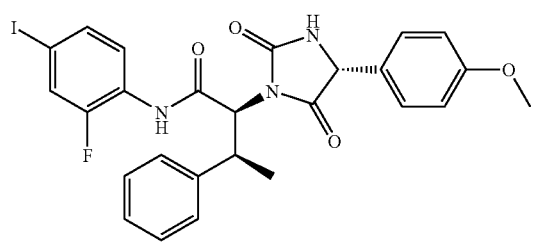

Prepared by the same method as described in example 1 except that 2-fluoro-4-iodoaniline was used in place of 4-bromoaniline in step 2.

HRMS: Obs Mass (M+H$^+$), 588.0791. Calcd. Mass, 588.0790 for $C_{26}H_{24}FIN_3O_4^+$.

EXAMPLE 46

(2S,3S)-2-[(R)-4-(4-Ethoxy-phenyl)-2,5-dioxo-imidazolidin-1-yl]-N-(2-fluoro-4-iodo-phenyl)-3-phenyl-butyramide

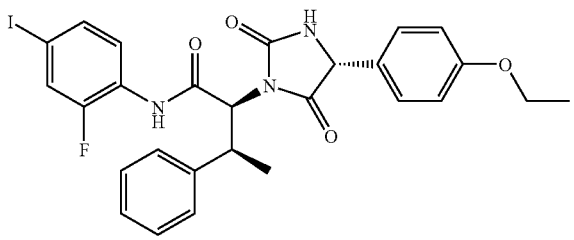

Prepared by the same method as described in example 44 except that (R)-tert-butoxycarbonylamino-(4-ethoxy-phenyl)-acetic acid was used in place of (R)-tert-butoxycarbonylamino-phenyl-acetic acid in step 4. (R)-tert-Butoxycarbonylamino-(4-ethoxy-phenyl)-acetic acid was prepared as described in example 1 step 4 for the preparation of (R)-tert-butoxycarbonylamino-(4-methoxy-phenyl)-acetic acid except that ethyl iodide was used in place of methyl iodide.

HRMS: Obs Mass (M+H$^+$), 602.0944. Calcd. Mass, 602.0947 for $C_{27}H_{26}FIN_3O_4^+$.

EXAMPLE 47

(2S,3S)-2-[(R)-4-(4-Cyclopropylmethoxy-phenyl)-2,5-dioxo-imidazolidin-1-yl]-N-(2-fluoro-4-iodo-phenyl)-3-phenyl-butyramide

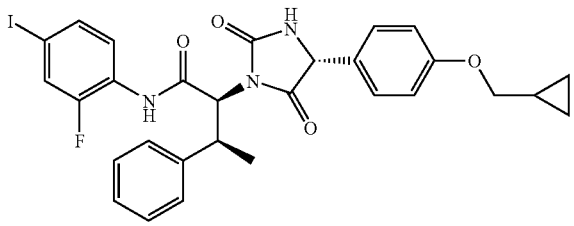

Prepared by the same method as described in example 46 except that (R)-tert-butoxycarbonylamino-(4-cyclopropylmethoxy-phenyl)-acetic acid was used in place of (R)-tert-butoxycarbonylamino-(4-ethoxy-phenyl)-acetic acid. (R)-tert-Butoxycarbonylamino-(4-cyclopropylmethoxy-phenyl)-acetic acid was prepared as described in example 46 except that bromomethylcylopropane was used in place of ethyl iodide.

HRMS: Obs Mass (M+H$^+$), 628.1094. Calcd. Mass, 628.1103 for $C_{29}H_{28}FIN_3O_4^+$.

EXAMPLE 48

(2S,3S)—N-(2-Fluoro-4-iodo-phenyl)-2-{(R)-4-[4-(2-hydroxy-ethoxy)-phenyl]-2,5-dioxo-imidazolidin-1-yl}-3-phenyl-butyramide

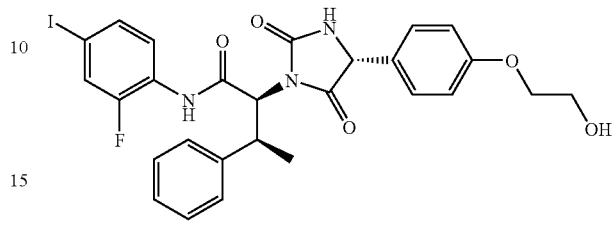

Prepared by the same method as described in example 1 except that (i) 2-fluoro-4-iodoaniline was used in place of 4-bromoaniline in step 2, (ii) (R)-tert-butoxycarbonylamino-{4-[2-(tetrahydro-pyran-2-yloxy)-ethoxy]-phenyl}-acetic acid (prepared as described below) was used in place of (R)-tert-butyloxycarbonylamino-4-methoxyphenylglycine in step 4, and (iii) step 6 was performed as described below.

Preparation of (R)-tert-butoxycarbonylamino-{4-[2-(tetrahydro-pyran-2-yloxy)-ethoxy]-phenyl}-acetic acid: (R)-tert-butoxycarbonylamino-(4-hydroxy-phenyl)-acetic acid (2.67 g, 10 mmol) (Salituro, G. M.; Townsend, C. A. J. Am. Chem. Soc. 1990, 112, 760-770) was dissolved in N,N-dimethylformamide (70 mL) in an ice bath. Sodium hydride (0.88 g, 60% in mineral oil, 22 mmol) was added in small portions. The mixture was warmed up to 10° C. for 1 hour. 2-(2-Bromo-ethoxy)-tetrahydropyran (1.7 mol, 11 mmol) in N,N-dimethylformamide (20 mL) was added drop wise. The reaction mixture was stirred for 24 hours and then diluted with ice/water. The mixture was extracted with ethyl acetate. The aqueous layer was cooled in an ice bath and acidified using 1.5 M aqueous potassium hydrogen sulfate to pH=2-3. The resulting mixture was extracted with ethyl acetate (5×), washed with water (5×), brine and dried over sodium sulfate. Filtration and evaporation of the solvents gave (R)-tert-butoxycarbonylamino-{4-[2-(tetrahydropyran-2-yloxy)-ethoxy]-phenyl}-acetic acid as a solid white foam (3.2 g, 82%).

Step 6: To a solution of diphosgene (21.1 µL, 0.173 mmol) in 1:1 v/v toluene/tetrahydrofuran (20 mL total) at −40° C. was added a mixture of (2S,3S)-2-{(R)-2-amino-2-[4-(2-hydroxy-ethoxy)-phenyl]-acetylamino}-N-(2-fluoro-4-iodo-phenyl)-3-phenyl-butyramide (180 mg, 0.289 mmol) and N,N-diisopropylethylamine (154 µL, 0.867 mmol) in dry dichloromethane (40 mL) over 5 minutes and the remaining residue washed in to the reaction mixture with a small amount of dry dichloromethane. After 20 minutes at −40° C. the temperature was raised to −20° C. for an additional 15 minutes to complete reaction. The colorless solution was diluted with ethyl acetate (100 mL) and washed sequentially with 1.5 M aqueous potassium hydrogen sulfate (twice), 5% w/v aqueous sodium hydrogen carbonate solution (once) and brine (once). The aqueous layers were back extracted with ethyl acetate (2×50 mL). The combined ethyl acetate extracts were diluted with an equal volume of dichloromethane and passed through a column of sodium sulfate on top of a 4" column of flash silica gel. The eluant was concentrated to afford a pale yellow residue (177 mg). The residue was triturated with dichloromethane (5×2 mL) and the combined organic solutions purified by chromatography over silica gel (deactivated prior to use with methanol) gradient eluted in 1% steps from 100% dichloromethane up to 3% methanol/97% dichloromethane. Concentration of the product containing fractions gave a glassy residue (98 mg). The residue was dissolved in a small volume of dichloromethane, diluted with diethyl ether (1 mL) and the product was precipitated by the addition of hexanes (10 mL). The product was isolated by filtration, washed with hexanes and dried in vacuo to give (2S,3S)—N-(2-fluoro-4-iodo-phenyl)-2-{(R)-4-[4-(2-hydroxy-ethoxy)-phenyl]-2,5-dioxo-imidazolidin-1-yl}-3-phenyl-butyramide as a colorless solid (81 mg).

HRMS: Obs. Mass (M+Na$^+$), 640.0713. Calcd. Mass, 640.0715 for $C_{27}H_{25}FIN_3NaO_5^+$.

LC-MS (reverse phase HPLC, C18 column, water/acetonitrile gradient): $R_t$=2.29 minutes, Obs. Mass (M+Na$^+$), 640. Calcd. Mass, 640 for $C_{27}H_{25}FIN_3NaO_5^+$.

$^1$H NMR (DMSO-d$_6$, 300 MHz) $\delta_H$ 10.11 (s, 1H), 8.53 (s, 1H), 5.02 (d, J=11.8 Hz, 1H) ppm (characteristic resonances).

EXAMPLE 49

(2S,3S)—N-(2-Fluoro-4-iodo-phenyl)-2-{(S)-4-[4-(2-hydroxy-ethoxy)-phenyl]-2,5-dioxo-imidazolidin-1-yl}-3-phenyl-butyramide

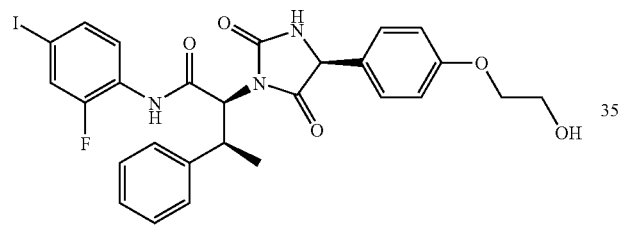

A solution of (2S,3S)—N-(2-fluoro-4-iodo-phenyl)-2-{(R)-4-[4-(2-hydroxy-ethoxy)-phenyl]-2,5-dioxo-imidazolidin-1-yl}-3-phenyl-butyramide (prepared as described in example 48) (50 mg, 0.081 mmol) was dissolved in methanol (3 mL) and stirred at ambient temperature for 4 days. The resulting mixture of isomers was concentrated in vacuo and then purified by super-critical fluid chromatography using a Chiracel OJ column eluted with carbon dioxide at 100 bar and 30° C. modified with 35% v/v ethanol in acetonitrile eluted at 2 mL/minute. The first eluted compound was collected and concentrated in vacuo to obtain (2S,3S)—N-(2-fluoro-4-iodo-phenyl)-2-{(S)-4-[4-(2-hydroxy-ethoxy)-phenyl]-2,5-dioxo-imidazolidin-1-yl}-3-phenyl-butyramide (9.1 mg, 18%) The compound eluted second was identical with (2S,3S)—N-(2-fluoro-4-iodo-phenyl)-2-{(R)-4-[4-(2-hydroxy-ethoxy)-phenyl]-2,5-dioxo-imidazolidin-1-yl}-3-phenyl-butyramide (19.9 mg, 40%).

LC-MS (reverse phase HPLC, C18 column, water/acetonitrile gradient): $R_t$=2.34 minutes, Obs. Mass (M+Na$^+$), 640. Calcd. Mass, 640 for $C_{27}H_{25}FIN_3NaO_5^+$.

$^1$H NMR (DMSO-d$_6$, 300 MHz) $\delta_H$ 10.18 (s, 1H), 8.57 (s, 1H), 4.84 (s, 1H) ppm (characteristic resonances).

EXAMPLE 50

(2S,3S)—N-(2-Fluoro-4-iodo-phenyl)-2{(R)-4-[4-(2-methoxy-ethoxy)-phenyl]-2,5-dioxo-imidazolidin-1-yl}-3-phenyl-butyramide

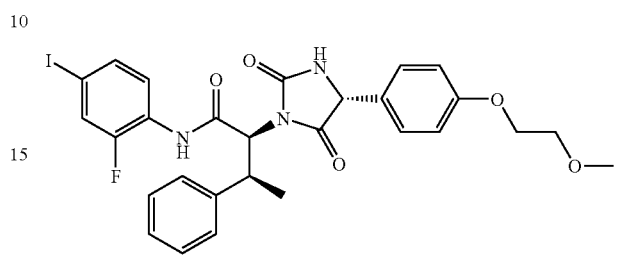

Prepared by the same method as that described in example 1 except that (i) 2-fluoro-4-iodoaniline was used in place of 4-bromoaniline in step 2, and (ii) (R)-tert-butoxycarbonylamino-[4-(2-methoxy-ethoxy)-phenyl]-acetic acid was used in place of (R)-tert-butoxycarbonylamino-[4-methoxy-phenyl]-acetic acid in step 4. (R)-tert-Butoxycarbonylamino-[4-(2-methoxy-ethoxy)-phenyl]-acetic acid was prepared as described in example 80.

HRMS: Obs Mass (M+H$^+$), 632.1053. Calcd. Mass, 632.1052 for $C_{28}H_{28}FIN_3O_5^+$.

EXAMPLE 51

(2S,3S)-2-{(R)-4-[4-(2-Ethoxy-ethoxy)-phenyl]-2,5-dioxo-imidazolidin-1-yl}-N-(2-fluoro-4-iodo-phenyl)-3-phenyl-butyramide

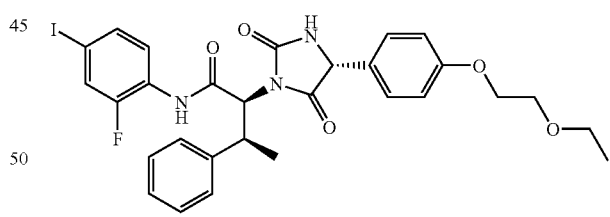

Prepared in a manner similar to that described in example 1 except that (i) 2-fluoro-4-iodoaniline was used in place of 4-bromoaniline in step 2, and (ii) (R)-tert-butoxycarbonylamino-[4-(2-ethoxy-ethoxy)-phenyl]-acetic acid was used in place of (R)-tert-butoxycarbonylamino-[4-methoxy-phenyl]-acetic acid in step 4. (R)-tert-Butoxycarbonylamino-[4-(2-ethoxy-ethoxy)-phenyl]-acetic acid was prepared as described in example 48 except that 1-bromo-2-ethoxyethane was used in place of 2-(2-bromo-ethoxy)-tetrahydropyran.

HRMS: Obs Mass (M+H$^+$), 646.1192. Calcd. Mass, 646.1209 for $C_{29}H_{30}FIN_3O_5^+$.

EXAMPLE 52

(2S,3S)—N-(2-Fluoro-4-iodo-phenyl)-2-{(R)-4-[4-(3-hydroxy-propoxy)-phenyl]-2,5-dioxo-imidazolidin-1-yl}-3-phenyl-butyramide

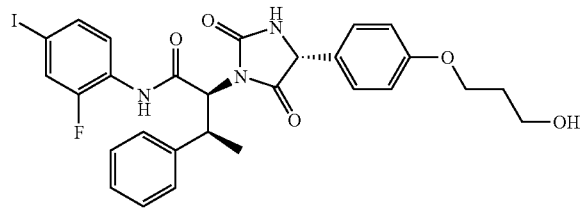

Prepared by the same method as described in example 48 except that (R)-tert-butoxycarbonylamino-{4-[3-(tetrahydro-pyran-2-yloxy)-propoxy]-phenyl}-acetic acid was used in place of (R)-tert-butoxycarbonylamino-{4-[2-(tetrahydro-pyran-2-yloxy)-ethoxy]-phenyl}acetic acid. (R)-tert-Butoxycarbonylamino-{4-[3-(tetrahydro-pyran-2-yloxy)-propoxy]-phenyl}-acetic acid was prepared as described in example 48 except that 2-(3-bromo-propoxy)-tetrahydropyran was used in place of 2-(2-bromo-ethoxy)-tetrahydropyran.

HRMS: Obs Mass (M+H$^+$), 632.1055. Calcd. Mass, 632.1052 for $C_{28}H_{28}FIN_3O_5^+$.

EXAMPLE 53

(2S,3S)—N-(2-Fluoro-4-iodo-phenyl)-2-{(R)-4-[4-(4-hydroxy-butoxy)-phenyl]-2,5-dioxo-imidazolidin-1-yl}-3-phenyl-butyramide

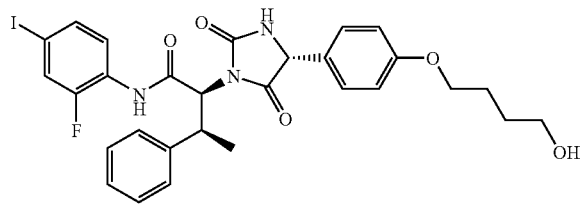

Prepared by the same method as described in example 48 except that (R)-tert-butoxycarbonylamino-{4-[4-(tetrahydro-pyran-2-yloxy)-butoxy]-phenyl}-acetic acid was used in place of (R)-tert-butoxycarbonylamino-{4-[2-(tetrahydro-pyran-2-yloxy)-ethoxy]-phenyl}-acetic acid. (R)-tert-Butoxycarbonylamino-{4-[4-(tetrahydro-pyran-2-yloxy)-butoxy]-phenyl}-acetic acid was prepared as described in example 48 except that 2-(4-bromo-butoxy)-tetrahydropyran was used in place of 2-(2-bromo-ethoxy)-tetrahydropyran.

HRMS: Obs Mass (M+H$^+$), 646.1208. Calcd. Mass, 646.1209 for $C_{29}H_{30}FIN_3O_5^+$.

EXAMPLE 54

(2S,3S)—N-(2-Fluoro-4-iodo-phenyl)-2-((R)$_4$-{4-[2-(2-hydroxy-ethoxy)-ethoxy]-phenyl}-2,5-dioxo-imidazolidin-1-yl)-3-phenyl-butyramide Prepared by the same method as described in example 48 except that (R)-tert-butoxycarbonylamino-(4-{2-[2-(tetrahydro-pyran-2-yloxy)-ethoxy]-ethoxy}-phenyl)-acetic acid was used in place of (R)-tert-butoxycarbonylamino-{4-[2-(tetrahydro-pyran-2-yloxy)-ethoxy]-phenyl}-acetic acid. (R)-tert-Butoxycarbonylamino-(4-{2-[2-(tetrahydro-pyran-2-yloxy)-ethoxy]-ethoxy}-phenyl)-acetic acid was prepared as described in example 48 except that 2-[2-(2-chloro-ethoxy)-ethoxy]-tetrahydro-pyran was used in place of 2-(2-bromo-ethoxy)-tetrahydropyran.

HRMS: Obs Mass (M+H$^+$), 662.1158. Calcd. Mass, 662.1158 for $C_{29}H_{30}FIN_3O_6^+$.

EXAMPLE 55

(2S,3S)—N-(2-Fluoro-4-iodo-phenyl)-2-((R)-4-{4-[2-(2-methoxy-ethoxy)-ethoxy]-phenyl}-2,5-dioxo-imidazolidin-1-yl)-3-phenyl-butyramide Prepared by the same method as that described in example 1 except that (i) 2-fluoro-4-iodoaniline was used in place of 4-bromoaniline in step 2, and (ii) (R)-tert-butoxycarbonylamino-[4-(2-{2-methoxy-ethoxy}-ethoxy)-phenyl]-acetic acid was used in place of (R)-tert-butoxycarbonylamino-[4-methoxy-phenyl]-acetic acid in step 4. (R)-tert-Butoxycarbonylamino-[4-(2-{2-methoxy-ethoxy}-ethoxy)-phenyl]-acetic acid was prepared as described in example 48 except that 1-(2-bromo-ethoxy)-2-methoxy-ethane was used in place of 2-(2-bromo-ethoxy)-tetrahydropyran.

HRMS: Obs Mass (M+H$^+$), 676.1306. Calcd. Mass, 676.1315 for $C_{30}H_{32}FIN_3O_6^+$.

EXAMPLE 56

(2S,3S)-2-{(R)-4-[4-((R)-2,3-Dihydroxy-propoxy)-phenyl]-2,5-dioxo-imidazolidin-1-yl}-N-(2-fluoro-4-iodo-phenyl)-3-phenyl-butyramide

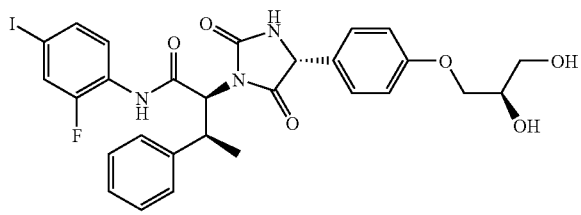

Prepared by the same method as described in example 114 except that 2-fluoro-4-iodoaniline was used in place of 2-chloro-4-iodoaniline in step 2.

HRMS: Obs Mass (M+H$^+$), 648.0995. Calcd. Mass, 648.1002 for $C_{28}H_{28}FIN_3O_6^+$.

LC-MS (reverse phase HPLC, C18 column, water/acetonitrile gradient): R$_t$=3.55 minutes, Obs. Mass (M+H$^+$), 648. Calcd. Mass, 648 for $C_{28}H_{28}FIN_3O_6^+$.

$^1$H NMR (DMSO-d$_6$, 300 MHz) δ$_H$ 10.11 (s, 1H), 8.52 (s, 1H), 5.02 (d, J=11.5 Hz, 1H) ppm (characteristic resonances).

EXAMPLE 57

(2S,3S)-2-{(S)-4-[4-((R)-2,3-Dihydroxy-propoxy)-phenyl]-2,5-dioxo-imidazolidin-1-yl}-N-(2-fluoro-4-iodo-phenyl)-3-phenyl-butyramide

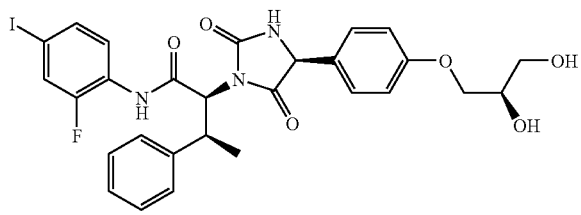

(2S,3S)-2-{(R)-4-[4-((R)-2,3-Dihydroxy-propoxy)-phenyl]-2,5-dioxo-imidazolidin-1-yl}-N-(2-fluoro-4-iodo-phenyl)-3-phenyl-butyramide (prepared as described in example 56) (160 mg, 0.25 mmol) was dissolved in methanol (10 ml) and allowed to stir for 48 hours at ambient temperature followed by warming to 50° C. for an additional 6 hours. The solvent was removed in vacuo and the residue was then purified by super-critical fluid chromatography using a Chiracel OD column eluted with carbon dioxide at 100 bar and 30° C. containing 35% methanol in acetonitrile eluted at 2 mL/minute. The second eluted compound was collected and concentrated in vacuo to obtain (2S,3S)-2-{(S)-4-[4-((R)-2,3-dihydroxy-propoxy)-phenyl]-2,5-dioxo-imidazolidin-1-yl}-N-(2-fluoro-4-iodo-phenyl)-3-phenyl-butyramide as a colorless solid (35 mg, 44%). The compound eluted first was identical with (2S,3S)-2-{(R)-4-[4-((R)-2,3-dihydroxy-propoxy)-phenyl]-2,5-dioxo-imidazolidin-1-yl}-N-(2-fluoro-4-iodo-phenyl)-3-phenyl-butyramide.

HRMS: Obs Mass (M+H$^+$), 648.0995. Calcd. Mass, 648.1002 for $C_{28}H_{28}FIN_3O_6^+$.

LC-MS (reverse phase HPLC, C18 column, water/acetonitrile gradient): R$_t$=3.13 minutes, Obs. Mass (M+H$^+$), 648. Calcd. Mass, 648 for $C_{28}H_{28}FIN_3O_6^+$.

$^1$H NMR (DMSO-d$_6$, 300 MHz) δ$_H$ 10.18 (s, 1H), 8.57 (s, 1H), 4.84 (s, 1H) ppm (characteristic resonances).

EXAMPLE 58

(2S,3S)—N-(2-Fluoro-4-iodo-phenyl)-2-{(R)-4-[4-(2-hydroxy-1-hydroxymethyl-ethoxy)-phenyl]-2,5-dioxo-imidazolidin-1-yl}-3-phenyl-butyramide

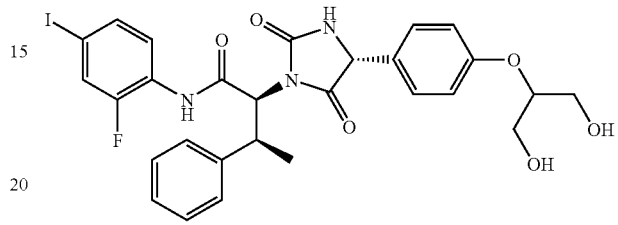

Prepared by the same method as described in example 1 except that (i) 2-fluoro-4-iodoaniline was used in place of 4-bromoaniline in step 2, (ii) (R)-tert-butoxycarbonylamino-[4-(2-hydroxy-1-hydroxymethyl-ethoxy)-phenyl]-acetic acid (prepared as described in example 160) was used in place of (R)-tert-butoxycarbonylamino-(4-methoxy-phenyl)-acetic acid in step 4, (iii) the diol functionality contained in (2S,3S)-2-{(R)-2-amino-2-[4-(2-hydroxy-1-hydroxymethyl-ethoxy)-phenyl]-acetylamino}-N-(2-fluoro-4-iodo-phenyl)-3-phenyl-butyramide was temporarily protected as the bis-trimethylsilyl ether (performed as described in example 114) prior to performing step 6, and (iv) acid catalyzed hydrolysis of (2S,3S)-2-{(R)-2,5-dioxo-4-[4-(2-trimethylsilanyloxy-1-trimethylsilanyloxymethyl-ethoxy)-phenyl]-imidazolidin-1-yl}-N-(2-fluoro-4-iodo-phenyl)-3-phenyl-butyramide was performed as described in example 114 prior to purification and isolation of (2S,3S)—N-(2-fluoro-4-iodo-phenyl)-2-{(R)-4-[4-(2-hydroxy-1-hydroxymethyl-ethoxy)-phenyl]-2,5-dioxo-imidazolidin-1-yl}-3-phenyl-butyramide in step 6.

HRMS: Obs Mass (M+H$^+$), 648.0991 Calcd. Mass, 648.1002 for $C_{28}H_{28}FIN_3O_6^+$.

EXAMPLE 59

(2S,3S)—N-(2-Fluoro-4-iodo-phenyl)-2-{(R)-4-[4-(3-methyl-oxetan-3-ylmethoxy)-phenyl]-2,5-dioxo-imidazolidin-1-yl}-3-phenyl-butyramide

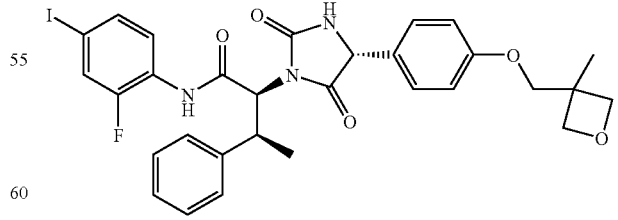

Prepared by the same method as described in example 48 except that (R)-tert-butoxycarbonylamino-[4-(3-methyl-oxetan-3-ylmethoxy)-phenyl]-acetic acid was used in place of (R)-tert-butoxycarbonylamino-{4-[2-(tetrahydro-pyran-2-yloxy)-ethoxy]-phenyl}-acetic acid. (R)-tert-Butoxycarbonylamino-[4-(3-methyl-oxetan-3-ylmethoxy)-phenyl]-acetic acid was prepared as described in example 48 except that 3-bromomethyl-3-methyl-oxetane was used in place of 2-(2-bromo-ethoxy)-tetrahydropyran.

HRMS: Obs Mass (M+H$^+$), 658.1202. Calcd. Mass, 658.1209 for $C_{30}H_{30}FIN_3O_5^+$.

EXAMPLE 60

(2R,3S)—N-(2-Fluoro-4-iodo-phenyl)-2-[(R)-4-(4-methylcarbamoylmethoxy-phenyl)-2,5-dioxo-imidazolidin-1-yl]-3-phenyl-butyramide

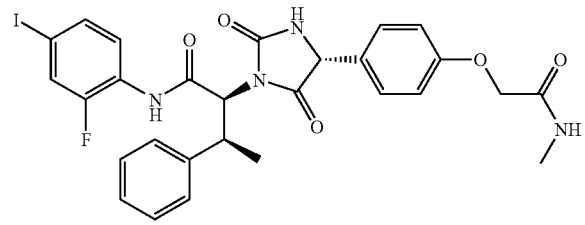

Prepared by the same method as described in example 48 except that (R)-tert-butoxycarbonylamino-(4-methylcarbamoylmethoxy-phenyl)-acetic acid was used in place of (R)-tert-butoxycarbonylamino-{4-[2-(tetrahydro-pyran-2-yloxy)-ethoxy]-phenyl}-acetic acid. (R)-tert-Butoxycarbonylamino-(4-methylcarbamoylmethoxy-phenyl)-acetic acid was prepared as described in example 48 except that 2-chloro-N-methyl-acetamide was used in place of 2-(2-bromo-ethoxy)-tetrahydropyran.

HRMS: Obs Mass (M+Na$^+$), 667.0820. Calcd. Mass, 667.0824 for $C_{28}H_{26}FIN_4NaO_5^+$.

EXAMPLE 61

(2S,3S)-2-{(R)-2,5-Dioxo-4-[4-(2-oxo-2-pyrrolidin-1-yl-ethoxy)-phenyl]-imidazolidin-1-yl}-N-(2-fluoro-4-iodo-phenyl)-3-phenyl-butyramide

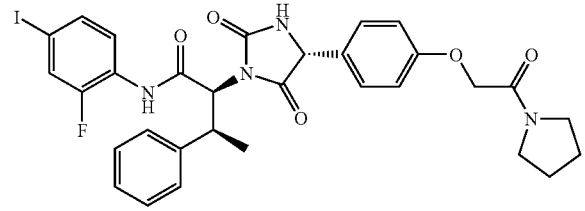

Prepared by the same method as described in example 48 except that (R)-tert-butoxycarbonylamino-[4-(2-oxo-2-pyrrolidin-1-yl-ethoxy)-phenyl]-acetic acid was used in place of (R)-tert-butoxycarbonylamino-{4-[2-(tetrahydro-pyran-2-yloxy)-ethoxy]-phenyl}-acetic acid. (R)-tert-butoxycarbonylamino-[4-(2-oxo-2-pyrrolidin-1-yl-ethoxy)-phenyl]-acetic acid was prepared by a method similar to that used for the preparation of (R)-tert-butyloxycarbonylamino-4-methoxyphenylglycine in example 1 except that 2-chloro-1-pyrrolidin-1-yl-ethanone was used in place of iodomethane.

LC-MS: Obs. Mass (M+H$^+$), 685/687. Calcd. Mass, 685/687 for $C_{31}H_{31}FIN_4O_5^+$.

EXAMPLE 62

(2S,3S)-2-[(R)-4-(4-{[Bis-(2-hydroxy-ethyl)-carbamoyl]-methoxy}-phenyl)-2,5-dioxo-imidazolidin-1-yl]-N-(2-fluoro-4-iodo-phenyl)-3-phenyl-butyramide

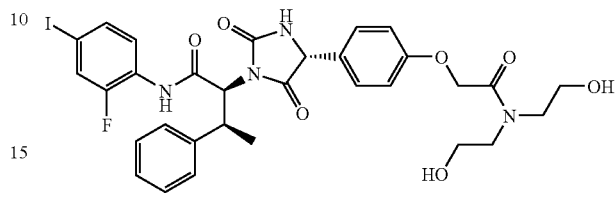

Prepared by the same method as described in example 48 except that (R)-[4-(2-{bis-[2-(tert-butyl-dimethyl-silanyloxy)-ethyl]-amino}-acetoxy)-phenyl]-tert-butoxycarbonylamino-acetic acid was used in place of (R)-tert-butoxycarbonylamino-{4-[2-(tetrahydro-pyran-2-yloxy)-ethoxy]-phenyl}-acetic acid. (R)-[4-(2-Bis-[2-(tert-butyl-dimethyl-silanyloxy)-ethyl]-amino(acetoxy)-phenyl]-tert-butoxycarbonylamino-acetic acid was prepared as described in example 48 except that N,N-bis-[2-(tert-butyl-dimethyl-silanyloxy)-ethyl]-2-chloro-acetamide was used in place of 2-(2-bromo-ethoxy)-tetrahydropyran.

HRMS: Obs Mass (M+Na$^+$), 741.1194. Calcd. Mass, 741.1192 for $C_{31}H_{32}FIN_4NaO_7^+$.

EXAMPLE 63

(4-{(R)-1-[(1S,2S)-1-(2-Fluoro-4-iodo-phenylcarbamoyl)-2-phenyl-propyl]-2,5-dioxo-imidazolidin-4-yl}-phenoxymethyl)-phosphonic acid dimethyl ester

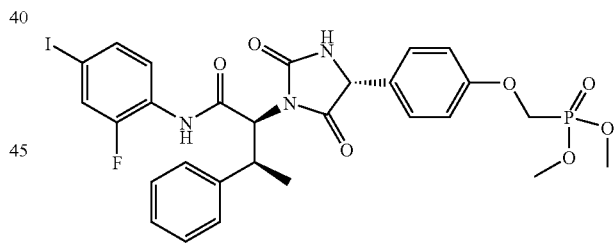

Prepared by the same method as described in example 48 except that R)-tert-butoxycarbonylamino-[4-(dimethoxy-phosphorylmethoxy)-phenyl]-acetic acid was used in place of (R)-tert-butoxycarbonylamino-{4-[2-(tetrahydro-pyran-2-yloxy)-ethoxy]-phenyl}-acetic acid. (R)-tert-Butoxycarbonylamino-[4-(dimethoxy-phosphorylmethoxy)-phenyl]-acetic acid was prepared as follows:

(1) Dimethyl phosphite (2.0 g, 18.2 mmol), paraformaldehyde (574 mg, 19.1 mmol) and triethylamine (0.25 mL, 1.8 mmol) were combined and heated to 70° C. to give a clear solution. After 1 hour the reaction was cooled and concentrated in vacuo overnight to afford the crude hydroxymethyl-phosphonic acid dimethyl ester (2.5 g).

(2) To a solution of hydroxymethyl-phosphonic acid dimethyl ester (2.0 g, 14.5 mmol) in anhydrous dichloromethane (50 mL) at −20° C. was added pyridine (1.4 mL, 16.7 mmol) followed by trifluoromethanesulfonic anhydride (2.7 mL, 15.9 mmol). After stirring at 0° C. for 0.5 hours, the mixture was filtered through celite with a thin layer of silica gel. The filtrate was washed with cold 1.0 N aqueous hydrochloric acid, water, saturated aqueous sodium bicarbonate and dried over sodium sulfate. The solvents were removed to give trifluoro-methanesulfonic acid dimethoxy-phosphorylmethyl ester as an oil (2.1 g, 53%).

(3) Sodium hydride (18.9 mg, 0.79 mmol) was added to (R)-tert-butoxycarbonylamino-(4-hydroxy-phenyl)-acetic acid (100 mg, 0.37 mmol) in anhydrous dimethylformamide (2.5 mL) in an ice bath. The mixture was allowed to warm to room temperature followed by the addition of trifluoro-methanesulfonic acid dimethoxy-phosphorylmethyl ester (122 mg, 0.45 mmol). Stirring was continued overnight at room temperature. The reaction was poured into 0.2 M aqueous hydrochloric acid (10 mL) and the mixture extracted with ethyl acetate. The combined extracts were washed with saturated aqueous sodium bicarbonate, brine and dried over sodium sulfate. Evaporation of the solvents gave tert-butoxycarbonylamino-[(R)-4-(dimethoxy-phosphorylmethoxy)-phenyl]-acetic acid (120 mg, 83% yield).

HRMS: Obs. Mass (M+H$^+$), 696.0766. Calcd. Mass, 696.0767 for $C_{28}H_{29}FIN_3O_7P^+$.

EXAMPLE 64

(4-{(R)-1-[(1S,2S)-1-(2-Fluoro-4-iodo-phenylcarbamoyl)-2-phenyl-propyl]-2,5-dioxo-imidazolidin-4-yl}-phenoxymethyl)-phosphonic acid

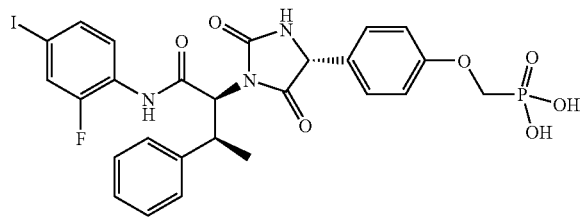

To a solution of (4-{(R)-1-[(1S,2S)-1-(2-fluoro-4-iodo-phenylcarbamoyl)-2-phenyl-propyl]-2,5-dioxo-imidazolidin-4-yl}-phenoxymethyl)-phosphonic acid dimethyl ester (prepared as described in example 63) (79 mg, 0.11 mmol) in dichloromethane (2.0 mL) was added bromotrimethylsilane (0.12 mL, 0.88 mmol) at room temperature. After 4 hours, the reaction was concentrated in vacuo and diluted with water (5 mL). The precipitated solids were filtered and dried to give (4-{(R)-1-[(1S,2S)-1-(2-fluoro-4-iodo-phenylcarbamoyl)-2-phenyl-propyl]-2,5-dioxo-imidazolidin-4-yl}-phenoxymethyl)-phosphonic acid (51 mg, 68%).

HRMS: Obs. Mass (M+H$^+$), 668.0453. Calcd. Mass, 668.0454 for $C_{26}H_{25}FIN_3O_7P^+$.

EXAMPLE 65

(2S,3S)—N-(2-Fluoro-4-iodo-phenyl)-2-((R)-4-isopropyl-2,5-dioxo-imidazolidin-1-yl)-3-phenyl-butyramide

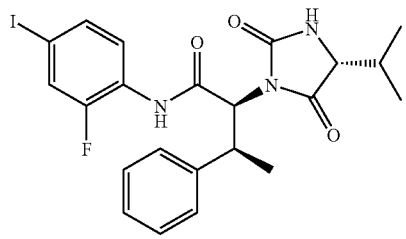

Prepared by the same method as described in example 48 except that (R)-2-tert-butoxycarbonylamino-3-methyl-butyric acid was used in place of (R)-tert-butoxycarbonylamino-{4-[2-(tetrahydro-pyran-2-yloxy)-ethoxy]-phenyl}-acetic acid.

HRMS: Obs. Mass (M+H$^+$), 524.0840. Calcd. Mass, 524.0841 for $C_{22}H_{24}FIN_3O_3^+$.

EXAMPLE 66

(2S,3S)-2-[4-(4-Cyclopropyl-phenyl)-2,5-dioxo-imidazolidin-1-yl]-N-(2-fluoro-4-iodo-phenyl)-3-phenyl-butyramide, isomer 1

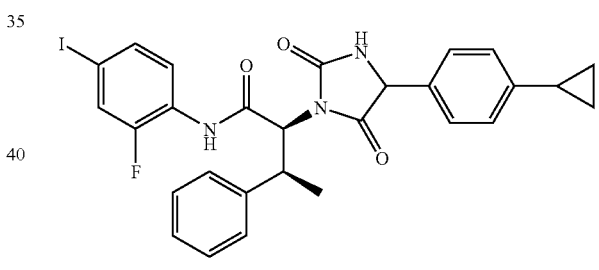

Prepared by the same method as described in example 48 except that tert-butoxycarbonylamino-(4-cyclopropyl-phenyl)-acetic acid was used in place of (R)-tert-butoxycarbonylamino-{4-[2-(tetrahydro-pyran-2-yloxy)-ethoxy]-phenyl}-acetic acid. tert-Butoxycarbonylamino-(4-cyclopropyl-phenyl)-acetic acid was prepared as follows:

(i) p-Cyclopropylbenzaldehyde (840 mg, 5.68 mmol) was dissolved in dry dichloromethane (2.5 mL) and treated with trimethylsilyl cyanide (756 mg, 7.394 mmol) and 5 crystals of zinc iodide and heated to 40° C. for 15 minutes. The reaction mixture was then concentrated in vacuo.

(ii) The concentrated orange solution from (i) was treated with 7N ammonia in methanol (7.1 mL, 14.22 mmol) and heated in a sealed tube under argon at 40° C. for 20 h. The solution was concentrated to a yellow residue (1.08 g).

(iii) The yellow residue from (ii) was dissolved in 6 N HCl$_{(aq)}$ (4.18 mL, 25.08 mmol) and heated at 100° C. for 5 h. The solution was concentrated to a volume of approximately 3 mL and titrated with concentrated NaOH$_{(aq)}$ to pH 8.0 to give a gummy residue (0.41 g).

(iv) The residue from (iii) was dissolved in 1 N aqueous sodium hydroxide (2.1 mL, 2.1 mmol), water (2.14 mL) and p-dioxane (7.1 mL) and cooled in an ice bath. To this mixture was added di-tert-butyidicarbonate (661 mg, 3.002 mmol) and the mixture stirred and allowed to warm to ambient temperature for 2 h. The solution was concentrated to remove p-dioxane, diluted with water (25 mL), washed with diethyl ether (3×25 mL) and back extracted with saturated aqueous sodium bicarbonate (25 mL). The combined aqueous layers were acidified to pH 2-3 with 1.5 N aqueous potassium hydrogen sulfate and extracted with ethyl acetate (3×50 mL). The combined organic extracts were dried over sodium sulfate, filtered and concentrated in vacuo to give tert-butoxycarbonylamino-(4-cyclopropyl-phenyl)-acetic acid (70 mg, 11% yield)

The diastereomers of (2S,3S)-2-[4-(4-cyclopropyl-phenyl)-2,5-dioxo-imidazolidin-1-yl]-N-(2-fluoro-4-iodo-phenyl)-3-phenyl-butyramide were separated by chromatography over silica gel gradient eluted from 5 to 20% v/v ethyl acetate in hexanes. Fractions containing the faster moving component were collected and concentrated in vacuo. The residue was precipitated from ether/hexanes to give (2S,3S)-2-[4-(4-cyclopropyl-phenyl)-2,5-dioxo-imidazolidin-1-yl]-N-(2-fluoro-4-iodo-phenyl)-3-phenyl-butyramide, isomer 1.

HRMS: Obs Mass (M+H$^+$), 598.0998. Calcd. Mass, 598.0998 for $C_{28}H_{26}FIN_3O_3^+$.

EXAMPLE 67

(2S,3S)-2-[(S)-4-(4-Cyclopropyl-phenyl)-2,5-dioxo-imidazolidin-1-yl]-N-(2-fluoro-4-iodo-phenyl)-3-phenyl-butyramide, isomer 2

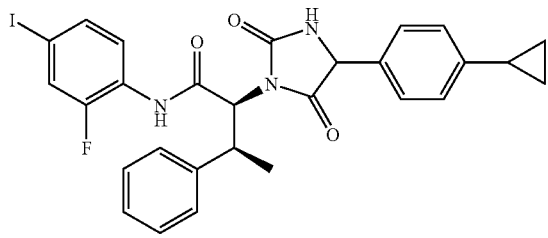

Prepared by the same method as described in example 66.

The diastereomers of (2S,3S)-2-[4-(4-cyclopropyl-phenyl)-2,5-dioxo-imidazolidin-1-yl]-N-(2-fluoro-4-iodo-phenyl)-3-phenyl-butyramide were separated by chromatography over silica gel gradient eluted from 5 to 20% v/v ethyl acetate in hexanes. Fractions containing the slower moving component were collected and concentrated in vacuo to give (2S,3S)-2-[4-(4-cyclopropyl-phenyl)-2,5-dioxo-imidazolidin-1-yl]-N-(2-fluoro-4-iodo-phenyl)-3-phenyl-butyramide, isomer 2.

HRMS: Obs Mass (M+H$^+$), 598.0994. Calcd. Mass, 598.0998 for $C_{28}H_{26}FIN_3O_3^+$.

EXAMPLE 68

(2S,3S)-2-((R)-4-Cyclohexyl-2,5-dioxo-imidazolidin-1-yl)-N-(2-fluoro-4-iodo-phenyl)-3-phenyl-butyramide

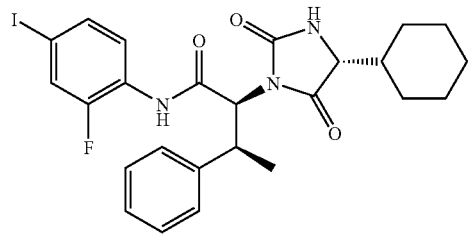

Prepared by the same method as described in example 48 except that (R)-tert-butoxycarbonylamino-cyclohexyl-acetic acid was used in place of (R)-tert-butoxycarbonylamino-{4-[2-(tetrahydro-pyran-2-yloxy)-ethoxy]-phenyl}-acetic acid.

HRMS: Obs Mass (M+H$^+$), 564.1156. Calcd. Mass, 564.1154 for $C_{25}H_{28}FIN_3O_3^+$.

EXAMPLE 69

(2S,3S)—N-(2-Fluoro-4-iodo-phenyl)-2-{4-[4-(2-methanesulfonyl-ethyl)-phenyl]-2,5-dioxo-imidazolidin-1-yl}-3-phenyl-butyramide, diastereomer 1

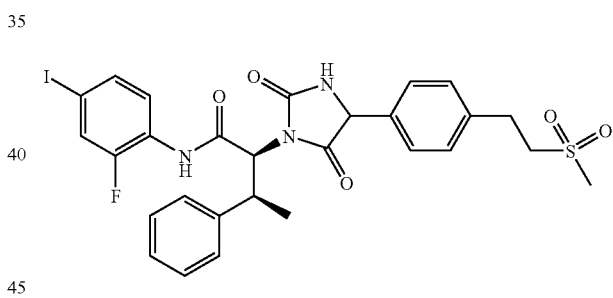

Prepared by the same method as described in example 1 except that (i) 2-fluoro-4-iodoaniline was used in place of 4-bromoaniline in step 2, (ii) tert-butoxycarbonylamino-[4-(2-methanesulfonyl-ethyl)-phenyl]-acetic acid (prepared as described below) was used in place of (R)-tert-butyloxycarbonylamino-4-methoxyphenylglycine in step 4, and (iii) super-critical fluid chromatography was used to separate the diastereomers of (2S,3S)—N-(2-fluoro-4-iodo-phenyl)-2-{4-[4-(2-methanesulfonyl-ethyl)-phenyl]-2,5-dioxo-imidazolidin-1-yl}-3-phenyl-butyramide after performing step 6. Super-critical fluid chromatography separation was performed using a Chiracel OJ column eluted with carbon dioxide at 100 bar and 30° C. modified with 25% ethanol in acetonitrile eluted at 2 mL/minute. The first eluted compound was collected and concentrated in vacuo to obtain (2S,3S)—N-(2-Fluoro-4-iodo-phenyl)-2-{4-[4-(2-methanesulfonyl-ethyl)-phenyl]-2,5-dioxo-imidazolidin-1-yl}-3-phenyl-butyramide, diastereomer 1.

Preparation of tert-butoxycarbonylamino-[4-(2-methanesulfonyl-ethyl)-phenyl]-acetic acid (1) To a mixture of amino-(4-bromo-phenyl)-acetic acid (543 mg, 2.4 mmol), triethylamine (822 μL, 5.9 mmol), 4-(dimethylamino)pyridine (29 mg, 0.24 mmol) in dioxane/water (2:1, 12 mL) was added di-tert-butyl dicarbonate (1.1 g, 5.0 mmol) and the resulting solution was allowed to stir for 3 hours. The reaction was diluted with ethyl acetate (50 ml), washed with 0.2 N aqueous hydrochloric acid (10 mL), water (20 mL), brine and the organic layer was dried over sodium sulfate and filtered. The solvent was removed in vacuo to give (4-bromo-phenyl)-tert-butoxycarbonylamino-acetic acid (780 mg, 100%)

(2) (4-Bromo-phenyl)-tert-butoxycarbonylamino-acetic acid (780 mg, 2.4 mmol) was dissolved in N,N-dimethylformamide (15 mL) and to this was added potassium hydrogen carbonate (260 mg, 2.6 mmol) followed by benzyl bromide (281 μL, 2.4 mmol) and stirring continued at ambient temperature for 6 hours. The reaction was poured into water (50 mL) and extracted with ethyl acetate (2×60 mL). The organic extracts were washed with water (2×20 mL), brine, dried over sodium sulfate and filtered through a layer of silica gel. The filtrate was concentrated in vacuo and the residue crystallized from 100% hexane to give (4-bromo-phenyl)-tert-butoxycarbonylamino-acetic acid benzyl ester (500 mg, 50%).

(3) (4-Bromo-phenyl)-tert-butoxycarbonylamino-acetic acid benzyl ester (1.5 g, 3.6 mmol), methyl vinyl sulfone (406 μL, 4.6 mmol), palladium(II) acetate (80 mg, 10 mol %), tri-o-tolylphosphine (217 mg, 20 mol %) and triethylamine (2.0 ml, 14.3 mmol) were combined in acetonitrile (18 mL), degassed and refluxed for 8 hours. Additional palladium(II) acetate (80 mg, 10 mol %) and tri-o-tolylphosphine (217 mg, 20 mol %) were added and refluxing continued overnight. The reaction was cooled, solvent removed in vacuo and the residue was purified by chromatography over silica gel gradient eluted from 20 to 90% v/v ethyl acetate in hexane to afford tert-butoxycarbonylamino-[4-((E)-2-methanesulfonyl-vinyl)-phenyl]-acetic acid benzyl ester (1.2 g, 75%).

(4) A hydrogenation vessel containing tert-butoxycarbonylamino-[4-((E)-2-methanesulfonyl-vinyl)-phenyl]-acetic acid benzyl ester (1.1 g, 2.5 mmol) in methanol/ethyl acetate (3:1, 50 ml) was purged with nitrogen and 10% palladium on carbon (200 mg) added. The atmosphere above the organic solution was exchanged for hydrogen and the reaction mixture stirred vigorously for 3 hours at ambient temperature. The reaction mixture was filtered through a pad of Celite and concentrated in vacuo to give tert-butoxycarbonylamino-[4-(2-methanesulfonyl-ethyl)-phenyl]-acetic acid (800 mg, 94%).

HRMS: Obs Mass (M+H$^+$), 664.0778. Calcd. Mass, 664.0773 for $C_{28}H_{28}FIN_3O_5S^+$.

$^1$H NMR (DMSO-d$_6$, 300 MHz) δ$_H$ 10.11 (s, 1H), 8.56 (s, 1H), 5.02 (d, J=11.7 Hz, 1H), 4.41 (s, 1H). ppm (characteristic resonances).

EXAMPLE 70

(2S,3S)—N-(2-Fluoro-4-iodo-phenyl)-2-{4-[4-(2-methanesulfonyl-ethyl)-phenyl]-2,5-dioxo-imidazolidin-1-yl}-3-phenyl-butyramide, diastereomer 2

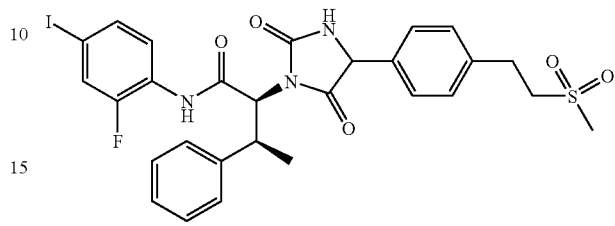

Prepared as described in example 69 except that the second eluted compound was collected and concentrated in vacuo to obtain (2S,3S)—N-(2-Fluoro-4-iodo-phenyl)-2-{4-[4-(2-methanesulfonyl-ethyl)-phenyl]-2,5-dioxo-imidazolidin-1-yl}-3-phenyl-butyramide, diastereomer 2.

HRMS: Obs Mass (M+H$^+$), 664.0763. Calcd. Mass, 664.0773 for $C_{28}H_{28}FIN_3O_5S^+$.

LC-MS:

$^1$H NMR (DMSO-d$_6$, 300 MHz) δ$_H$ 10.18 (s, 1H), 8.61 (s, 1H), 4.93 (s, 1H), 4.87 (d, J=11.4 Hz, 1H) ppm (characteristic resonances).

EXAMPLE 71

(2S,3S)—N-(2,6-Difluoro-4-iodo-phenyl)-2-{(R)-4-[4-(2-methoxy-ethoxy)-phenyl]-2,5-dioxo-imidazolidin-1-yl}-3-phenyl-butyramide

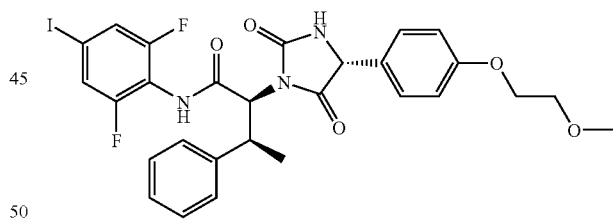

Prepared by the same method as described in example 48 except that (i) 2,6-difluoro-4-iodoaniline was used in place of 2-fluoro-4-iodoaniline, and (ii) (R)-tert-butoxycarbonylamino-[4-(2-methoxy-ethoxy)-phenyl]-acetic acid was used in place of (R)-tert-butoxycarbonylamino-{4-[2-(tetrahydropyran-2-yloxy)-ethoxy]-phenyl}-acetic acid. (R)-tert-Butoxycarbonylamino-[4-(2-methoxy-ethoxy)-phenyl]-acetic acid was prepared as described in example 48 except that 1-bromo-2-methoxyethane was used in place of 2-(2-bromoethoxy)-tetrahydropyran.

HRMS: Obs Mass (M+H$^+$), 650.0952. Calcd. Mass, 650.0958 for $C_{28}H_{27}F_2, N_3O_5^+$.

EXAMPLE 72

(S)—N-(2-Fluoro-4-iodo-phenyl)-2-{(R)-4-[4-(2-hydroxy-ethoxy)-phenyl]-2,5-dioxo-imidazolidin-1-yl}-3-thiophen-2-yl-propionamide

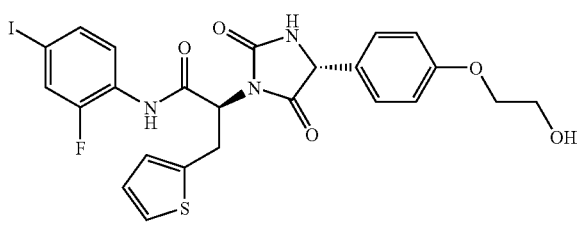

Prepared by the same method as described in example 48 except that (i) step 1 was performed as described below and (ii) O-benzotriazol-1-yl-N,N,N,N'-bis(tetramethylene)uronium hexaflurorophosphate was used as the coupling reagent in place of O-benzotriazol-1-yl-N,N,N',N'-tetramethyluronium hexaflurorophosphate in step 4.

Step 1: To a solution of (S)-2-tert-butoxycarbonylamino-3-thiophen-2-yl-propionic acid (1.1 g, 4.06 mmol) and 2-fluoro-4-iodoaniline (800 mg, 3.38 mmol) in pyridine (15 mL) at −10° C. was slowly added phosphorus oxychloride (0.35 mL, 3.72 mmol) under an atmosphere of dry nitrogen. The mixture was stirred for 2 hours at −10° C. After removal of the solvent and the excess reagent by rotary evaporator, ice water was added. The mixture was extracted with dichloromethane and the organic layer washed with 1 M aqueous citric acid, brine, saturated aqueous sodium carbonate, brine and dried over sodium sulfate. The solvents were removed to give [(S)-1-(2-fluoro-4-iodo-phenylcarbamoyl)-2-thiophen-2-yl-ethyl]-carbamic acid tert-butyl ester as a yellow viscous oil for use in the next step (1.52 g, 92%).

LC-MS: Obs Mass (M+H$^+$), 491. Calcd. Mass, 491 for $C_{18}H_{20}FIN_2O_3S^+$.

LC-MS: Obs Mass (M+H$^+$), 610; Calcd. Mass, 610 for $C_{24}H_{22}FIN_3O_5S^+$.

EXAMPLE 73

(S)-3-(5-Bromo-thiophen-2-yl)-N-(2-fluoro-4-iodo-phenyl)-2-{(R)-4-[4-(2-hydroxy-ethoxy)-phenyl]-2,5-dioxo-imidazolidin-1-yl}-propionamide

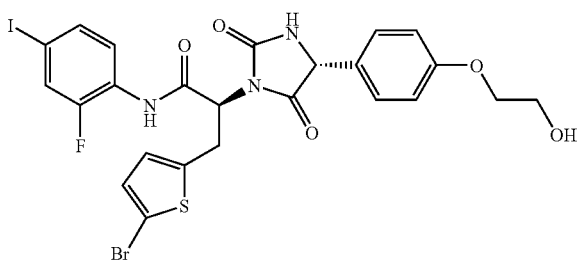

Prepared by the same method as described in example 72 except that (S)-3-(5-bromo-thiophen-2-yl)-2-tert-butoxycarbonylamino-propionic acid was used in place of (S)-2-tert-butoxycarbonylamino-3-thiophen-2-yl-propionic acid in step 1.

LC-MS: Obs Mass (M+H$^+$), 688; Calcd. Mass, 688 for $C_{24}H_{21}BrFIN_3O_5S^+$.

EXAMPLE 74

(S)-2-{(R)-4-[4-((R)-2,3-Dihydroxy-propoxy)-phenyl]-2,5-dioxo-imidazolidin-1-yl}-N-(2-fluoro-4-iodo-phenyl)-3-thiophen-2-yl-propionamide

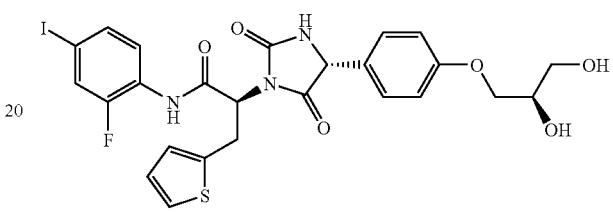

Prepared by the same method as described in example 114 except that (i) step 1 was performed as described in example 72 and (ii) O-benzotriazol-1-yl-N,N,N',N'-bis(tetramethylene)uronium hexaflurorophosphate was used as the coupling reagent in place of O-benzotriazol-1-yl-N,N,N',N'-tetramethyluronium hexaflurorophosphate in step 4.

LC-MS: Obs Mass (M+H$^+$), 640; Calcd. Mass, 640 for $C_{25}H_{24}FIN_3O_6S^+$.

EXAMPLE 75

(S)-3-(5-Bromo-thiophen-2-yl)-2-{(R)-4-[4-((R)-2,3-dihydroxy-propoxy)-phenyl]-2,5-dioxo-imidazolidin-1-yl}-N-(2-fluoro-4-iodo-phenyl)-propionamide

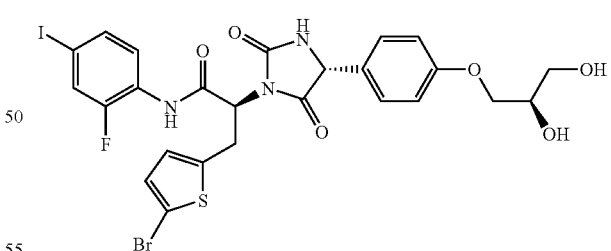

Prepared by the same method as described in example 114 except that (i) step 1 was performed as described in example 73 and (ii) Q-benzotriazol-1-yl-N,N,N',N'-bis(tetramethylene)uronium hexaflurorophosphate was used as the coupling reagent in place of O-benzotriazol-1-yl-N,N,N',N'-tetramethyluronium hexaflurorophosphate in step 4.

LC-MS: Obs Mass (M+H$^+$), 718; Calcd. Mass, 718 for $C_{25}H_{23}BrFIN_3O_6S^+$.

EXAMPLE 76

(S)—N-(2-Fluoro-4-iodo-phenyl)-2-{(R)-4-[4-(2-hydroxy-ethoxy)-phenyl]-2,5-dioxo-imidazolidin-1-yl}-3-pyridin-2-yl-propionamide

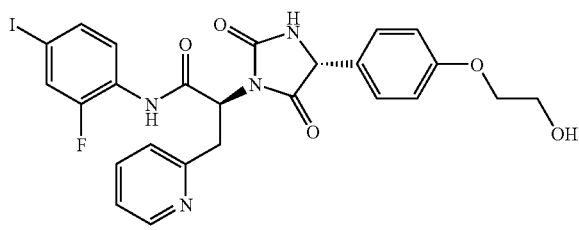

Prepared by the same method as described in example 43 except that (i) (S)-2-tert-butoxycarbonylamino-3-pyridin-2-yl-propionic acid was used in place of (S)-2-(9H-fluoren-9-ylmethoxycarbonylamino)-3-naphthalen-2-yl-propionic acid in step 1 and (ii) step 3 was performed as described below.

Step 3: To a solution of (S)-[1-(2-fluoro-4-iodo-phenylcarbamoyl)-2-pyridin-2-yl-ethyl]-carbamic acid tert-butyl ester (1.2 g, 2.47 mmol) in dichloromethane (5 mL) at 0° C. was added trifluoroacetic acid (5 mL) and the mixture stirred at 0° C. for 1 hour. The reaction mixture was concentrated in vacuo and the residue suspended in ice cold water. The aqueous suspension was neutralized with saturated aqueous sodium carbonate solution to basic then extracted with dichloromethane (three times). The combined organic extracts were dried over sodium sulfate, filtered and concentrated in vacuo. The residue was purified by chromatography over silica gel gradient eluted from 100% hexane up to 100% ethyl acetate in 40 minutes. Concentration of the product containing fractions gave (S)-2-amino-N-(2-fluoro-4-iodo-phenyl)-3-pyridin-2-yl-propionamide as a yellow solid (806 mg, 85%).

LC-MS: Obs Mass (M+H$^+$), 386; Calcd. Mass, 386 for $C_{14}H_{13}FIN_3O^+$.

LC-MS: Obs Mass (M+H$^+$), 605; Calcd. Mass, 605 for $C_{25}H_{23}FIN_4O_5^+$.

EXAMPLE 77

(S)—N-(2-Fluoro-4-iodo-phenyl)-2-{(R)-4-[4-(2-hydroxy-ethoxy)-phenyl]-2,5-dioxo-imidazolidin-1-yl}-3-(1-oxy-pyridin-2-yl)-propionamide

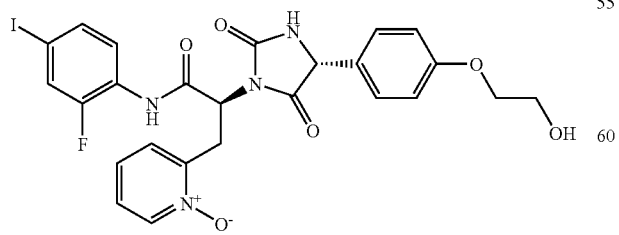

To a solution of (S)—N-(2-fluoro-4-iodo-phenyl)-2-{(R)-4-[4-(2-hydroxy-ethoxy)-phenyl]-2,5-dioxo-imidazolidin-1-yl}-3-pyridin-2-yl-propionamide (prepared as described in example 76) (50 mg, 0.083 mmol) in dichloromethane (4 mL) was added 3-chloroperbenzoic acid (77%, 28 mg, 0.12 mmol) and the mixture stirred for 5 hours. The reaction mixture was concentrated in vacuo and the residue was purified by chromatography over silica gel gradient eluted from 100% dichloromethane up to 10% methanol/90% dichloromethane in 30 minutes. Concentration of the product containing fractions gave (S)—N-(2-fluoro-4-iodo-phenyl)-2-{(R)-4-[4-(2-hydroxy-ethoxy)-phenyl]-2,5-dioxo-imidazolidin-1-yl}-3-(1-oxy-pyridin-2-yl)-propionamide as a white solid (40 mg, 78%).

LC-MS: Obs Mass (M+H$^+$), 621; Calcd. Mass, 621 for $C_{25}H_{23}FIN_4O_6^+$.

EXAMPLE 78

(S)-2-{(R)-4-[4-((R)-2,3-Dihydroxy-propoxy)-phenyl]-2,5-dioxo-imidazolidin-1-yl}-N-(2-fluoro-4-iodo-phenyl)-3-pyridin-2-yl-propionamide

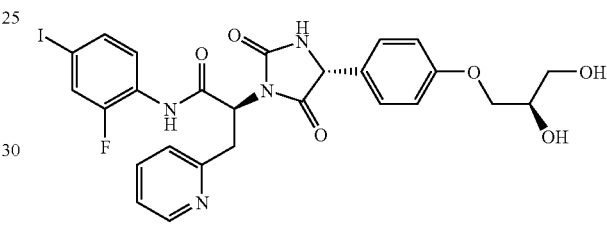

Prepared by the same method as described in example 114 except that (i) steps 1-3 were performed as described in example 76 and (ii) O-benzotriazol-1-yl-N,N,N',N'-bis(tetramethylene)uronium hexaflurorophosphate was used as the coupling reagent in place of O-benzotriazol-1-yl-N,N,N',N'-tetramethyluronium hexaflurorophosphate in step 4.

LC-MS: Obs Mass (M+H$^+$), 635. Calcd. Mass, 635 for $C_{26}H_{25}FIN_4O_6^+$.

EXAMPLE 79

(S)—N-(2-Fluoro-4-iodo-phenyl)-2-{(R)-4-[4-(2-hydroxy-ethoxy)-phenyl]-2,5-dioxo-imidazolidin-1-yl}-3-thiazol-4-yl-propionamide

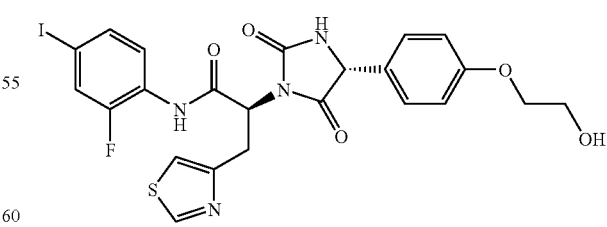

Prepared by the same method as described in example 1 except that 2-fluoro-4-iodoaniline was used in place of 4-bromoaniline and (S)-2-tert-butoxycarbonylamino-3-thiazol-4-yl-propionic acid was used in place of (2S,3S)-2-tert-butoxycarbonylamino-3-phenyl-butyric acid in step 2 and (R)-tertbutoxycarbonylamino-{4-[2-(tetrahydro-pyran-2-yloxy)-ethoxy]-phenyl}-acetic acid was used in place of (R)-tert-butoxycarbonylamino[4-methoxy-phenyl]-acetic acid in step 4. (R)-tert-Butoxycarbonylamino-{4-[2-(tetrahydro-pyran-2-yloxy)-ethoxy]-phenyl}-acetic acid was prepared as described in example 48.

HRMS: Obs Mass (M+H$^+$), 611.0253. Calcd. Mass, 611.0256 for $C_{23}H_{21}FIN_4O_5S^+$.

EXAMPLE 80

(S)—N-(2-Fluoro-4-iodo-phenyl)-2-{(R)-4-[4-(2-methoxy-ethoxy)-phenyl]-2,5-dioxo-imidazolidin-1-yl}-3-thiazol-4-yl-propionamide

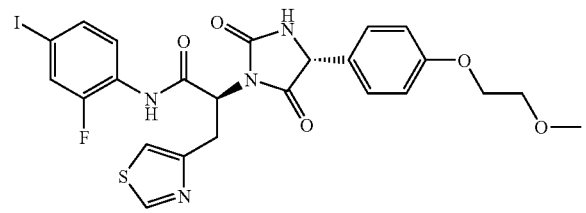

Prepared by the same method as described in example 79 except that (R)-tert-butoxycarbonylamino-[4-(2-methoxy-ethoxy)-phenyl]-acetic acid was used in place of (R)-tert-butoxycarbonylamino-{4-[2-(tetrahydro-pyran-2-yloxy)-ethoxy]-phenyl}-acetic acid. (R)-tert-Butoxycarbonylamino-[4-(2-methoxy-ethoxy)-phenyl]-acetic acid was prepared as described in example 48 except that 1-bromo-2-methoxyethane was used in place of 2-(2-bromo-ethoxy)-tetrahydropyran.

HRMS: Obs Mass (M+H$^+$), 625.0403. Calcd. Mass, 625.0413 for $C_{24}H_{23}FIN_4O_5S^+$.

EXAMPLE 81

(S)—N-(2-Fluoro-4-iodo-phenyl)-2-{(R)-4-[4-(2-hydroxy-ethoxy)-phenyl]-2,5-dioxo-imidazolidin-1-yl}-3-(3-methyl-3H-imidazol-4-yl)-propionamide

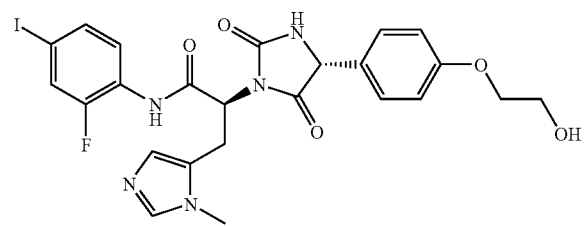

Prepared by the same method as described in example 3 except that (i) 2-fluoro-4-iodoaniline used in place of 2-chloro-4-bromoaniline, and (ii) (2S)-2-tert-butoxycarbonylamino-3-(3-methyl-3H-imidazol-4-yl)-propionic acid used in place of (2S,3S)-2-tert-butoxycarbonylamino-3-phenyl-butyric acid in step 1.

HRMS: Obs Mass (M+H$^+$), 608.0798. Calcd. Mass, 608.0801 for $C_{24}H_{24}FIN_5O_5^+$.

EXAMPLE 82

N-(2-Fluoro-4-iodo-phenyl)-2-{(R)-4-[4-(2-hydroxy-ethoxy)-phenyl]-2,5-dioxo-imidazolidin-1-yl}-acetamide

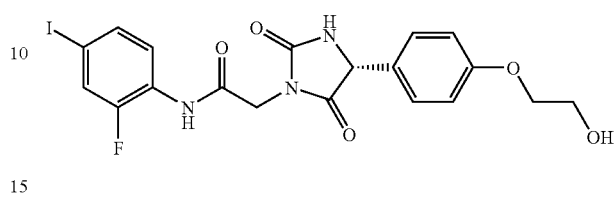

Prepared by the same method as described in example 48 except that tert-butoxycarbonylamino-acetic acid was used in place of (2S,3S)-2-tert-butoxycarbonylamino-3-phenyl-butyric acid.

HRMS: Obs Mass (M+Na$^+$), 536.0088. Calcd. Mass 536.0089 for $C_{19}H_{17}FIN_3NaO_5^+$.

EXAMPLE 83

(S)—N-(2-Fluoro-4-iodo-phenyl)-2-{(R)-4-[4-(2-hydroxy-ethoxy)-phenyl]-2,5-dioxo-imidazolidin-1-yl}-3-methyl-butyramide

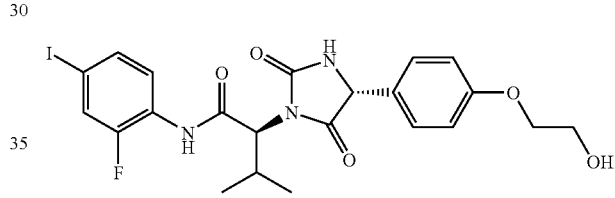

Prepared by the same method as that described in example 48 except that (S)-2-tert-butoxycarbonylamino-3-methyl-butyric acid was used in place of (2S,3S)-2-tert-butoxycarbonylamino-3-phenyl-butyric acid in step 1.

LC-MS: Obs. Mass, 556. Calcd. Mass, 556 for $C_{22}H_{24}FIN_3O_5^+$.

EXAMPLE 84

(S)—N-(2-Fluoro-4-iodo-phenyl)-2-{(R)-4-[4-(2-methoxy-ethoxy)-phenyl]-2,5-dioxo-imidazolidin-1-yl}-3-methyl-butyramide

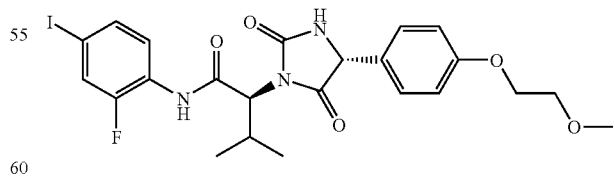

Prepared by the same method as described in example 21 except that (i) (S)-2-tert-butoxycarbonylamino-3-methyl-butyric acid was used in place of (S)-2-tert-butoxycarbonylamino-3-phenyl-propionic acid in step 1, and (ii) O-benzotriazol-1-yl-N,N,N',N'-bis(tetramethylene)uronium hexaflurorophosphate was used as the coupling reagent in place of O-benzotriazol-1-yl-N,N,N',N'-tetramethyluronium hexaflurorophosphate in step 4.

LC-MS: Obs Mass (M+H$^+$), 570. Calcd. Mass, 570 for $C_{23}H_{26}FIN_3O_5^+$.

EXAMPLE 85

(S)-2-{(R)-4-[4-((R)-2,3-Dihydroxy-propoxy)-phenyl]-2,5-dioxo-imidazolidin-1-yl}-N-(2-fluoro-4-iodo-phenyl)-3-methyl-butyramide

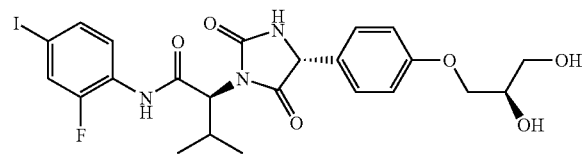

Prepared by the same method as described in example 114 except that (i) step 1 was performed as described in example 83, and (ii) O-benzotriazol-1-yl-N,N,N',N'-bis(tetramethylene)uronium hexaflurorophosphate was used as the coupling reagent in place of O-benzotriazol-1-yl-N,N,N',N'-tetramethyluronium hexaflurorophosphate in step 4.

LC-MS: Obs Mass (M+H$^+$), 586. Calcd. Mass, 586 for $C_{23}H_{26}FIN_3O_6^+$.

EXAMPLE 86

(S)—N-(2-Fluoro-4-iodo-phenyl)-3-methyl-2-{4-[4-(2-morpholin-4-yl-ethoxy)-phenyl]-2,5-dioxo-imidazolidin-1-yl}-butyramide; compound with acetic acid

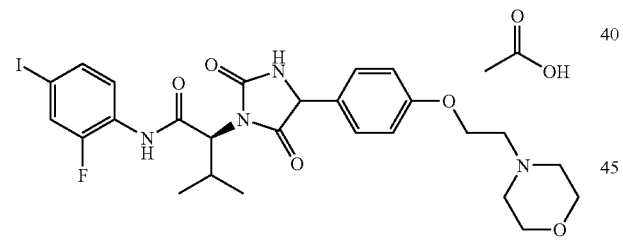

Prepared by the same method as described in example 1 except that (i) (S)-2-tert-butoxycarbonylamino-3-methyl-butyric acid was used in place of (2S,3S)-2-tert-butoxycarbonylamino-3-phenyl-butyric acid in step 1, (ii) 2-fluoro-4-iodoaniline was used in place of 4-bromoaniline in step 2, and (iii) (R,S)-tert-butoxycarbonylamino-[4-(2-morpholin-4-yl-ethoxy)-phenyl]-acetic acid was used in place of (R)-tert-butyloxycarbonylamino-4-methoxyphenylglycine in step 4. (R,S)-tert-Butoxycarbonylamino-[4-(2-morpholin-4-yl-ethoxy)-phenyl]-acetic acid was prepared as follows:

(1) To a solution of (R)-tert-butoxycarbonylamino-[4-(2-hydroxy-ethoxy)-phenyl]-acetic acid (1.0 g, 3.21 mmol) in methanol (10 mL) was added a catalytic amount of concentrated sulfuric acid. The reaction mixture was stirred at reflux for 3 hours. The solvent was evaporated and the crude (R)-tert-butoxycarbonylamino-[4-(2-hydroxy-ethoxy)-phenyl]-acetic acid methyl ester (0.836 g, 80% yield) was carried on to the next step without further purification.

(2) To a stirred solution of (R)-tert-butoxycarbonylamino-[4-(2-hydroxy-ethoxy)-phenyl]-acetic acid methyl ester (80 mg, 0.25 mmol) in pyridine (1.5 mL) was added methanesulfonyl chloride (0.023 mL, 0.30 mmol) dropwise. The reaction mixture was stirred at room temperature for 3 hours. The solvent was evaporated and the crude product was purified by chromatography over silica gel eluted with 3:1 v/v hexanes/ethyl acetate to give (R)-tert-butoxycarbonylamino-[4-(2-methanesulfonyloxy-ethoxy)-phenyl]-acetic acid methyl ester (50 mg, 50% yield) as a colorless oil.

(3) To a stirred solution of (R)-tert-butoxycarbonylamino-[4-(2-methanesulfonyloxy-ethoxy)-phenyl]-acetic acid methyl ester (50 mg, 0.12 mmol) in ethanol (1 mL) was added morpholine (0.043 mL, 0.49 mmol) at room temperature. The reaction mixture was refluxed for 1 hour. The solvent was evaporated and the crude product was purified by chromatography over silica gel eluted with 1:1 v/v hexanes/ethyl acetate to give (R)-tert-butoxycarbonylamino-[4-(2-morpholin-4-yl-ethoxy)-phenyl]-acetic acid methyl ester (45 mg, 92% yield) as a colorless oil.

(4) To a stirred solution of (R)-tert-butoxycarbonylamino-[4-(2-morpholin-4-yl-ethoxy)-phenyl]-acetic acid methyl ester (45 mg, 0.11 mmol) in methanol (0.6 mL) and water (0.2 mL) was added lithium hydroxide monohydrate (14.3 mg, 0.34 mmol) at room temperature. The reaction mixture was stirred at room temperature for 3 hours. The solvent was evaporated and the crude product (R,S)-tert-butoxycarbonylamino-[4-(2-morpholin-4-yl-ethoxy)-phenyl]-acetic acid (43 mg, 99% yield) was carried on to the next step without further purification.

HRMS: Obs Mass (M+H$^+$), 625.1318. Calcd. Mass, 625.1318 for $C_{26}H_{31}FIN_4O_5^+$.

EXAMPLE 87

(S)—N-(2-Fluoro-4-iodo-phenyl)-3-methyl-2-(4-{4-[2-(4-methyl-piperazin-1-yl)-ethoxy]-phenyl}-2,5-dioxo-imidazolidin-1-yl)-butyramide; compound with acetic acid

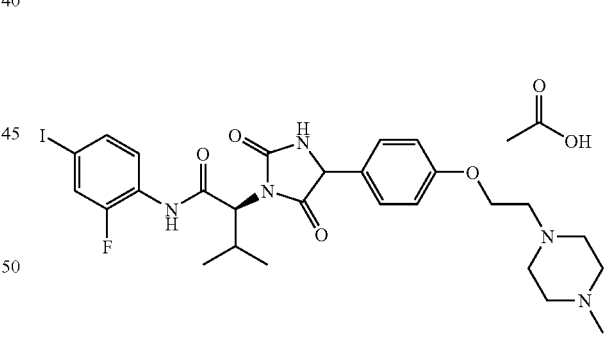

Prepared by the same method as described in example 86 except that (i) (R,S)-tert-butoxycarbonylamino-{4-[2-(4-methyl-piperazin-1-yl)-ethoxy]-phenyl}-acetic acid was used in place of (R,S)-tert-butoxycarbonylamino-[4-(2-morpholin-4-yl-ethoxy)-phenyl]-acetic acid in step 4. (R,S)-tert-Butoxycarbonylamino-{4-[2-(4-methyl-piperazin-1-yl)-ethoxy]-phenyl}-acetic acid was prepared using the same method as described for (R,S)-tert-butoxycarbonylamino-[4-(2-morpholin-4-yl-ethoxy)-phenyl]-acetic acid in example 86 except that 1-methyl-piperazine was used in place of morpholine in step 3.

HRMS: Obs Mass (M+H$^+$), 638.1633. Calcd. Mass, 638.1637 for $C_{27}H_{34}FIN_5O_4^+$.

EXAMPLE 88

(S)-2-(2,5-Dioxo-4-pyridin-3-yl-imidazolidin-1-yl)-N-(2-fluoro-4-iodo-phenyl)-3-methyl-butyramide

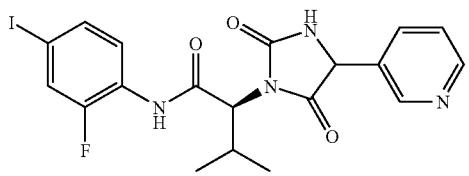

Prepared by the same method as described in example 1 except that (i) (S)-2-tert-butoxycarbonylamino-3-methyl-butyric acid was used in place of (2S,3S)-2-tert-butoxycarbonylamino-3-phenyl-butyric acid in step 1, (ii) 2-fluoro-4-iodoaniline was used in place of 4-bromoaniline in step 2, and (iii) (R,S)-tert-butoxycarbonylamino-pyridin-3-yl-acetic acid was used in place of (R)-tert-butyloxycarbonylamino-4-methoxyphenylglycine in step 4.

HRMS: Obs Mass (M+H$^+$), 497.0476. Calcd. Mass, 497.0481 for $C_{19}H_{19}FIN_4O_3^+$.

EXAMPLE 89

4,4,4-Trifluoro-N-(2-fluoro-4-iodo-phenyl)-2-{(R)-4-[4-(2-hydroxy-ethoxy)-phenyl]-2,5-dioxo-imidazolidin-1-yl}-3-methyl-butyramide

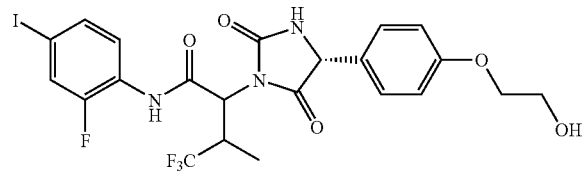

Prepared by the same method as described in example 72 except that (±)-2-tert-butoxycarbonylamino-4,4,4-trifluoro-3-methyl-butyric was used in place of (S)-2-tert-butoxycarbonylamino-3-thiophen-2-yl-propionic acid in step 1.

LC-MS: Obs Mass (M+H$^+$), 610. Calcd. Mass, 610 for $C_{22}H_{21}F_4IN_3O_5^+$.

EXAMPLE 90

(2S,3S)-2-{(R)-4-[4-((R)-2,3-Dihydroxy-propoxy)-phenyl]-2,5-dioxo-imidazolidin-1-yl}-3-methyl-pentanoic acid (2-fluoro-4-iodo-phenyl)-amide

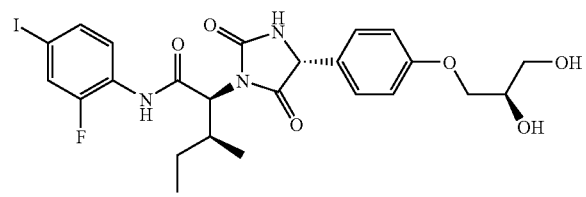

Prepared by the same method as described in example 74 except (2S,3S)-2-tert-butoxycarbonylamino-3-methyl-propionic acid was used in place of (S)-2-tert-butoxycarbonylamino-3-thiophen-2-yl-propionic acid in step 1.

LC-MS: Obs Mass (M+H$^+$), 600. Calcd. Mass, 600 for $C_{24}H_{28}FIN_3O_6^+$.

EXAMPLE 91

4,4,4-Trifluoro-N-(2-fluoro-4-iodo-phenyl)-2-(R)-4-[4-(2-hydroxy-ethoxy)-phenyl]-2,5-dioxo-imidazolidin-1-yl)-3-trifluoromethyl-butyramide

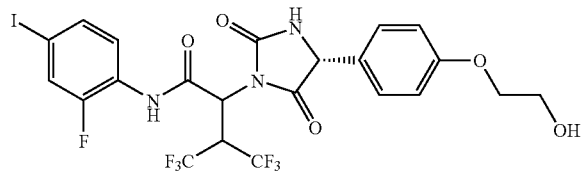

Prepared by the same method as described in example 72 except that (±)-2-tert-butoxycarbonyl-amino-4,4,4-trifluoro-3-trifluoromethyl-butyric acid was used in place of (S)-2-tert-butoxycarbonylamino-3-thiophen-2-yl-propionic acid in step 1. 2-tert-Butoxycarbonyl-amino-4,4,4-trifluoro-3-trifluoromethyl-butyric acid was prepared as described below.

Preparation of 2-tert-butoxycarbonyl-amino-4,4,4-trifluoro-3-trifluoromethyl-butyric acid To a solution of 4,4,4,4',4',4'-hexafluoro-DL-valine (1.0 g, 4.4 mmol) and sodium carbonate (933 mg, 8.8 mmol) in dioxane (10 mL) and water (10 mL) at 0° C. was slowly added di-tert-butyidicarbonate. After addition, the mixture was stirred for 12 hours at room temperature. The reaction mixture was partitioned between water and ethyl acetate and the organic layer was discarded. The organic layer was adjusted to pH >4 with 1 M aqueous citric acid solution, washed with brine, dried over sodium sulfate and concentrated to give 2-tert-butoxycarbonyl-amino-4,4,4-trifluoro-3-trifluoromethyl-butyric acid as a yellow solid (1.34 g, 96%).

LC-MS: Obs Mass (M–H$^+$)=324; Calcd. Mass, 324 for $C_{10}H_{12}F_6NO_4^-$.

LC-MS: Obs Mass (M+H$^+$)=664; Calcd. Mass, 664 for $C_{22}H_{18}F_7IN_3O_5^+$.

EXAMPLE 92

(S)—N-(2-Fluoro-4-iodo-phenyl)-2-{(R)-4-[4-(2-hydroxy-ethoxy)-phenyl]-2,5-dioxo-imidazolidin-1-yl}-3,3-dimethyl-butyramide

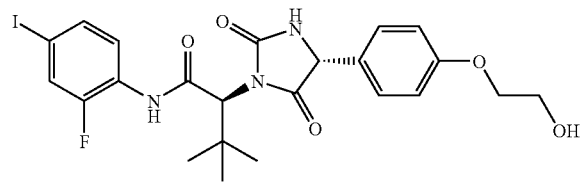

Prepared by the same method as described in example 43 except that (S)-2-(9H-fluoren-9-ylmethoxycarbonylamino)-3,3-dimethyl-2-yl-butyric acid was used in place of (S)-2-(9H-fluoren-9-ylmethoxycarbonylamino)-3-naphthalen-2-yl-propionic acid in step 1.

LC-MS: Obs Mass (M+H$^+$), 570. Calcd. Mass, 570 for $C_{23}H_{26}FIN_3O_5^+$.

EXAMPLE 93

(S)-2-{(R)-4-[4-(2-Hydroxy-ethoxy)-phenyl]-2,5-dioxo-imidazolidin-1-yl}-4,4-dimethyl-pentanoic acid (2-fluoro-4-iodo-phenyl)-amide

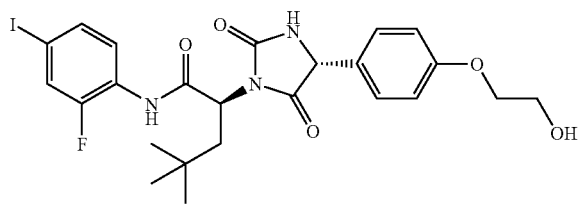

Prepared by the same method as described in example 43 except that (i) (S)-2-(9H-fluoren-9-ylmethoxycarbonylamino)-4,4-dimethyl-2-yl-pentanoic acid was used in place of (S)-2-(9H-fluoren-9-ylmethoxycarbonylamino)-3-naphthalen-2-yl-propanoic acid in step 1, and (ii) steps 4 to 7 were performed as described below:

Step 4: To the solution of 2-amino-4,4-dimethyl-pentanoic acid (2-fluoro-4-iodo-phenyl)-amide (364 mg, 1 mmol), (R)-tert-butoxycarbonylamino-[4-(2-tert-butoxy-ethoxy)-phenyl]-acetic acid (1 M in DMF, 1.1 mL, 1.1 mmol), 1-Hydroxybenzotriazole (168 mg, 1.1 mmol) and diisopropylethyl amine (0.53 mL, 3.3 mmol) in N,N-dimethylformamide (5 mL) was added dropwise the solution of O-benzotriazol-1-yl-N,N,N',N'-bis(tetramethylene)uronium hexaflurorophosphate (474 mg, 1.1 mmol). The reaction mixture was stirred for 1 hour at room temperature. The reaction mixture was diluted with ethyl acetate and the mixture washed with water and brine. The organic layers were successively washed with 1 M aqueous citric acid solution, brine, saturated aqueous sodium carbonate, brine, dried over sodium sulfate, filtered, and concentrated to give {(R)-[4-(2-tert-butoxy-ethoxy)-phenyl]-[(S)-1-(2-fluoro-4-iodo-phenylcarbamoyl)-3,3-dimethyl-butylcarbamoyl]-methyl}carbamic acid tert-butyl ester (652 mg, 91%) as a white solid.

LC-MS: Obs Mass (M+H$^+$)=714; Calcd. Mass, 714 for $C_{32}H_{45}FIN_3O_6^+$.

Step 5: To a solution of {(R)-[4-(2-tert-butoxy-ethoxy)-phenyl]-[(S)-1-(2-fluoro-4-iodo-phenylcarbamoyl)-3,3-dimethyl-butylcarbamoyl]-methyl}-carbamic acid tert-butyl ester (652 mg, 0.91 mmol) in acetonitrile (6 mL) was added 4 N hydrogen chloride in dioxane (1 mL, 4 mmol) and the mixture stirred at 40° C. for 30 minutes. The reaction mixture was concentrated in vacuo and the residue suspended in ice cold water. The aqueous suspension was neutralized to basic pH with saturated aqueous sodium carbonate solution then extracted with dichloromethane (three times). The combined organic extracts were dried over sodium sulfate, filtered and concentrated in vacuo and the residue purified by chromatography over silica gel gradient eluted from 100% dichloromethane up to 10% methanol/90% dichloromethane in 30 minutes. Concentration of the product containing fractions gave (S)-2-{(R)-2-amino-2-[4-(2-tert-butoxy-ethoxy)-phenyl]-acetylamino}-4,4-dimethyl-pentanoic acid (2-fluoro-4-iodo-phenyl)-amide (490 mg, 87%).

LC-MS: Obs Mass (M+H$^+$)=614; Calcd. Mass, 614 for $C_{27}H_{38}FIN_3O_4^+$.

Step 6: To a solution of diphosgene (41 μL, 0.34 mmol) in 1:1 v/v toluene/tetrahydrofuran (18 mL total) at −35° C. under an atmosphere of dry argon was added a solution of (S)-2-{(R)-2-amino-2-[4-(2-tert-butoxy-ethoxy)-phenyl]-acetylamino}4,4-dimethyl-pentanoic acid (2-fluoro-4-iodo-phenyl)-amide (300 mg, 0.49 mmol) and N,N-diisopropylethylamine (260 μL, 1.47 mmol) in tetrahydrofuran (9 mL) dropwise with stirring over 10 minutes. After an additional 45 minutes ice was added and the reaction mixture stirred vigorously and warmed to ambient temperature. The reaction mixture was poured into water, extracted with ethyl acetate (twice) and the combined organic layers washed sequentially with water (twice), 0.1 M aqueous hydrochloric acid, water, saturated aqueous sodium hydrogen carbonate, water and brine, then dried over sodium sulfate, filtered and concentrated in vacuo to give (S)-2-{(R)-4-[4-(2-tert-butoxy-ethoxy)-phenyl]-2,5-dioxo-imidazolidin-1-yl}4,4-dimethyl-pentanoic acid (2-fluoro-4-iodo-phenyl)-amide as yellow sticky solid (295 mg, 95%) which was used in the subsequent step without further purification.

LC-MS: Obs Mass (M+H$^+$), 640; Calcd. Mass, 640 for $C_{28}H_{36}FIN_3O_5^+$.

Step 7: To a solution of (S)-2-{(R)-4-[4-(2-tert-butoxy-ethoxy)-phenyl]-2,5-dioxo-imidazolidin-1-yl}-4,4-dimethyl-pentanoic acid (2-fluoro-4-iodo-phenyl)-amide (295 mg, 0.46 mmol) in dichloromethane (3 mL) at 0° C. under an atmosphere of dry argon was slowly added a solution of trimethylsilyl iodide (183 uL, 1.3 mmol) in dichloromethane (1 mL). The reaction mixture stirred at ambient temperature for 2 hours. Methanol (0.5 mL) was added to quench the reaction. The reaction mixture extracted with dichloromethane and the organic layer was washed sequentially with saturated aqueous sodium carbonate, 5% aqueous sodium thiosulfate, brine, then dried over sodium sulfate, filtered and concentrated in vacuo. The residue was purified by chromatography over silica gel gradient eluted from 100% hexane up to 50% ethyl acetate/50% hexane over 30 minutes. Concentration of the product containing fractions gave (S)-2-{(R)-4-[4-(2-hydroxy-ethoxy)-phenyl]-2,5-dioxo-imidazolidin-1-yl}-4,4-dimethyl-pentanoic acid (2-fluoro-4-iodo-phenyl)-amide as a white solid (126 mg, 47%).

LC-MS: Obs Mass (M+H$^+$), 584; Calcd. Mass, 584 for $C_{24}H_{28}FIN_3O_5^+$.

EXAMPLE 94

(S)-2-Cyclopropyl-N-(2-fluoro-4-iodo-phenyl)-2-{(R)-4-[4-(2-hydroxy-ethoxy)-phenyl]-2,5-dioxo-imidazolidin-1-yl}-acetamide

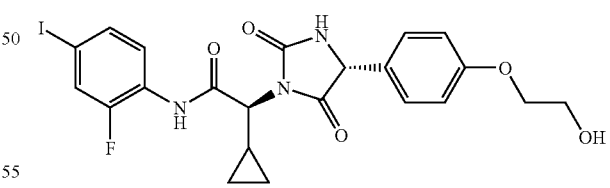

Prepared by the same method as described in example 48 except that (i) (S)-tert-butoxycarbonylamino-cyclopropyl-acetic acid was used in place of (2S,3S)-2-tert-butoxycarbonylamino-3-phenyl-butyric acid in step 1, and (ii) O-benzotriazol-1-yl-N,N,N',N'-bis(tetramethylene)uronium hexaflurorophosphate was used as the coupling reagent in place of O-benzotriazol-1-yl-N,N,N',N'-tetramethyluronium hexaflurorophosphate in step 4.

LC-MS: Obs Mass (M+H$^+$), 554; Calcd. Mass, 554 for $C_{22}H_{22}FIN_3O_5^+$.

EXAMPLE 95

(S)-3-Cyclopropyl-N-(2-fluoro-4-iodo-phenyl)-2-{(R)-4-[4-(2-hydroxy-ethoxy)-phenyl]-2,5-dioxo-imidazolidin-1-yl}-propionamide

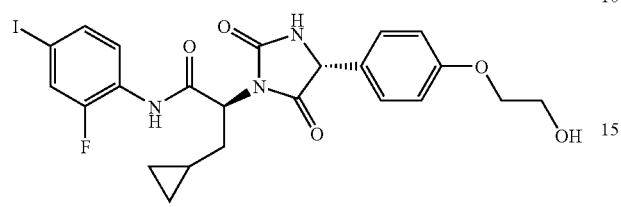

Prepared by the same method as described in example 48 except that (i) (S)-2-tert-butoxycarbonylamino-3-cyclopropyl-propionic acid was used in place of (2S,3S)-2-tert-butoxycarbonylamino-3-phenyl-butyric acid in step 1, and (ii) O-benzotriazol-1-yl-N,N,N',N'-bis(tetramethylene)uronium hexaflurorophosphate was used as the coupling reagent in place of O-benzotriazol-1-yl-N,N,N',N'-tetramethyluronium hexaflurorophosphate in step 4.

LC-MS: Obs Mass (M+H$^+$), 568; Calcd. Mass, 568 for $C_{23}H_{24}FIN_3O_5^+$.

EXAMPLE 96

(S)-3-Cyclohexyl-N-(2-fluoro-4-iodo-phenyl)-2-{(R)-4-[4-(2-hydroxy-ethoxy)-phenyl]-2,5-dioxo-imidazolidin-1-yl}-propionamide

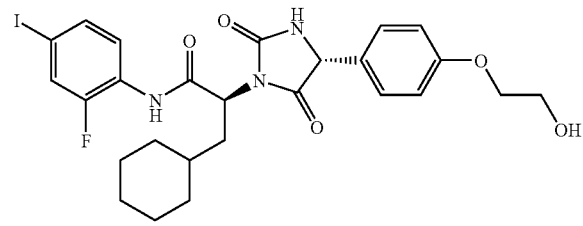

Prepared by the same method as described in example 48 except that (i) (S)-2-tert-butoxycarbonylamino-3-cyclohexyl-propionic acid was used in place of (2S,3S)-2-tert-butoxycarbonylamino-3-phenyl-butyric acid in step 1, and (ii) O-benzotriazol-1-yl-N,N,N',N'-bis(tetramethylene)uronium hexaflurorophosphate was used as the coupling reagent in place of O-benzotriazol-1-yl-N,N,N',N'-tetramethyluronium hexaflurorophosphate in step 4.

LC-MS: Obs Mass (M+H$^+$), 610; Calcd. Mass, 610 for $C_{26}H_{30}FIN_3O_5^+$.

EXAMPLE 97

(2S,3R)—N-(2-Fluoro-4-iodo-phenyl)-2-[(R)-4-(4-hydroxy-phenyl)-2,5-dioxo-imidazolidin-1-yl]-3-methoxy-butyramide

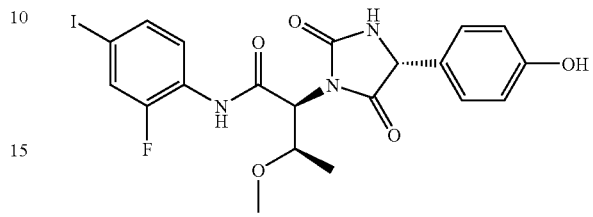

Prepared by the same method as described in example 1 except that (i) (2S,3R)-2-tert-butoxycarbonylamino-3-methoxy-butyric acid was used in place of (2S,3S)-2-tert-butoxycarbonylamino-3-phenyl-butyric acid in step 1, (ii) 2-fluoro-4-iodoaniline was used in place of 4-bromoaniline in step 2, (iii) O-benzotriazol-1-yl-N,N,N',N'-bis(tetramethylene)uronium hexaflurorophosphate was used as the coupling reagent in place of O-benzotriazol-1-yl-N,N,N',N'-tetramethyluronium hexaflurorophosphate in step 4, and (iv) (R)-tert-butyloxycarbonylamino-4-hydroxyphenylglycine was used in place of (R)-tert-butyloxycarbonylamino-4-methoxyphenylglycine in step 4.

LC-MS: Obs Mass (M+H$^+$), 528; Calcd. Mass, 528 for $C_{20}H_{20}FIN_3O_5^+$.

EXAMPLE 98

(2S,3R)—N-(2-Fluoro-4-iodo-phenyl)-2-{(R)-4-[4-(2-hydroxy-ethoxy)-phenyl]-2,5-dioxo-imidazolidin-1-yl}-3-methoxy-butyramide

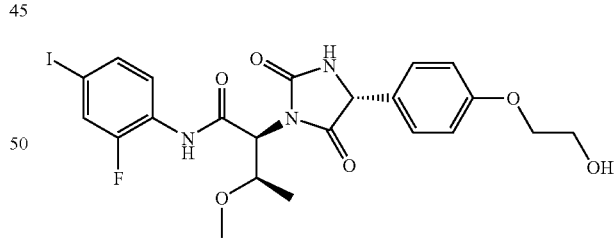

Prepared by the same method as described in example 48 except that (i) (2S,3R)-2-tert-butoxycarbonylamino-3-methoxy-butyric acid was used in place of (2S,3S)-2-tert-butoxycarbonylamino-3-phenyl-butyric acid in step 1, and (ii) O-benzotriazol-1-yl-N,N,N',N'-bis(tetramethylene)uronium hexaflurorophosphate was used as the coupling reagent in place of O-benzotriazol-1-yl-N,N,N',N'-tetramethyluronium hexaflurorophosphate in step 4.

LC-MS: Obs Mass (M+H$^+$), 572; Calcd. Mass, 572 for $C_{22}H_{24}FIN_3O_6^+$.

EXAMPLE 99

(2S,3R)-2-{(R)-4-[4-((R)-2,3-Dihydroxy-propoxy)-phenyl]-2,5-dioxo-imidazolidin-1-yl}-N-(2-fluoro-4-iodo-phenyl)-3-methoxy-butyramide

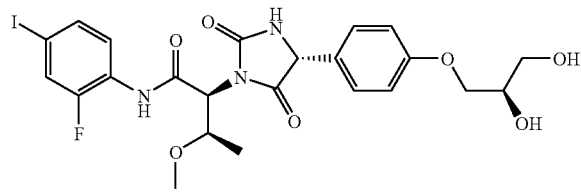

Prepared by the same method as described in example 114 except that (i) (2S,3R)-2-tert-butoxycarbonylamino-3-methoxy-butyric acid was used in place of (2S,3S)-2-tert-butoxycarbonylamino-3-phenyl-butyric acid in step 1, (ii) 2-fluoro-4-iodoaniline was used in place of 2-chloro-4-iodoaniline in step 2, and (iii) O-benzotriazol-1-yl-N,N,N',N'-bis(tetramethylene)uronium hexaflurorophosphate was used as the coupling reagent in place of O-benzotriazol-1-yl-N,N,N',N'-tetramethyluronium hexaflurorophosphate in step 4.

LC-MS: Obs Mass (M+H$^+$), 602; Calcd. Mass, 602 for $C_{23}H_{26}FIN_3O_7+$.

EXAMPLE 100

(2S,3R)-3-Benzyloxy-2-{(R)-4-[4-((R)-2,3-dihydroxy-propoxy)-phenyl]-2,5-dioxo-imidazolidin-1-yl}-N-(2-fluoro-4-iodo-phenyl)-butyramide

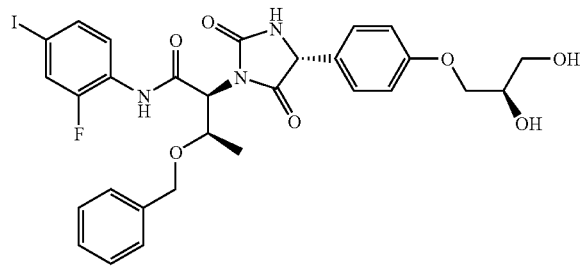

Prepared by the same method as described in example 43 except that (i) (2S,3R)-3-benzyloxy-2-(9H-fluoren-9-ylmethoxycarbonylamino)-butyric acid was used in place of (S)-2-(9H-fluoren-9-ylmethoxycarbonylamino)-3-naphthalen-2-yl-propionic acid in step 1, and (ii) the steps following step 3 were performed as described in example 114.

LC-MS: Obs Mass (M+H$^+$), 678; Calcd. Mass, 678 for $C_{29}H_{30}FIN_3O_7^+$.

EXAMPLE 101

(2S,3R)-2-{(R)-4-[4-((R)-2,3-Dihydroxy-propoxy)-phenyl]-2,5-dioxo-imidazolidin-1-yl}-N-(2-fluoro-4-iodo-phenyl)-3-hydroxy-butyramide

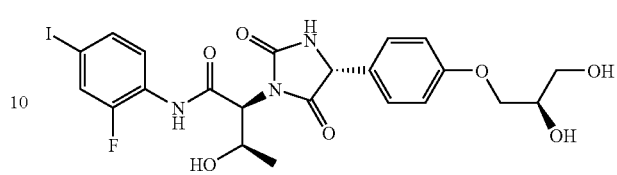

Prepared by the same method as described in example 43 except that (i) (2S,3R)-3-tert-butoxy-2-(9H-fluoren-9-ylmethoxycarbonylamino)-butyric acid was used in place of (S)-2-(9H-fluoren-9-ylmethoxycarbonylamino)-3-naphthalen-2-yl-propionic acid in step 1, and (ii) the steps following step 4 were performed as described in example 114.

LC-MS: Obs Mass (M+H$^+$), 588; Calcd. Mass, 588 for $C_{22}H_{24}FIN_3O_7+$.

EXAMPLE 102

(S)—N-(2-Fluoro-4-iodo-phenyl)-2-{(R)-4-[4-(2-hydroxy-ethoxy)-phenyl]-2,5-dioxo-imidazolidin-1-yl}4-phenyl-butyramide

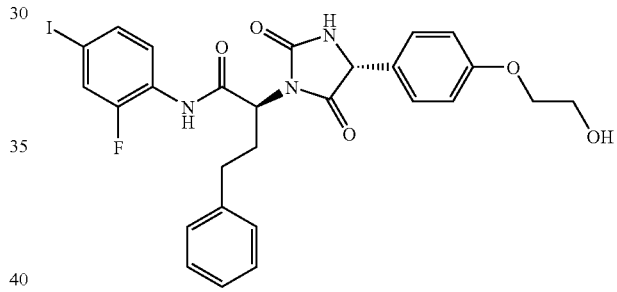

Prepared by the same method as described in example 72 except that (S)-2-tert-butoxycarbonylamino-4-phenyl-2-yl-butyric acid was used in place of (S)-2-tert-butoxycarbonylamino-3-thiophen-2-yl-propionic acid in step 1.

LC-MS: Obs Mass (M+H$^+$), 618; Calcd. Mass, 618 for $C_{27}H_{26}FIN_3O_5^+$.

EXAMPLE 103

(S)—N-(2-Fluoro-4-iodo-phenyl)-2-{(R)-4-[4-(2-hydroxy-ethoxy)-phenyl]-2,5-dioxo-imidazolidin-1-yl}-4-methanesulfonyl-butyramide

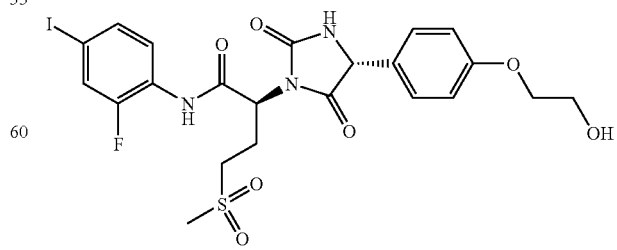

Prepared by the same method as described in example 43 except that (S)-2-(9H-fluoren-9-ylmethoxycarbonylamino)-

4-methanesulfonyl-butyric acid was used in place of (S)-2-(9H-fluoren-9-ylmethoxycarbonylamino)-3-naphthalen-2-yl-propionic acid in step 1.

LC-MS: Obs Mass (M+H$^+$), 620; Calcd. Mass, 620 for C$_{22}$H$_{24}$FIN$_3$O$_7$S$^+$.

EXAMPLE 104

(S)-2-{(R)-4-[4-(2-Hydroxy-ethoxy)-phenyl]-2,5-dioxo-imidazolidin-1-yl}-pentanedioic acid 5-amide 1-[(2-fluoro-4-iodo-phenyl)-amide]

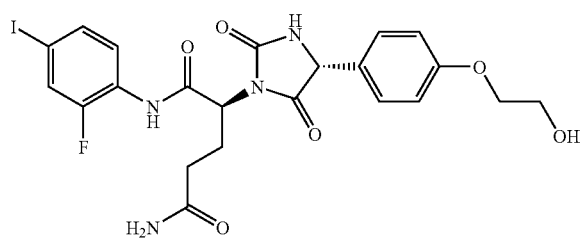

Prepared by the same method as described in example 72 except that (S)-2-tert-butoxycarbonylamino-4-carbamoyl-butyric acid was used in place of (S)-2-tert-butoxycarbonylamino-3-thiophen-2-yl-propionic acid in step 1.

LC-MS: Obs Mass (M+H$^+$), 585; Calcd. Mass, 585 for C$_{22}$H$_{23}$FIN$_4$O$_6^+$.

EXAMPLE 105

(S)—N-(2-Chloro-4-iodo-phenyl)-2-{(R)-4-[4-(2-hydroxy-ethoxy)-phenyl]-2,5-dioxo-imidazolidin-1-yl}-3-phenyl-propionamide

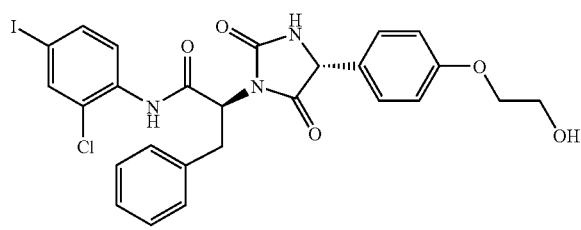

Prepared by the same method as described in example 3 except that (i) 2-chloro-4-iodo-aniline was used in place of 4-bromo-2-chloro-aniline in step 1, and (ii) (S)-2-tert-butoxycarbonylamino-3-phenyl-propionic acid was used in place of (S,S)-2-tert-butoxycarbonylamino-3-phenyl-butyric acid in step 1.

HRMS: Obs Mass (M+H$^+$), 620.0442. Calcd. Mass, 620.0444 for C$_{26}$H$_{24}$ClIN$_3$O$_5^+$.

EXAMPLE 106

(S)—N-(2-Chloro-4-iodo-phenyl)-2-{(R)-4-[4-(2-methoxy-ethoxy)-phenyl]-2,5-dioxo-imidazolidin-1-yl}-3-phenyl-propionamide

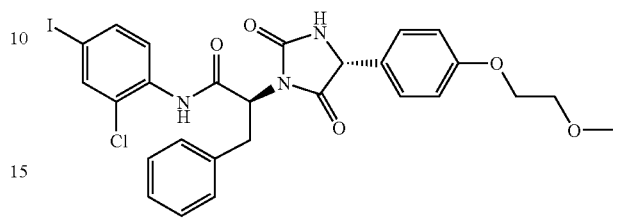

Prepared by the same method as described in example 3 except that (i) 2-chloro-4-iodo-aniline was used in place of 4-bromo-2-chloro-aniline in step 1, (ii) (S)-2-tert-butoxycarbonylamino-3-phenyl-propionic acid was used in place of (S,S)-2-tert-butoxycarbonylamino-3-phenyl-butyric acid in step 1, and (iii) R)-tert-butoxycarbonylamino-[4-(2-methoxy-ethoxy)-phenyl]-acetic acid was used in place of (R)-tert-butoxycarbonylamino-[4-(2-tert-butoxy-ethoxy)-phenyl]-acetic acid in step 2. (R)-tert-butoxycarbonylamino-[4-(2-methoxy-ethoxy)-phenyl]-acetic acid was prepared as described in example 80.

HRMS: Obs Mass (M+H$^+$), 634.0602. Calcd. Mass, 634.0600 for C$_{27}$H$_{26}$ClIN$_3$O$_5^+$.

EXAMPLE 107

(S)—N-(2-Chloro-4-iodo-phenyl)-2-{(R)-4-[4-((R)-2,3-dihydroxy-propoxy)-phenyl]-2,5-dioxo-imidazolidin-1-yl}-3-phenyl-propionamide

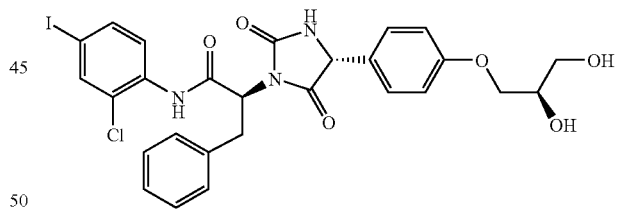

Prepared by the same method as described in example 3 except that (i) 2-chloro-4-iodo-aniline was used in place of 4-bromo-2-chloro-aniline in step 1, (ii) (S)-2-tert-butoxycarbonylamino-3-phenyl-propionic acid was used in place of (S,S)-2-tert-butoxycarbonylamino-3-phenyl-butyric acid in step 1, and (iii) (R)-tert-butoxycarbonylamino-[4-((S)-2,2-dimethyl-[1,3]dioxolan-4-ylmethoxy)-phenyl]-acetic acid was used in place of (R)-tert-butoxycarbonylamino-[4-(2-tert-butoxy-ethoxy)-phenyl]-acetic acid in step 2. (R)-tert-Butoxycarbonylamino-[4-((S)-2,2-dimethyl-[1,3]dioxolan-4-ylmethoxy)-phenyl]-acetic acid was prepared and used as described in example 114.

HRMS: Obs Mass (M+H$^+$), 650.0541. Calcd. Mass, 650.0550 for C$_{27}$H$_{26}$ClIN$_3$O$_6^+$.

EXAMPLE 108

(2S,3S)—N-(2-Chloro-4-iodo-phenyl)-2-[(R)-4-(4-methoxy-phenyl)-2,5-dioxo-imidazolidin-1-yl]-3-phenyl-butyramide

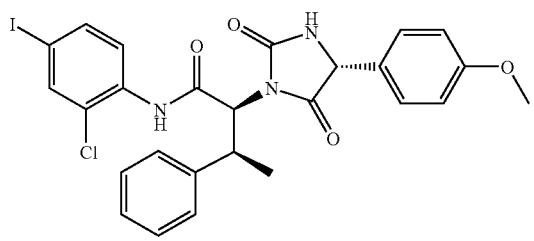

Prepared by the method as described in example 1 except that (i) 2-chloro-4-iodoaniline was used in place of 4-bromoaniline in step 2, and (ii) (3-dimethylamino-propyl)-ethylcarbodiimide hydrochloride was used as the coupling reagent in place of O-benzotriazol-1-yl-N,N,N',N'-tetramethyluronium hexaflurorophosphate in step 4.

HRMS: Obs Mass (M+H$^+$), 604.0496. Calcd. Mass, 604.0495 for $C_{26}H_{24}ClIN_3O_4^+$.

EXAMPLE 109

(2S,3S)—N-(2-Chloro-4-iodo-phenyl)-2-[(R)-4-(4-cyclopropylmethoxy-phenyl)-2,5-dioxo-imidazolidin-1-yl]-3-phenyl-butyramide

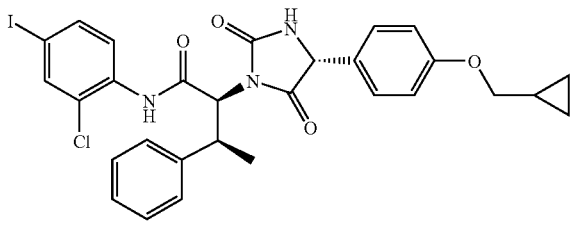

Prepared by the same method as described in example 3 except that 2-chloro-4-iodoaniline was used in place of 2-chloro-4-bromoaniline in step 1 and (R)-tert-butoxycarbonylamino-(4-cyclopropylmethoxy-phenyl)-acetic acid was used in place of (R)-tert-butoxycarbonylamino-[4-(2-tert-butoxy-ethoxy)-phenyl]-acetic acid in step 2. (R)-tert-butoxycarbonylamino-[4-(2-tert-butoxy-ethoxy)-phenyl]-acetic acid was prepared by a similar method as described for the preparation of (R)-tert-butoxycarbonylamino-{4-[2-(tetrahydro-pyran-2-yloxy)-ethoxy]-phenyl}-acetic acid in example 48 except that cyclopropylmethyl bromide was used in place of 2-(2-bromo-ethoxy)-tetrahydropyran.

HRMS: Obs Mass (M+H$^+$), 644.0799. Calcd. Mass, 644.0808 for $C_{29}H_{28}ClIN_3O_4^+$.

EXAMPLE 110

(2S,3S)—N-(2-Chloro-4-iodo-phenyl)-2-{(R)-4-[4-(2-hydroxy-ethoxy)-phenyl]-2,5-dioxo-imidazolidin-1-yl}-3-phenyl-butyramide

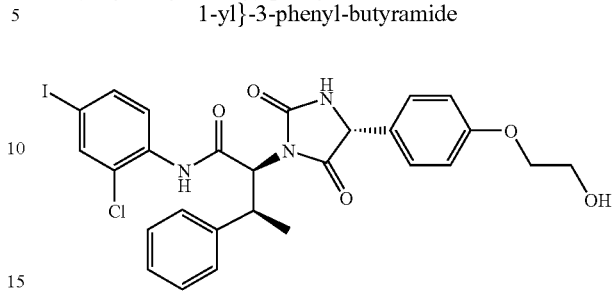

Prepared by the same method as described in example 48 except that 2-chloro-4-iodoaniline was used in place of 2-fluoro-4-iodoaniline in step 2.

HRMS: Obs. Mass (M+H$^+$), 634.0597. Calcd. Mass, 634.0600 for $C_{27}H_{26}ClIN_3O_5^+$. LC-MS (reverse phase HPLC, C18 column, water/acetonitrile gradient): $R_t$=2.36 minutes, Obs. Mass (M+Na$^+$), 656. Calcd. Mass, 640 for $C_{27}H_{25}ClIN_3NaO_5^+$. $^1$H NMR (DMSO-d$_6$, 300 MHz) $\delta_H$ 9.85 (s, 1H), 8.56 (s, 1H), 4.95 (d, J=11.5 Hz, 1H) ppm (characteristic resonances).

EXAMPLE 111

(2S,3S)—N-(2-Chloro-4-iodo-phenyl)-2{(S)-4-[4-(2-hydroxy-ethoxy)-phenyl]-2,5-dioxo-imidazolidin-1-yl}-3-phenyl-butyramide

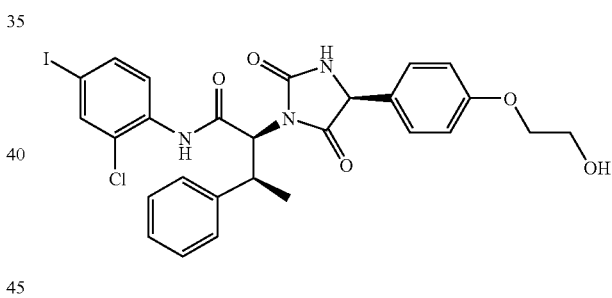

A solution of (2S,3S)—N-(2-chloro-4-iodo-phenyl)-2-{(R)-4-[4-(2-hydroxy-ethoxy)-phenyl]-2,5-dioxo-imidazolidin-1-yl}-3-phenyl-butyramide (prepared as described in example 110) (50 mg, 0.079 mmol) was dissolved in methanol (3 mL) and stirred at ambient temperature for 4 days. The resulting mixture of isomers was concentrated in vacuo and then purified by super-critical fluid chromatography using a Chiracel OJ column eluted with carbon dioxide at 100 bar and 30° C. modified with 35% v/v ethanol in acetonitrile eluted at 2 mL/minute. The first eluted compound was collected and concentrated in vacuo to obtain (2S,3S)—N-(2-chloro-4-iodo-phenyl)-2-{(S)-4-[4-(2-hydroxy-ethoxy)-phenyl]-2,5-dioxo-imidazolidin-1-yl}-3-phenyl-butyramide (14.6 mg, 29%) The compound eluted second was identical with (2S, 3S)—N-(2-chloro-4-iodo-phenyl)-2-{(R)-4-[4-(2-hydroxy-ethoxy)-phenyl]-2,5-dioxo-imidazolidin-1-yl}-3-phenyl-butyramide (18.1 mg, 36%). LC-MS (reverse phase HPLC, C18 column, water/acetonitrile gradient): $R_t$=2.40 minutes, Obs. Mass (M+Na$^+$), 656. Calcd. Mass, 640 for $C_{27}H_{25}ClIN_3NaO_5^+$. $^1$H NMR (DMSO-d$_6$, 300 MHz) OH 9.98 (s, 1H), 8.61 (s, 1H), 4.81 (d, J=11.8 Hz, 1H) ppm (characteristic resonances).

EXAMPLE 112

(2S,3S)—N-(2-Chloro-4-iodo-phenyl)-2-{(R)-4-[4-((R)-2-hydroxy-propoxy)-phenyl]-2,5-dioxo-imidazolidin-1-yl}-3-phenyl-butyramide

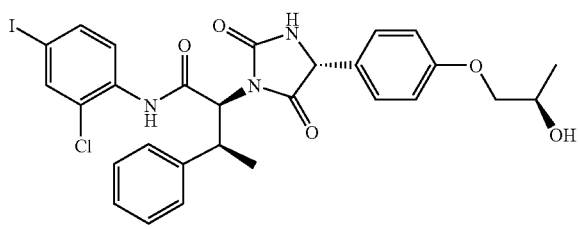

Prepared by the same method as described in example 3 except that (i) 2-chloro-4-iodo-aniline was used in place of 4-bromo-2-chloro-aniline in step 1, and (ii) (R)-tert-butoxycarbonylamino-[4-((R)-2-hydroxy-propoxy)-phenyl]-acetic acid was used in place of (R)-tert-butoxycarbonylamino-[4-(2-tert-butoxy-ethoxy)-phenyl]-acetic acid in step 2. (R)-tert-Butoxycarbonylamino-[4-((R)-2-hydroxy-propoxy)-phenyl]-acetic acid was prepared as described in example 48 except that (R)-2-methyl-oxirane was used in place of 2-(2bromo-ethoxy)-tetrahydropyran.

HRMS: Obs Mass (M+H$^+$), 648.0755. Calcd. Mass, 648.0757 for $C_{28}H_{28}ClIN_3O_5^+$.

EXAMPLE 113

(2S,3S)—N-(2-Chloro-4-iodo-phenyl)-2-{(R)-4-[4-(2-methoxy-ethoxy)-phenyl]-2,5-dioxo-imidazolidin-1-yl}-3-phenyl-butyramide

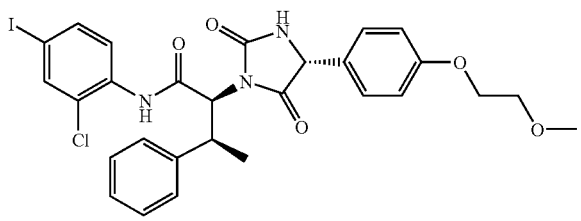

Prepared by the same method as described in example 3 except that (i) 2-chloro-4-iodo-aniline was used in place of 4-bromo-2-chloro-aniline in step 1, and (ii) (R)-tert-butoxycarbonylamino-[4-(2-methoxy-ethoxy)-phenyl]-acetic acid was used in place of (R)-tert-butoxycarbonylamino-[4-(2-tert-butoxy-ethoxy)-phenyl]-acetic acid in step 2. (R)-tert-Butoxycarbonylamino-[4-(2-methoxy-ethoxy)-phenyl]-acetic acid was prepared as described in example 80.

HRMS: Obs Mass (M+H$^+$), 648.0746. Calcd. Mass, 648.0757 for $C_{28}H_{28}ClIN_3O_5^+$.

EXAMPLE 114

(2S,3S)—N-(2-Chloro-4-iodo-phenyl)-2-{(R)-4-[4-((R)-2,3-dihydroxy-propoxy)-phenyl]-2,5-dioxo-imidazolidin-1-yl}-3-phenyl-butyramide

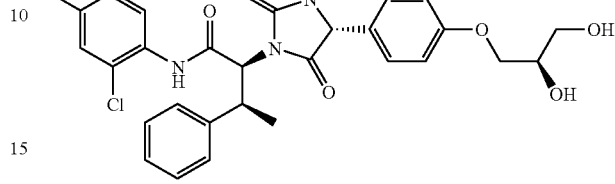

Prepared by the same method as described in example 110 except that (i) (R)-tert-butoxycarbonylamino-[4-((S)-2,2-dimethyl-[1,3]dioxolan-4-ylmethoxy)-phenyl]-acetic acid (prepared as described below) was used in place of (R)-tert-butoxycarbonylamino-{4-[2-(tetrahydro-pyran-2-yloxy)-ethoxy]-phenyl}-acetic acid in step 4, (ii) (2S,3S)-2-{(R)-2-amino-2-[4-((R)-2,3-dihydroxy-propoxy)-phenyl]-acetylamino}-N-(2-chloro-4-iodo-phenyl)-3-phenyl-butyramide was temporarily protected as (2S,3S)-2-{(R)-2-amino-2-[4-((S)-2,3-bis-trimethylsilanyloxy-propoxy)-phenyl]-acetylamino}-N-(2-chloro-4-iodo-phenyl)-3-phenyl-butyramide (performed as described below) prior to performing step 6, and (iii) acid catalyzed hydrolysis of (2S,3S)-2-{(R)-4-[4-((S)-2,3-bis-trimethylsilanyloxy-propoxy)-phenyl]-2,5-dioxo-imidazolidin-1-yl}-N-(2-chloro-4-iodo-phenyl)-3-phenyl-butyramide (performed as described below) was performed prior to purification and isolation of (2S,3S)—N-(2-chloro-4-iodo-phenyl)-2-{(R)-4-[4-((R)-2,3-dihydroxy-propoxy)-phenyl]-2,5-dioxo-imidazolidin-1-yl}-3-phenyl-butyramide in step 6.

Preparation of (R)-tert-butoxycarbonylamino-[4-((S)-2,2-dimethyl-[1,3]dioxolan-4-ylmethoxy)-phenyl]-acetic acid (1) To a solution of (S)-2,2-dimethyl-1,3-dioxolane-4-methanol (5.22 g, 39.5 mmol) in dichloromethane (60 mL) at 0° C. under an atmosphere of dry argon were added triethylamine (11 mL, 79 mmol) and 2,5-dichlorosulfonyl chloride (10.18 g, 41.5 mmol) and the mixture left to stir and warm slowly to ambient temperature overnight. The reaction mixture was diluted with dichloromethane and washed with water. The aqueous layer was separated and washed once with dichloromethane. The combined organic layers were washed with saturated aqueous sodium hydrogen carbonate solution (once), brine (once), dried over sodium sulfate, filtered and concentrated in vacuo to leave an oily residue. The residue was purified by chromatography over silica gel gradient eluted form 0 to 40% v/v ethyl acetate in hexanes to give 2,5-dichloro-benzenesulfonic acid (R)-2,2-dimethyl-[1,3]dioxolan-4-ylmethyl ester as a colorless solid (11.06 g, 82%).

(2) To a stirred solution of (R)-tert-butoxycarbonylamino-(4-hydroxy-phenyl)-acetic acid (1.4 g, 5.24 mmol) in dry N,N-dimethylformamide (25 mL) at 0° C. under an atmosphere of dry argon was added sodium hydride (60% suspension in mineral oil) (290 mg, 0.12 mmol) and the mixture stirred at 0° C. for 15 minutes. 2,5-Dichloro-benzenesulfonic acid (R)-2,2-dimethyl-[1,3]dioxolan-4-ylmethyl ester (2.14 mmol, 6.29 mmol) was added to the reaction mixture to form a yellow solution which was stirred at ambient temperature for 5 minutes before warming to 100° C. for 10 minutes. The reaction mixture which by now contained a heavy precipitate was cooled to ambient temperature, diluted with ethyl acetate, cooled to 0° C. and treated with an equal volume of water. The stirred mixture was acidified to pH=4 with 1 M aqueous hydrochloric acid. The organic layer was separated and the aqueous layer extracted with ethyl acetate. The combined organic layers were washed with water (three times), dried over sodium sulfate, filtered through a thin pad of silica gel and concentrated in vacuo to give (R)-tert-butoxycarbonylamino-[4-((S)-2,2-dimethyl-[1,3]dioxolan-4-yl-methoxy)-phenyl]-acetic acid as a pale yellow solid foam which was of adequate purity for subsequent use in step 4 without additional purification (1.96 g, 96%).

Preparation of (2S,3S)-2-{(R)-2-amino-2-[4-((S)-2,3-bis-trimethylsilanyloxy-propoxy)-phenyl]-acetylamino}-N-(2-chloro-4-iodo-phenyl)-3-phenyl-butyramide:

To a solution of (2S,3S)-2-{(R)-2-amino-2-[4-((R)-2,3-dihydroxy-propoxy)-phenyl]-acetylamino}-N-(2-chloro-4-iodo-phenyl)-3-phenyl-butyramide (330 mg, 0.44 mmol) in dry, degassed tetrahydrofuran (5 mL) were added triethylamine (277 µL, 1.98 mmol) and chlorotrimethylsilane (230 µL, 1.76 mmol) and the mixture stirred at ambient temperature for 30 minutes. The resulting suspension was diluted with ethyl acetate (50 mL) and washed with brine (2×50 mL). The combined brine layers were back extracted with ethyl acetate (2×50 mL), the combined organic layers dried over sodium sulfate, filtered and concentrated in vacuo to give crude (2S,3S)-2-{(R)-2-amino-2-[4-((S)-2,3-bis-trimethylsilanyloxy-propoxy)-phenyl]-acetylamino}-N-(2-chloro-4-iodo-phenyl)-3-phenyl-butyramide which was of adequate purity for subsequent use in step 6 without additional purification (330 mg, 96%).

Hydrolysis of (2S,3S)-2-{(R)-4-[4-((S)-2,3-bis-trimethylsilanyloxy-propoxy)-phenyl]-2,5-dioxo-imidazolidin-1-yl}N-(2-chloro-4-iodo-phenyl)-3-phenyl-butyramide:

Following cyclization of (2S,3S)-2-{(R)-2-amino-2-[4-((S)-2,3-bis-trimethylsilanyloxy-propoxy)-phenyl]-acetylamino}-N-(2-chloro-4-iodo-phenyl)-3-phenyl-butyramide using a method similar to that described in example 6 crude (2S,3S)-2-{(R)-4-[4-((S)-2,3-bis-trimethylsilanyloxy-propoxy)-phenyl]-2,5-dioxo-imidazolidin-1-yl}-N-(2-chloro-4-iodo-phenyl)-3-phenyl-butyramide was dissolved in ethyl acetate (50 mL) and mixed vigorously with 1:1 v/v 1M aqueous hydrochloric acid/brine at ambient temperature for 15 minutes to effect removal of the trimethylsilyl protecting groups. The layers were separated and the aqueous layer extracted with ethyl acetate (2×50 mL). The combined ethyl acetate layers were dried over sodium sulfate, filtered and concentrated in vacuo prior to final purification by chromatography over silica gel gradient eluted in 1% v/v steps between 100% dichloromethane and 3% methanol in dichloromethane. After concentration in vacuo of the product containing fractions the glassy residue was dissolved in dichloromethane (0.5 mL), diluted with diethyl ether (2 mL) and hexanes (15 mL) added to precipitate (2S,3S)—N-(2-chloro-4-iodo-phenyl)-2-{(R)-4-[4-((R)-2,3-dihydroxy-propoxy)-phenyl]-2,5-dioxo-imidazolidin-1-yl}-3-phenyl-butyramide which was obtained as a colorless solid after filtration and drying in vacuo (72 mg, 25%).

HRMS: Obs. Mass, 664.0703. Calcd. Mass, 664.0706 for $C_{28}H_{28}ClIN_3O_6^+$.

EXAMPLE 115

(2S,3S)—N-(2-Chloro-4-iodo-phenyl)-2-{(S)-4-[4-((R)-2,3-dihydroxy-propoxy)-phenyl]-2,5-dioxo-imidazolidin-1-yl}-3-phenyl-butyramide

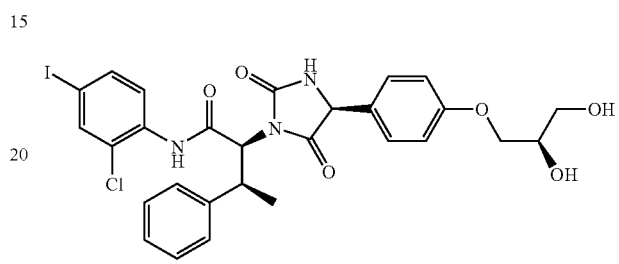

The filtrate from the final purification step in the preparation of (2S,3S)—N-(2-chloro-4-iodo-phenyl)-2-{(R)-4-[4-((R)-2,3-dihydroxy-propoxy)-phenyl]-2,5-dioxo-imidazolidin-1-yl}-3-phenyl-butyramide (prepared as described in example 114) was enriched in (2S,3S)—N-(2-chloro-4-iodo-phenyl)-2-{(R)-4-[4-((R)-2,3-dihydroxy-propoxy)-phenyl]-2,5-dioxo-imidazolidin-1-yl}-3-phenyl-butyramide. The diastereomers were separated by supercritical fluid chromatography using a Daicel OD column eluted with 45% v/v 1:1 acetonitrile/ethanol in carbon dioxide.

HRMS: Obs Mass (M+H$^+$), 664.0706. Calcd. Mass, 664.0706 for $C_{28}H_{28}ClIN_3O_6^+$.

EXAMPLE 116

(2S,3S)—N-(2-Chloro-4-iodo-phenyl)-2-{(R)-4-[4-((S)-2,3-dihydroxy-propoxy)-phenyl]-2,5-dioxo-imidazolidin-1-yl}-3-phenyl-butyramide

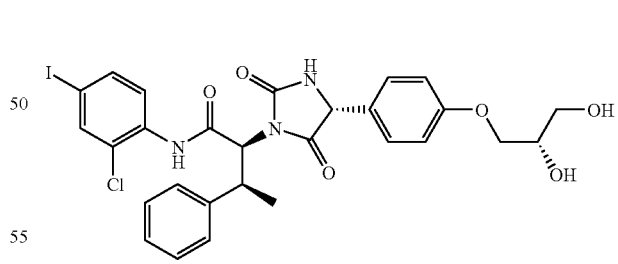

Prepared by the same method as described in example 114 except that (R)-tert-butoxycarbonylamino-[4-((R)-2,2-dimethyl-[1,3]dioxolan-4-ylmethoxy)-phenyl]-acetic acid was used in place of (R)-tert-butoxycarbonylamino-[4-((S)-2,2-dimethyl-[1,3]dioxolan-4-ylmethoxy)-phenyl]-acetic acid in step 4. (R)-tert-butoxycarbonylamino-[4-((R)-2,2-dimethyl-[1,3]dioxolan-4-ylmethoxy)-phenyl]-acetic acid was prepared by the same method as described for the preparation of (R)-tert-butoxycarbonylamino-[4-((S)-2,2-dimethyl-[1,3]dioxolan-4-ylmethoxy)-phenyl]-acetic acid in example 114 except that (R)-2,2-dimethyl-1,3-dioxolane-4-methanol was used in place of (S)-2,2-dimethyl-1,3-dioxolane-4-methanol.

HRMS: Obs. Mass (M+H$^+$), 664.0710. Calcd. Mass, 664.0706 for $C_{28}H_{28}ClIN_3O_6^+$.

EXAMPLE 117

(2S,3S)-2-[(R)-4-(4-{[Bis-(2-hydroxy-ethyl)-carbamoyl]-methoxy}phenyl)-2,5-dioxo-imidazolidin-1-yl]-N-(2-chloro-4-iodo-phenyl)-3-phenyl-butyramide

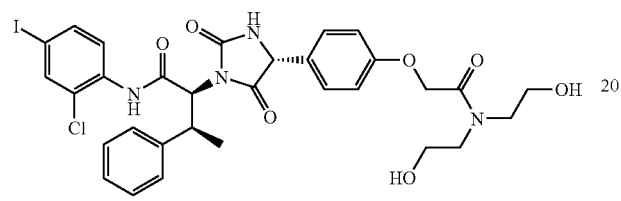

Prepared by the same method as described in example 109 except that (R)-[4-(2-{bis-[2-(tert-butyl-dimethyl-silanyloxy)-ethyl]-amino}-acetoxy)-phenyl]-tert-butoxycarbonylamino-acetic acid was used in place of (R)-tert-butoxycarbonylamino-(4-cyclopropylmethoxy-phenyl)-acetic acid. (R)-[4-(2-{Bis-[2-(tert-butyl-dimethyl-silanyloxy)-ethyl]-amino}-acetoxy)-phenyl]-tert-butoxycarbonylamino-acetic acid was prepared as described in example 48 except that N,N-bis-[2-(tert-butyl-dimethyl-silanyloxy)-ethyl]-2-chloro-acetamide was used in place of 2-(2-bromo-ethoxy)-tetrahydropyran.

HRMS: Obs Mass (M+Na$^+$), 757.0898. Calcd. Mass, 757.0896 for $C_{31}H_{32}ClIN_4NaO_7^+$.

EXAMPLE 118

(S)—N-(2-Chloro-4-iodo-phenyl)-2-{(R)-4-[4-(2-hydroxy-ethoxy)-phenyl]-2,5-dioxo-imidazolidin-1-yl}-3-thiazol-4-yl-propionamide

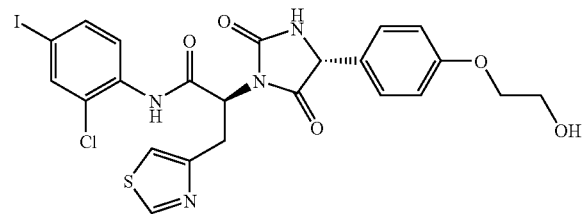

Prepared by the same method as described in example 3 except that (i) 2-chloro-4-iodo-aniline was used in place of 4-bromo-2-chloro-aniline in step 1, and (ii) (S)-2-tert-butoxycarbonylamino-3-thiazol-4-yl-propionic acid was used in place of (2S,3S)-2-tert-butoxycarbonylamino-3-phenyl-butyric acid in step 1.

HRMS: Obs Mass (M+H$^+$), 626.9964. Calcd. Mass, 626.9961 for $C_{23}H_{21}ClIN_4O_5S^+$.

EXAMPLE 119

(S)—N-(2-Chloro-4-iodo-phenyl)-2-[(R)-4-(4-cyclopropylmethoxy-phenyl)-2,5-dioxo-imidazolidin-1-yl]-3-methyl-butyramide

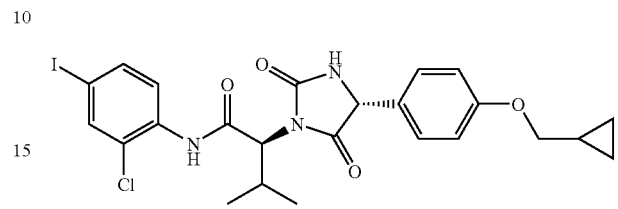

Prepared by the same method as described in example 3 except that (i) 2-chloro-4-iodo-aniline was used in place of 4-bromo-2-chloro-aniline in step 1, (ii) (S)-2-tert-butoxycarbonylamino-3-methyl-butyric acid was used in place of (S,S)-2-tert-butoxycarbonylamino-3-phenyl-butyric acid in step 1, and (iii) (R)-tert-butoxycarbonylamino-(4-cyclopropylmethoxy-phenyl)-acetic acid (prepared as described in example 109) was used in place of (R)-tert-butoxycarbonylamino-[4-(2-tert-butoxy-ethoxy)-phenyl]-acetic acid in step 2.

HRMS: Obs Mass (M+H$^+$), 582.0655. Calcd. Mass, 582.0651 for $C_{24}H_{26}ClIN_3O_4^+$.

EXAMPLE 120

(S)—N-(2-Chloro-4-iodo-phenyl)-2-{(R)-4-[4-(2-hydroxy-ethoxy)-phenyl]-2,5-dioxo-imidazolidin-1-yl}-3-methyl-butyramide

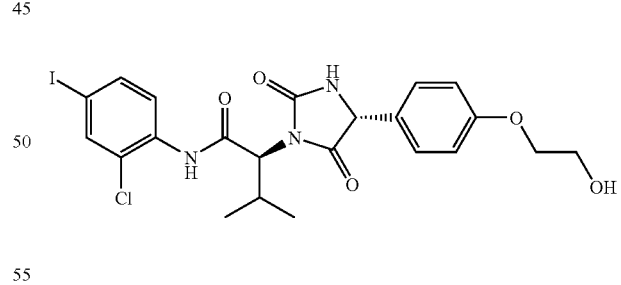

Prepared by the same method as described in example 119 except that (R)-tert-butoxycarbonylamino-{4-[2-(tetrahydro-pyran-2-yloxy)-ethoxy]-phenyl}-acetic acid was used in place of (R)-tert-butoxycarbonylamino-(4-cyclopropylmethoxy-phenyl)-acetic acid. (R)-tert-butoxycarbonylamino-{4-[2-(tetrahydro-pyran-2-yloxy)-ethoxy]-phenyl}-acetic acid was prepared as described in example 48.

HRMS: Obs Mass (M+H$^+$), 572.0433. Calcd. Mass, 572.0444 for $C_{22}H_{24}ClIN_3O_5^+$.

EXAMPLE 121

(S)—N-(2-Chloro-4-iodo-phenyl)-2-{(R)-4-[4-(2-methoxy-ethoxy)-phenyl]-2,5-dioxo-imidazolidin-1-yl}-3-methyl-butyramide

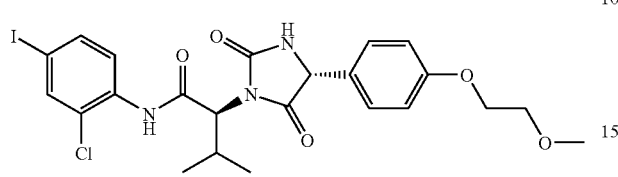

Prepared by the same method as described in example 119 except that (R)-tert-butoxycarbonylamino-[4-(2-methoxy-ethoxy)-phenyl]-acetic acid was used in place of (R)-tert-butoxycarbonylamino-(4-cyclopropylmethoxy-phenyl)-acetic acid. (R)-tert-butoxycarbonylamino-[4-(2-methoxy-ethoxy)-phenyl]-acetic acid was prepared as described in example 80.

HRMS: Obs Mass (M+H$^+$), 586.0586. Calcd. Mass, 586.0600 for $C_{23}H_{26}ClIN_3O_5^+$.

EXAMPLE 122

(S)—N-(2-Chloro-4-iodo-phenyl)-2-{(R)-4-[4-((R)-2,3-dihydroxy-propoxy)-phenyl]-2,5-dioxo-imidazolidin-1-yl}-3-methyl-butyramide

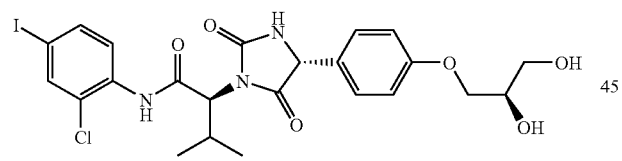

Prepared by the same method as described in example 3 except that (i) 2-chloro-4-iodoaniline was used in place of 4-bromo-2-chloroaniline in step 1, (ii) (S)-2-tert-butoxycarbonylamino-3-methyl-butyric acid was used in place (2S,3S)-2-tert-butoxycarbonylamino-3-phenyl-butyric acid in step 1, and (iii) (R)-tert-butoxycarbonylamino-[4-((S)-2,2-dimethyl-[1,3]dioxolan-4-ylmethoxy)-phenyl]-acetic acid was used in place of (R)-tert-butoxycarbonylamino-[4-(2-tert-butoxy-ethoxy)-phenyl]-acetic acid in step 2. (R)-tert-Butoxycarbonylamino-[4-((S)-2,2-dimethyl-[1,3]dioxolan-4-ylmethoxy)-phenyl]-acetic acid was prepared and used as described in example 114.

HRMS: Obs Mass (M+Na$^+$), 624.0367. Calcd. Mass, 624.0369 for $C_{23}H_{25}ClIN_3NaO_6^+$.

EXAMPLE 123

(S)—N-(2-Chloro-4-iodo-phenyl)-2-{(R)-4-[4-((S)-2,3-dihydroxy-propoxy)-phenyl]-2,5-dioxo-imidazolidin-1-yl}-3-methyl-butyramide

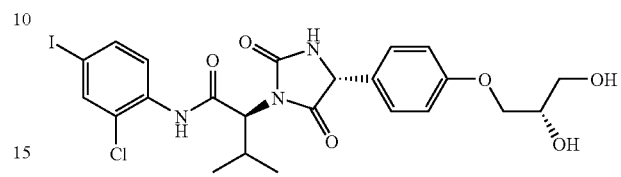

Prepared by the same method as described in example 3 except that (i) 2-chloro-4-iodoaniline was used in place of 4-bromo-2-chloroaniline in step 1, (ii) (S)-2-tert-butoxycarbonylamino-3-methyl-butyric acid was used in place (2S, 3S)-2-tert-butoxycarbonylamino-3-phenyl-butyric acid in step 1, and (iii) (R)-tert-butoxycarbonylamino-[4-((R)-2,2-dimethyl-[1,3]dioxolan-4-ylmethoxy)-phenyl]-acetic acid was used in place of (R)-tert-butoxycarbonylamino-[4-(2-tert-butoxy-ethoxy)-phenyl]-acetic acid in step 2. (R)-tert-Butoxycarbonylamino-[4-((R)-2,2-dimethyl-[1,3]dioxolan-4-ylmethoxy)-phenyl]-acetic acid was prepared and used as described in example 116.

HRMS: Obs Mass (M+H$^+$), 602.0541. Calcd. Mass, 602.0550 for $C_{23}H_{26}ClIN_3O_6^+$.

EXAMPLE 124

(S)—N-(2-Chloro-4-iodo-phenyl)-2-[(R)-4-(2,3-dihydro-benzo[1,4]dioxin-6-yl)-2,5-dioxo-imidazolidin-1-yl]-3-methyl-butyramide

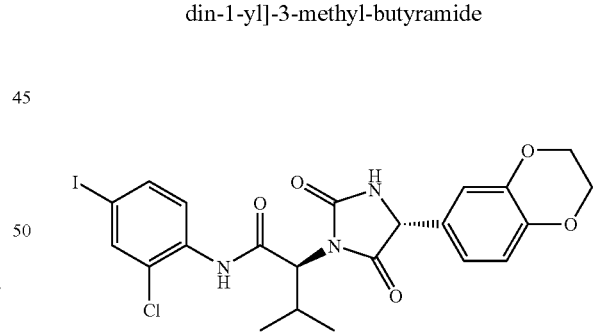

Prepared by the same method as described in example 119 except that (R)-tert-butoxycarbonylamino-(2,3-dihydro-benzo[1,4]dioxin-6-yl)-acetic acid was used in place of (R)-tert-butoxycarbonylamino-(4-cyclopropylmethoxy-phenyl)-acetic acid. (R)-tert-Butoxycarbonylamino-(2,3-dihydro-benzo[1,4]dioxin-6-yl)-acetic acid was prepared as described in example 29.

HRMS: Obs Mass (M+H$^+$), 570.0277. Calcd. Mass, 570.0287 for $C_{22}H_{22}ClIN_3O_5^+$.

EXAMPLE 125

(S)—N-(2-Chloro-4-iodo-phenyl)-2-[(R)-4-(4-dimethylcarbamoylmethoxy-phenyl)-2,5-dioxo-imidazolidin-1-yl]-3-methyl-butyramide

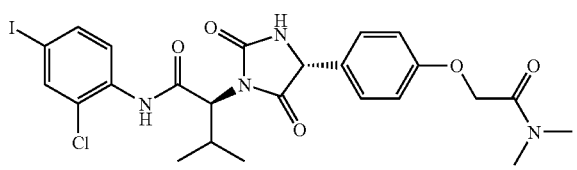

Prepared by the same method as described in example 119 except that (R)-tert-butoxycarbonylamino-(4-dimethylcarbamoylmethoxy-phenyl)-acetic acid was used in place of (R)-tert-butoxycarbonylamino-(4-cyclopropylmethoxy-phenyl)-acetic acid. (R)-tert-Butoxycarbonylamino-(4-dimethylcarbamoylmethoxy-phenyl)-acetic acid was prepared by the same method as used for the preparation of (R)-tert-butyloxycarbonylamino-4-methoxyphenylglycine in example 1 except that 2-chloro-N,N-dimethyl-acetamide was used in place of iodomethane.

HRMS: Obs Mass (M+H$^+$), 613.0703. Calcd. Mass, 613.0709 for $C_{24}H_{27}ClIN_4O_5^+$.

EXAMPLE 126

(S)—N-(2-Chloro-4-iodo-phenyl)-2-{(R)-2,5-dioxo-4-[4-(2-oxo-2-pyrrolidin-1-yl-ethoxy)-phenyl]-imidazolidin-1-yl}-3-methyl-butyramide

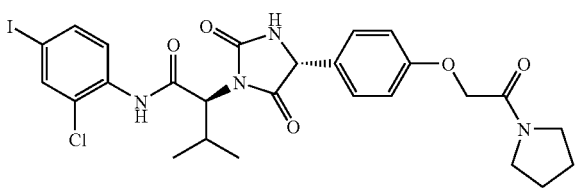

Prepared by the same method as described in example 119 except that (R)-tert-butoxycarbonylamino-[4-(2-oxo-2-pyrrolidin-1-yl-ethoxy)-phenyl]-acetic acid was used in place of (R)-tert-butoxycarbonylamino-(4-cyclopropylmethoxy-phenyl)-acetic acid. (R)-tert-Butoxycarbonylamino-[4-(2-oxo-2-pyrrolidin-1-yl-ethoxy)-phenyl]-acetic acid was prepared by the same method as used for the preparation of (R)-tert-butyloxycarbonylamino-4-methoxyphenylglycine in example 1 except that 2-chloro-1-pyrrolidin-1-yl-ethanone was used in place of iodomethane.

HRMS: Obs Mass (M+H$^+$), 639.0864. Calcd. Mass, 639.0866 for $C_{26}H_{29}ClIN_4O_5^+$.

EXAMPLE 127

(S)-2-[(R)-4-(4-{[Bis-(2-hydroxy-ethyl)-carbamoyl]-methoxy}-phenyl)-2,5-dioxo-imidazolidin-1-yl]-N-(2-chloro-4-iodo-phenyl)-3-methyl-butyramide

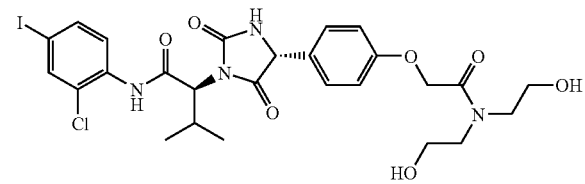

Prepared by the same method as described in example 119 except that (R)-[4-(2-{bis-[2-(tert-butyl-dimethyl-silanyloxy)-ethyl]-amino}-acetoxy)-phenyl]-tert-butoxycarbonylamino-acetic acid was used in place of (R)-tert-butoxycarbonylamino-(4-cyclopropylmethoxy-phenyl)-acetic acid. (R)-[4-(2-{Bis-[2-(tert-butyl-dimethyl-silanyloxy)-ethyl]-amino}-acetoxy)-phenyl]-tert-butoxycarbonylamino-acetic acid was prepared as described in example 62.

HRMS: Obs Mass (M+Na$^+$), 695.0739. Calcd. Mass, 695.0740 for $C_{26}H_{30}ClIN_4NaO_7^+$.

EXAMPLE 128

(2S,3S)-2-{(R)-4-[4-(2-Hydroxy-ethoxy)-phenyl]-2,5-dioxo-imidazolidin-1-yl}-3-methyl-pentanoic acid (2-chloro-4-iodo-phenyl)-amide

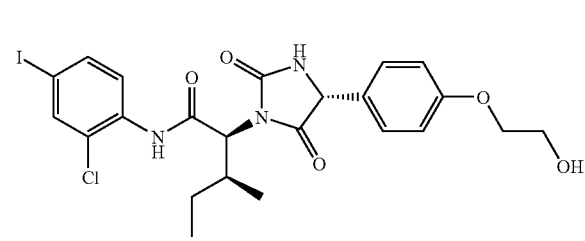

Prepared by the same method as described in example 3 except that 2-chloro-4-iodoaniline was used in place of 4-bromo-2-chloroaniline and (2S,3S)-2-tert-butoxycarbonylamino-3-methyl-pentanoic acid was used in place of (2S,3S)-2-tert-butoxycarbonylamino-3-phenyl-butyric acid in step 1.

HRMS: Obs Mass (M+H$^+$), 586.0603. Calcd. Mass, 586.0600 for $C_{23}H_{26}ClIN_3O_5^+$.

EXAMPLE 129

(2S,3S)-2-[(R)-4-(2,3-Dihydro-benzo[1,4]dioxin-6-yl)-2,5-dioxo-imidazolidin-1-yl]-3-methyl-pentanoic acid (2-chloro-4-iodo-phenyl)-amide

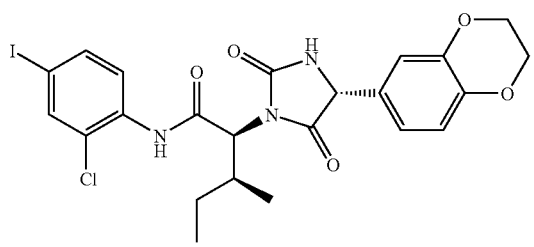

Prepared by the same method as described in example 128 except that (R)-tert-butoxycarbonylamino-(2,3-dihydro-benzo[1,4]dioxin-6-yl)-acetic acid was used in place of (R)-tert-butoxycarbonylamino-[4-(2-tert-butoxy-ethoxy)-phenyl]-acetic acid. (R)-tert-Butoxycarbonylamino-(2,3-dihydro-benzo[1,4]dioxin-6-yl)-acetic acid was prepared as described in example 29.

HRMS: Obs Mass (M+H$^+$), 584.0438. Calcd. Mass, 584.0444 for $C_{23}H_{24}ClIN_3O_5^+$.

EXAMPLE 130

(2S,3R)—N-(2-Chloro-4-iodo-phenyl)-2-{(R)-4-[4-(2-hydroxy-ethoxy)-phenyl]-2,5-dioxo-imidazolidin-1-yl}-3-methoxy-butyramide

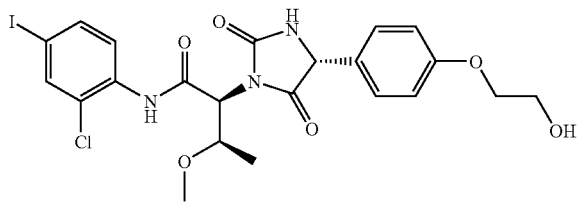

Prepared by the same method as described in example 72 except that 2-fluoro-4-iodoaniline was used in place of 2-chloro-4-iodoaniline and (2S,3R)-2-tert-butoxycarbonylamino-3-methoxy-butyric acid was used in place of (S)-2-tert-butoxycarbonylamino-3-thiophen-2-yl-propionic acid in step 1.

LC-MS: Obs Mass (M+H$^+$), 588; Calcd. Mass, 588 for $C_{22}H_{24}ClIN_3O_6^+$.

EXAMPLE 131

(2S,3S)-2-{(R)-4-[4-(2-Methoxy-ethoxy)-phenyl]-2,5-dioxo-imidazolidin-1-yl}-3-methyl-pentanoic acid (2-chloro-4-iodo-phenyl)-amide

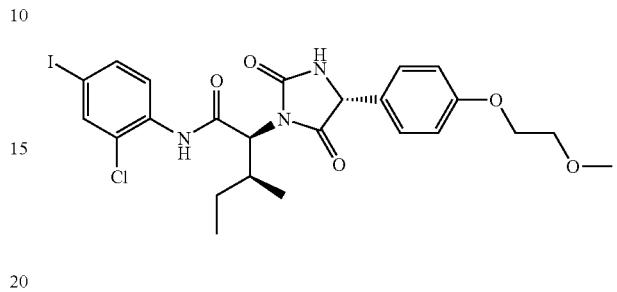

Prepared by the same method as described in example 3 except that (i) 2-chloro-4-iodoaniline was used in place of 4-bromo-2-chloroaniline in step 1, (ii) (2S,3S)-2-tert-butoxycarbonylamino-3-methyl-pentanoic acid was used in place (2S,3S)-2-tert-butoxycarbonylamino-3-phenyl-butyric acid in step 1, and (iii) (R)-tert-butoxycarbonylamino-[4-(2-methoxy-ethoxy)-phenyl]-acetic acid was used in place of (R)-tert-butoxycarbonylamino-[4-(2-tert-butoxy-ethoxy)-phenyl]-acetic acid in step 2. (R)-tert-Butoxycarbonylamino-[4-(2-methoxy-ethoxy)-phenyl]-acetic acid was prepared as described in example 80.

HRMS: Obs Mass (M+H$^+$), 600.0758. Calcd. Mass, 600.0757 for $C_{24}H_{28}ClIN_3O_5^+$.

EXAMPLE 132

(2S,3R)—N-(2-Chloro-4-iodo-phenyl)-2-{(R)-4-[4-((R)-2,3-dihydroxy-propoxy)-phenyl]-2,5-dioxo-imidazolidin-1-yl}-3-methoxy-butyramide

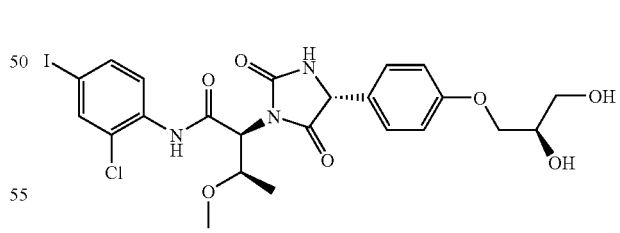

Prepared by the same method as described in example 114 except that (i) (2S,3R)-2-tert-butoxycarbonylamino-3-methoxy-butyric acid was used in place (2S,3S)-2-tert-butoxycarbonylamino-3-phenyl-butyric acid.

LC-MS: Obs Mass (M+H$^+$), 618; Calcd. Mass, 618 for $C_{23}H_{26}ClIN_3O_7^+$.

EXAMPLE 133

(2S,3S)—N-(4-Iodo-2-methyl-phenyl)-2-[(R)-4-(4-methoxy-phenyl)-2,5-dioxo-imidazolidin-1-yl]-3-phenyl-butyramide

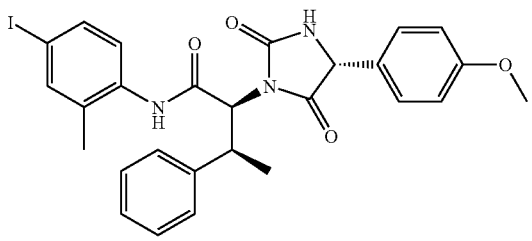

Prepared by the same method as described in example 1 except that 4-iodo-2-methyl-aniline was used in place of 4-bromoaniline in step 2.

HRMS: Obs Mass (M+H$^+$), 584.1042. Calcd. Mass, 584.1041 for $C_{27}H_{27}IN_3O_4^+$.

EXAMPLE 134

(2S,3S)-2-{(R)-4-[4-(2-Hydroxy-ethoxy)-phenyl]-2,5-dioxo-imidazolidin-1-yl}-N-(4-iodo-2-methyl-phenyl)-3-phenyl-butyramide

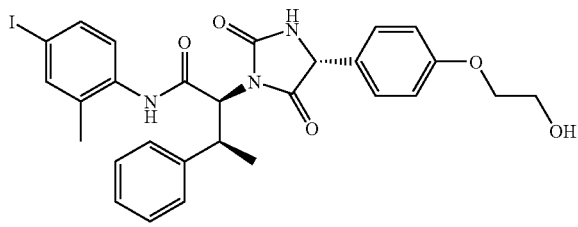

Prepared by the same method as described in example 48 except that 4-iodo-2-methylaniline was used in place of 2-fluoro-4-iodoaniline in step 2.

HRMS: Obs. Mass (M+H$^+$), 614.1135. Calcd. Mass, 614.1147 for $C_{28}H_{29}IN_3O_5^+$.

EXAMPLE 135

(2S,3S)—N-(4-Iodo-2-methyl-phenyl)-2-{(R)-4-[4-(2-methoxy-ethoxy)-phenyl]-2,5-dioxo-imidazolidin-1-yl}-3-phenyl-butyramide

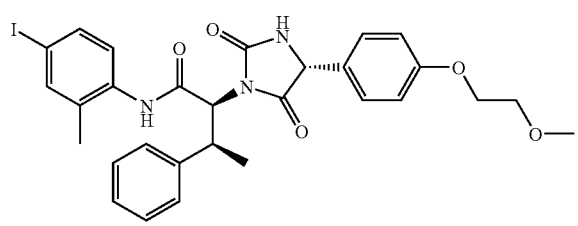

Prepared by the same method as described in example 48 except that (i) 4-iodo-2-methylaniline was used in place of 2-fluoro-4-iodoaniline in step 2, and (ii) (R)-tert-butoxycarbonylamino-[4-(2-methoxy-ethoxy)-phenyl]-acetic acid was used in place of (R)-tert-butoxycarbonylamino-{4-[2-(tetrahydro-pyran-2-yloxy)-ethoxy]-phenyl}-acetic acid. (R)-tert-Butoxycarbonylamino-[4-(2-methoxy-ethoxy)-phenyl]-acetic acid was prepared as described in example 80.

HRMS: Obs Mass (M+H$^+$), 628.1293. Calcd. Mass, 628.1303 for $C_{29}H_{31}IN_3O_5^+$.

EXAMPLE 136

(2S,3S)—N-(4-Iodo-2-methyl-phenyl)-2-((R)-4-{4-[2-(2-methoxy-ethoxy)-ethoxy]-phenyl}-2,5-dioxo-imidazolidin-1-yl)-3-phenyl-butyramide

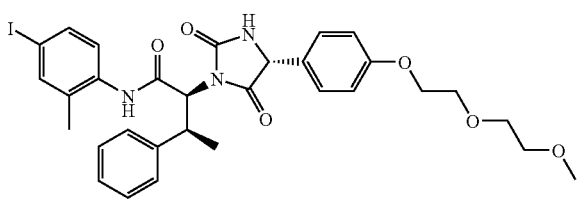

Prepared by the same method as described in example 48 except that (i) 4-iodo-2-methylaniline was used in place of 2-fluoro-4-iodoaniline in step 2, and (ii) (R)-tert-butoxycarbonylamino-[4-(2-{2-methoxy-ethoxy}-ethoxy)-phenyl]-acetic acid was used in place of (R)-tert-butoxycarbonylamino-{4-[2-(tetrahydro-pyran-2-yloxy)-ethoxy]-phenyl}-acetic acid. (R)-tert-Butoxycarbonylamino-[4-(2-{2-methoxy-ethoxy}-ethoxy)-phenyl]-acetic acid was prepared as described in example 48 except that 1-(2-bromo-ethoxy)-2-methoxy-ethane was used in place of 2-(2-bromo-ethoxy)-tetrahydropyran.

HRMS: Obs Mass (M+H$^+$), 672.1556. Calcd. Mass, 672.1565 for $C_{31}H_{35}IN_3O_6^+$.

EXAMPLE 137

(2S,3S)—N-(4-Ethynyl-phenyl)-2-[(R)-4-(4-methoxy-phenyl)-2,5-dioxo-imidazolidin-1-yl]-3-phenyl-butyramide

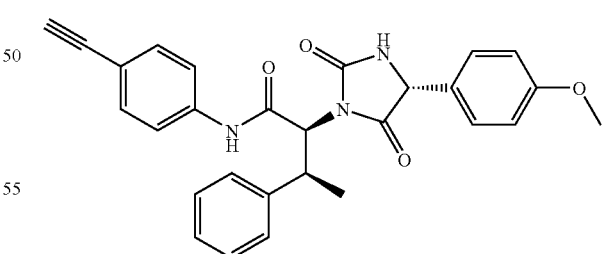

Prepared by the same method as described in example 1 except that (i) 4-ethynylaniline was used in place of 4-bromoaniline in step 2, (ii) (3-dimethylamino-propyl)-ethyl-carbodiimide hydrochloride was used as the coupling reagent in place of O-benzotriazol-1-yl-N,N,N',N'-tetramethyluronium hexaflurorophosphate in step 4, and (iii) formic acid was used to cleave the tert-butyloxycarbonyl protecting group in steps 3 and 5 as described below.

Preparation of (2S,3S)-2-amino-N-(4-ethynyl-phenyl)-3-phenyl-butyramide:

A suspension of [(1S,2S)-1-(4-ethynyl-phenylcarbamoyl)-2-phenyl-propyl]-carbamic acid tert-butyl ester (300 mg, 0.79 mmol) in formic acid (5 mL) was heated to 50° C. for 1 hour. The reaction was concentrated in vacuo, basified with saturated aqueous sodium hydrogen carbonate and extracted with ethyl acetate (2×20 mL). The combined organic extracts were washed with water, brine, dried over sodium sulfate, filtered and concentrated in vacuo to give (2S,3S)-2-amino-N-(4-ethynyl-phenyl)-3-phenyl-butyramide as a foam (214 mg, 92%).

HRMS: Obs Mass (M+Na$^+$), 490.1731. Calcd. Mass, 490.1737 for $C_{28}H_{25}N_3NaO_4{}^+$.

EXAMPLE 138

(S)—N-(4-Ethynyl-2-fluoro-phenyl)-2-{(R)-4-[4-(2-methoxy-ethoxy)-phenyl]-2,5-dioxo-imidazolidin-1-yl}-3-phenyl-propionamide

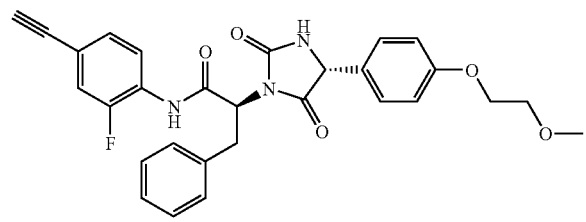

Prepared by the same method as described in example 140 except that (2S)-2-tert-butoxycarbonylamino-3-phenyl-propanoic acid was used in place of (2S,3S)-2-tert-butoxycarbonylamino-3-phenyl-butyric acid and (R)-tert-butoxycarbonylamino-[4-(2-methoxy-ethoxy)-phenyl]-acetic acid was used in place of (R)-tert-butoxycarbonylamino-{4-[2-(tetrahydro-pyran-2-yloxy)-ethoxy]-phenyl}-acetic acid. (R)-tert-Butoxycarbonylamino-[4-(2-methoxy-ethoxy)-phenyl]-acetic acid was prepared as described in example 80.

HRMS: Obs Mass (M+H$^+$), 516.1932. Calcd. Mass, 516.1929 for $C_{29}H_{27}FN_3O_5{}^+$.

EXAMPLE 139

(2S,3S)-2-((R)-2,5-Dioxo-4-phenyl-imidazolidin-1-yl)-N-(4-ethynyl-2-fluoro-phenyl)-3-phenyl-butyramide

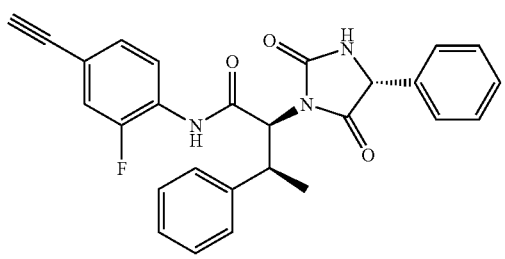

Prepared by the same method as described in example 140 except that (R)-tert-butoxycarbonylamino-phenyl-acetic acid was used in place of (R)-tert-butoxycarbonylamino-{4-[2-(tetrahydro-pyran-2-yloxy)-ethoxy]-phenyl}-acetic acid.

HRMS: Obs Mass (M+Na$^+$), 478.1529. Calcd. Mass, 478.1537 for $C_{27}H_{22}FN_3NaO_3{}^+$.

EXAMPLE 140

(3S)—N-(4-Ethynyl-2-fluoro-phenyl)-2-{(R)-4-[4-(2-hydroxy-ethoxy)-phenyl]-2,5-dioxo-imidazolidin-1-yl}-3-phenyl-butyramide, isomer 1

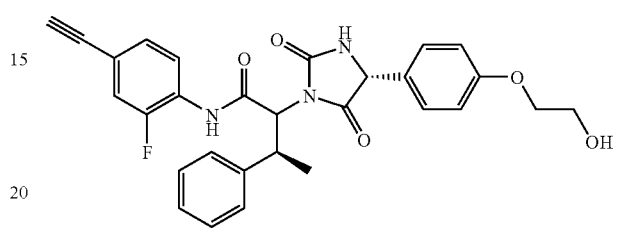

Prepared by the same method as described in example 48 except that (i) after step 3, and prior to step 4, (2S,3S)-2-amino-N-(2-fluoro-4-iodo-phenyl)-3-phenyl-butyramide was converted to (2S,3S)-2-amino-N-(2-fluoro-4-trimethylsilanylethynyl-phenyl)-3-phenyl-butyramide under the conditions described below, and (ii) after initial purification in step 6 the product was subjected to chiral HPLC separation as described below. The trimethylsilyl group introduced in step 3 was subsequently removed during step 5 of the synthesis, concomitant with removal of the tert-butyloxycarbonyl protecting group.

Preparation of (2S,3S)-2-amino-N-(4-ethynyl-2-fluoro-phenyl)-3-phenyl-butyramide:

A solution of (2S,3S)-2-amino-N-(2-fluoro-4-iodo-phenyl)-3-phenyl-butyramide (1.00 g, 2.51 mmol) in triethylamine (1.5 mL, 10.8 mmol) was thoroughly degassed with argon, bis-dichlorotriphenylphosphine palladium(II) (20.3 mg, 0.05 mmol) added followed by copper iodide (9.8 mg, 0.05 mmol) and trimethylsilylacetylene (277 mg, 2.77 mmol) and the mixture stirred under argon at ambient temperature for 3 hours. Additional triethylamine (1.5 mL, 10.8 mmol) was added to form a stirrable reaction mixture and stirring continued for an additional 20 hours. The reaction mixture was diluted with diethyl ether and a small amount of Celite added prior to filtration through Celite. The Celite was eluted with diethyl ether (4×20 mL) and the combined organic filtrates concentrated in vacuo. The resulting green oil was dissolved in a small amount of diethyl ether and diluted with hexanes (10 mL) to induce crystallization. The product was isolated by filtration, washed with hexanes and dried in vacuo to afford (2S,3S)-2-amino-N-(2-fluoro-4-trimethylsilanylethynyl-phenyl)-3-phenyl-butyramide as a grey solid (610 mg, 66%). A second crop of product was obtained by reprocessing of the mother liquors from the initial crystallization (168 mg, 18%).

HRMS: Obs. Mass, 369.1793. Calcd. Mass, 369.1793 for $C_{21}H_{26}FN_2OSi^+$. Chiral HPLC separation:

A sample of (3S)—N-(4-ethynyl-2-fluoro-phenyl)-2-{(R)-4-[4-(2-hydroxy-ethoxy)-phenyl]-2,5-dioxo-imidazolidin-1-yl}-3-phenyl-butyramide (22 mg, 0.43 mmol) was purified by chiral HPLC using a 2.0 cm×25 cm Daicel OD column eluted with 1:1 v/v hexanes in absolute ethanol at 5 mL per minute using UV detection at 260 nm to monitor the eluant for presence of product. The first eluted product was collected and concentrated in vacuo to afford (3S)—N-(4-ethynyl-2-fluoro-phenyl)-2-{(R)-4-[4-(2-hydroxy-ethoxy)-phenyl]-2,5-dioxo-imidazolidin-1-yl}-3-phenyl-butyramide, isomer 1 as a white solid (6.1 mg, 28%).

HRMS: Obs. Mass (M+H$^+$), 516.1926. Calcd. Mass, 516.1929 for $C_{29}H_{27}FN_3O_5^+$.

EXAMPLE 141

(3S)—N-(4-Ethynyl-2-fluoro-phenyl)-2-{(R)-4-[4-(2-hydroxy-ethoxy)-phenyl]-2,5-dioxo-imidazolidin-1-yl}-3-phenyl-butyramide, isomer 2

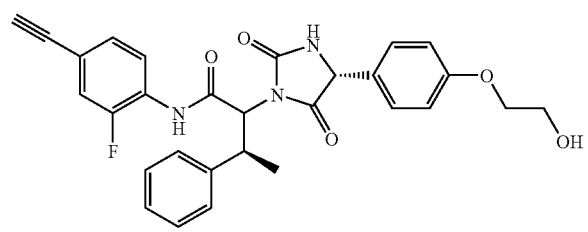

Prepared by the same method as described in example 140 except that the second eluted product from the chiral HPLC purification step was collected and concentrated in vacuo to afford (3S)—N-(4-ethynyl-2-fluoro-phenyl)-2-{(R)-4-[4-(2-hydroxy-ethoxy)-phenyl]-2,5-dioxo-imidazolidin-1-yl}-3-phenyl-butyramide, isomer 2 as a colorless solid (7 mg, 32%).

HRMS: Obs. Mass (M+H$^+$), 516.1931. Calcd. Mass, 516.1929 for $C_{29}H_{27}FN_3O_5^+$.

EXAMPLE 142

(3S)—N-(4-Ethynyl-2-fluoro-phenyl)-2-{(R)-4-[4-(2-methoxy-ethoxy)-phenyl]-2,5-dioxo-imidazolidin-1-yl}-3-phenyl-butyramide, isomer 1

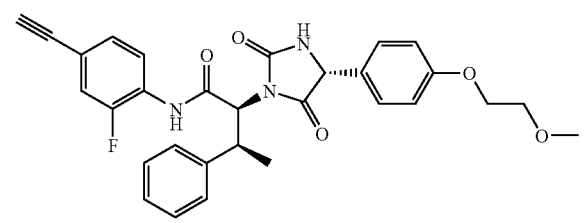

Prepared by the same method as described in example 140 except that (R)-tert-butoxycarbonylamino-[4-(2-methoxy-ethoxy)-phenyl]-acetic acid was used in place of (R)-tert-butoxycarbonylamino-{4-[2-(tetrahydro-pyran-2-yloxy)-ethoxy]-phenyl}-acetic acid. (R)-tert-Butoxycarbonylamino-[4-(2-methoxy-ethoxy)-phenyl]-acetic acid was prepared as described in example 80. Purification of the final product was performed by chromatography over silica gel gradient eluted with 0 to 30% v/v ethyl acetate in hexanes. The first eluted product was collected and concentrated in vacuo, then precipitated from ethyl ether (1 mL) containing a small amount of dichloromethane with hexanes (10 mL). The precipitated solid was collected by filtration and dried to afford (3S)—N-(4-ethynyl-2-fluoro-phenyl)-2-{(R)-4-[4-(2-methoxy-ethoxy)-phenyl]-2,5-dioxo-imidazolidin-1-yl}-3-phenyl-butyramide, isomer 1 as a colorless solid (19%).

HRMS: Obs Mass (M+Na$^+$), 552.1905. Calcd. Mass, 552.1905 for $C_{30}H_{28}FN_3NaO_5^+$.

EXAMPLE 143

(3S)—N-(4-Ethynyl-2-fluoro-phenyl)-2-{(R)-4-[4-(2-methoxy-ethoxy)-phenyl]-2,5-dioxo-imidazolidin-1-yl}-3-phenyl-butyramide, isomer 2

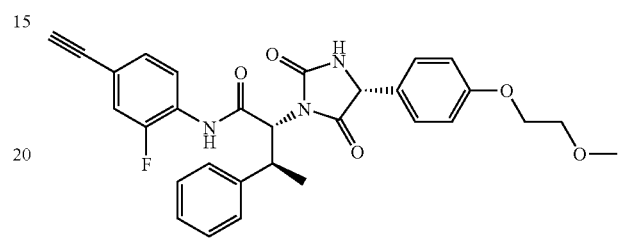

Prepared by the same method as described in example 142 except that the second eluted product from the chromatographic purification of the final reaction product was collected. The second eluted product was collected and concentrated in vacuo, then precipitated from ethyl ether (1 mL) containing a small amount of dichloromethane with hexanes (10 mL). The precipitated solid was collected by filtration and dried to afford (3S)—N-(4-ethynyl-2-fluoro-phenyl)-2-{(R)-4-[4-(2-methoxy-ethoxy)-phenyl]-2,5-dioxo-imidazolidin-1-yl}-3-phenyl-butyramide, isomer 2 as a colorless solid (10%).

HRMS: Obs Mass (M+Na$^+$), 552.1906. Calcd. Mass, 552.1905 for $C_{30}H_{28}FN_3NaO_5^+$.

EXAMPLE 144

(S)—N-(4-Ethynyl-2-fluoro-phenyl)-2-((R)-4-{4-[2-(2-methoxy-ethoxy)-ethoxy]-phenyl}-2,5-dioxo-imidazolidin-1-yl)-3-phenyl-butyramide

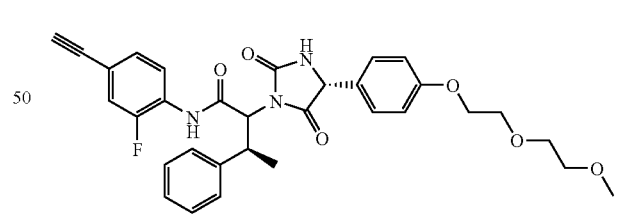

Prepared by the same method as described in example 140 except that (R)-tert-butoxycarbonylamino-{4-[2-(2-methoxy-ethoxy)-ethoxy]-phenyl}-acetic acid was used in place of (R)-tert-butoxycarbonylamino-{4-[2-(tetrahydro-pyran-2-yloxy)-ethoxy]-phenyl}-acetic acid. (R)-tert-Butoxycarbonylamino-{4-[2-(2-methoxy-ethoxy)-ethoxy]-phenyl}-acetic acid was prepared as described in example 48 except that 1-(2-bromo-ethoxy)-2-methoxy-ethane was used in place of 2-(2-bromo-ethoxy)-tetrahydropyran.

HRMS: Obs Mass (M+Na$^+$), 596.2168. Calcd. Mass, 596.2167 for $C_{32}H_{32}FN_3NaO_6^+$.

EXAMPLE 145

(2S,3S)-2-{(R)-2,5-Dioxo-4-[4-(2-oxo-2-pyrrolidin-1-yl-ethoxy)-phenyl]-imidazolidin-1-yl}-N-(4-ethynyl-2-fluoro-phenyl)-3-phenyl-butyramide

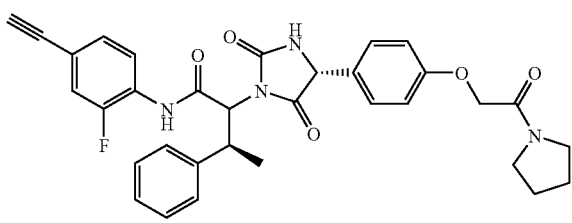

Prepared by the same method as described in example 140 except that (R)-tert-butoxycarbonylamino-[4-(2-oxo-2-pyrrolidin-1-yl-ethoxy)-phenyl]-acetic acid was used in place of (R)-tert-butoxycarbonylamino-{4-[2-(tetrahydro-pyran-2-yloxy)-ethoxy]-phenyl}-acetic acid. (R)-tert-Butoxycarbonylamino-[4-(2-oxo-2-pyrrolidin-1-yl-ethoxy)-phenyl]-acetic acid was prepared as described in example 126.

HRMS: Obs Mass (M+H$^+$), 583.2352. Calcd. Mass, 583.2351 for $C_{33}H_{32}FN_4O_5^+$.

EXAMPLE 146

(S)—N-(2-Chloro-4-ethynyl-phenyl)-2-{4-[4-(2-hydroxy-ethoxy)-phenyl]-2,5-dioxo-imidazolidin-1-yl}-3-phenyl-propionamide, isomer 1

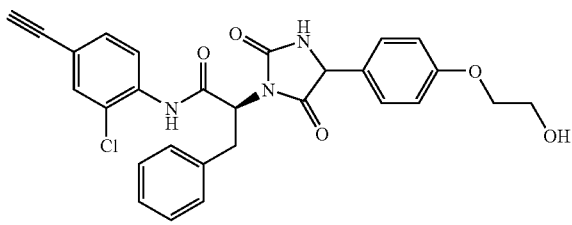

Prepared as described below starting from (S)-2-amino-(2-chloro-4-iodo-phenyl)-3-phenyl-propionamide. (S)-2-Amino-(2-chloro-4-iodo-phenyl)-3-phenyl-propionamide was prepared by the same method as described in step 1 of example 3 except that 2-chloro-4-iodo-aniline was used in place of 4-bromo-2-chloro-aniline and (S)-2-tert-butoxycarbonylamino-3-phenyl-propionic acid was used in place of (S,S)-2-tert-butoxycarbonylamino-3-phenyl-butyric acid.

Step 2: To a dry flask were added (S)-2-amino-(2-chloro-4-iodo-phenyl)-3-phenyl-propionamide (980 mg, 2.44 mmol), bis-dichlorotriphenylphosphine palladium (19.8 mg, 0.0489 mmol), and copper iodide (9.5 mg, 0.049 mmol). To this mixture was added trimethylsilylacetylene (269.7 mg, 2.69 mmol) in dry triethylamine (1.46 mL). Dry dichloromethane (1 mL) was added after 30 minutes. After 3 hours additional bis-dichlorotriphenylphosphine palladium (40 mg, 0.099 mmol) and copper iodide (20 mg, 0.099 mmol) were added. After 1 hour the reaction mixture was diluted with a 1:1 v/v mixture of diethyl ether/dichloromethane and passed through a bed of silica gel and the silica gel then eluted with a 2:3 v/v mixture of diethyl ether/dichloromethane. The eluant was concentrated in vacuo and the crude residue was purified by chromatography over silica gel gradient eluted with 5 to 30% v/v diethyl ether in hexanes. The pooled fractions containing product were concentrated to give (S)-2-amino-N-(2-chloro-4-trimethylsilanylethynyl-phenyl)-3-phenyl-propionamide as a white solid (820 mg 90% yield).

Step 3: (S)-2-Amino-N-(2-chloro-4-trimethylsilanylethynyl-phenyl)-3-phenyl-propionamide was coupled to (R)-tert-butoxycarbonylamino-{4-[2-(tetrahydro-pyran-2-yloxy)-ethoxy]-phenyl}-acetic acid (prepared as described in example 48) using the same method as described in step 4 of example 1 to give ((S)-[(S)-1-(2-chloro-4-trimethylsilanylethynyl-phenylcarbamoyl)-2-phenyl-ethylcarbamoyl]-{4-[2-(tetrahydro-pyran-2-yloxy)-ethoxy]-phenyl}-methyl)-carbamic acid tert-butyl ester.

Step 4: ((S)-[(S)-1-(2-Chloro-4-trimethylsilanylethynyl-phenylcarbamoyl)-2-phenyl-ethylcarbamoyl]-{4-[2-(tetrahydro-pyran-2-yloxy)-ethoxy]-phenyl}-methyl)-carbamic acid tert-butyl ester. (491 mg, 0.656 mmol) was dissolved into formic acid (7.1 mL) and heated for 30 minutes at 40° C. The temperature was then increased to between 50 and 55° C. for 3 hours. The reaction mixture was then concentrated in vacuo, the residue taken into dichloromethane, carefully neutralized with saturated aqueous sodium bicarbonate and then extracted into dichloromethane. The combined organic extracts were dried over sodium sulfate, concentrated in vacuo and the crude product purified by chromatography over silica gel gradient eluted with between 0.5 and 5% v/v methanol in dichloromethane. The fractions containing the product were concentrated to give a white residue that was triturated in 1:1 ether/hexanes (20 mL), filtered and dried to give (S)-2-{(S)-2-amino-2-[4-(2-hydroxy-ethoxy)-phenyl]-acetylamino}-N-[2-chloro-4-(3-oxo-prop-1-ynyl)-phenyl]-3-phenyl-propionamide (240 mg, 70%).

Step 5: Cyclization with diphosgene was performed using the same method as described in step 6 of example 1 except that after work up the crude material (250 mg) was dissolved in methanol (11.3 mL), cooled in an ice bath and treated with sodium borohydride (123 mg, 3.28 mmol). After 15 minutes the reaction was treated with 1.5 N aqueous potassium hydrogen sulfate solution and extracted with ethyl acetate (3×50 mL). The combined organic extracts were washed with 1.5 N aqueous potassium hydrogen sulfate solution (2×50 mL) and water (2×50 mL). The organic solution was dried over sodium sulfate, filtered and concentrated and gave the crude mixture of diastereomers.

Step 6: The crude mixture of diastereomers was purified by chromatography using a Daicel OD column eluted with 50% v/v methanol in 10 mmol aqueous ammonium acetate. The faster running component was concentrated in vacuo, dissolved in ethyl acetate (100 mL), the organic solution was washed with 5% w/v aqueous sodium bicarbonate solution (3×50 mL) and then the aqueous layers were combined and back extracted with ethyl acetate (2×50 mL). The combined organic extracts were dried over sodium sulfate and concentrated to give (S)—N-(2-Chloro-4-ethynyl-phenyl)-2-{4-[4-(2-hydroxy-ethoxy)-phenyl]-2,5-dioxo-imidazolidin-1-yl}-3-phenyl-propionamide, isomer 1 (64 mg, 25.5% yield).

HRMS: Obs Mass (M+H$^+$), 518.1477. Calcd. Mass, 518.1477 for $C_{28}H_{25}ClN_3O_5^+$.

EXAMPLE 147

(S)—N-(2-Chloro-4-ethynyl-phenyl)-2-{4-[4-(2-hydroxy-ethoxy)-phenyl]-2,5-dioxo-imidazolidin-1-yl}-3-phenyl-propionamide, isomer 2

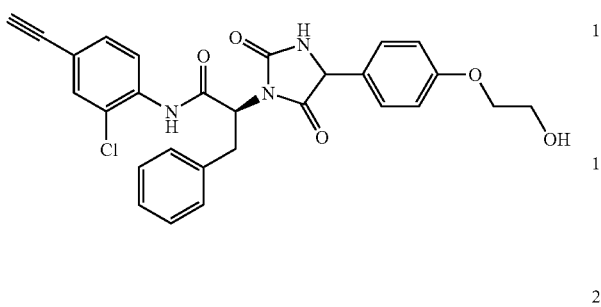

Prepared by the same procedure as described in example 146 except that in step 6 the slower running component was collected to give after washing and drying (S)—N-(2-chloro-4-ethynyl-phenyl)-2-{4-[4-(2-hydroxy-ethoxy)-phenyl]-2,5-dioxo-imidazolidin-1-yl}-3-phenyl-propionamide, isomer 2 (42 mg, 18.5% yield).

HRMS: Obs Mass (M+H$^+$), 518.1472. Calcd. Mass, 518.1477 for $C_{28}H_{25}ClN_3O_5^+$.

EXAMPLE 148

(S)—N-(2-Chloro-4-ethynyl-phenyl)-2-{(R)-4-[4-(2-methoxy-ethoxy)-phenyl]-2,5-dioxo-imidazolidin-1-yl}-3-phenyl-propionamide

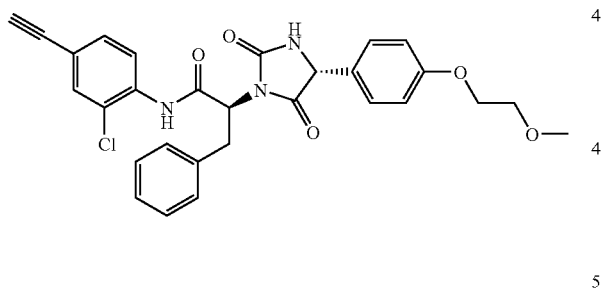

Prepared by the same method as described in example 146 except that: (i) in step 3 (R)-tert-butoxycarbonylamino-[4-(2-methoxy-ethoxy)-phenyl]-acetic acid was used in place of (R)-tert-butoxycarbonylamino-{4-[2-(tetrahydro-pyran-2-yloxy)-ethoxy]-phenyl}-acetic acid. (R)-tert-Butoxycarbonylamino-[4-(2-methoxy-ethoxy)-phenyl]-acetic acid was prepared as described in example 80, (ii) no formyl group was present after treatment with diphosgene in step 5 and so treatment with sodium borohydride was not required, and (iii) no diastereomer was observed after step 5 and so separation of diastereomers by super critical fluid chromatography was not required (step 6 in example 146).

HRMS: Obs Mass (M+H$^+$), 532.1634. Calcd. Mass, 532.1634 for $C_{29}H_{27}ClN_3O_5^+$.

EXAMPLE 149

(2S,3S)—N-(2-Chloro-4-ethynyl-phenyl)-2-{(R)-4-[4-(2-hydroxy-ethoxy)-phenyl]-2,5-dioxo-imidazolidin-1-yl}-3-phenyl-butyramide)

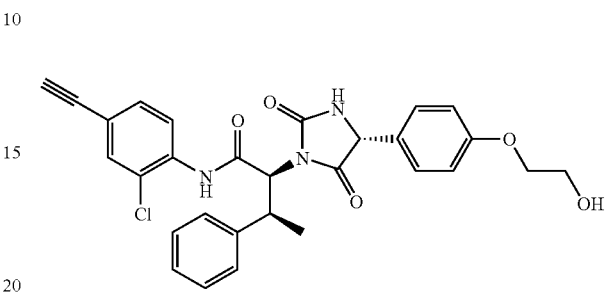

Prepared by the same method as described in example 146 except that (2S,3S)-2-tert-butoxycarbonylamino-3-phenyl-butyric acid was used in place of (S)-2-tert-butoxycarbonylamino-3-phenyl-propionic acid.

HRMS: Obs Mass (M+H$^+$), 532.1637. Calcd. Mass, 532.1634 for $C_{29}H_{27}ClN_3O_5^+$.

EXAMPLE 150

(2S,3S)—N-(2-Chloro-4-ethynyl-phenyl)-2-{(R)-4-[4-(2-methoxy-ethoxy)-phenyl]-2,5-dioxo-imidazolidin-1-yl}-3-phenyl-butyramide

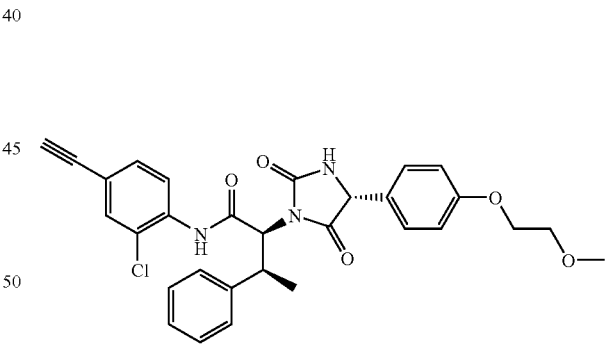

Prepared by the same method as described in example 149 except that (R)-tert-butoxycarbonylamino-[4-(2-methoxy-ethoxy)-phenyl]-acetic acid was used in place of (R)-tert-butoxycarbonylamino-{4-[2-(tetrahydro-pyran-2-yloxy)-ethoxy]-phenyl}-acetic acid. (R)-tert-Butoxycarbonylamino-[4-(2-methoxy-ethoxy)-phenyl]-acetic acid was prepared as described in example 80.

HRMS: Obs Mass (M+H$^+$), 546.1785. Calcd. Mass, 546.1790 for $C_{30}H_{29}ClN_3O_5^+$.

EXAMPLE 151

(2S,3S)—N-(2-Chloro-4-ethynyl-phenyl)-2-((R)-4-{4-[2-(2-methoxy-ethoxy)-ethoxy]-phenyl}-2,5-dioxo-imidazolidin-1-yl)-3-phenyl-butyramide

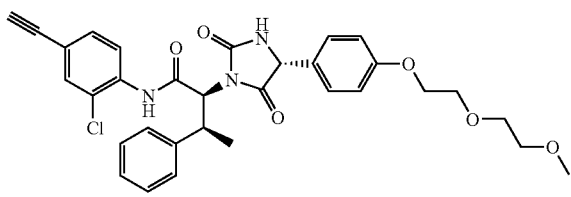

Prepared by the same method as described in example 150 except that (R)-tert-butoxycarbonylamino-{4-[2-(2-methoxy-ethoxy)-ethoxy]-phenyl}-acetic acid was used in place of (R)-tert-butoxycarbonylamino-[4-(2-methoxy-ethoxy)-phenyl]-acetic acid. (R)-tert-Butoxycarbonylamino-{4-[2-(2-methoxy-ethoxy)-ethoxy]-phenyl}-acetic acid was prepared as described in example 48 except that 1-(2-bromo-ethoxy)-2-methoxy-ethane was used in place of 2-(2-bromo-ethoxy)-tetrahydropyran.

HRMS: Obs Mass (M+H$^+$), 590.2053. Calcd. Mass, 590.2053 for $C_{32}H_{33}ClN_3O_6^+$.

EXAMPLE 152

(S)—N-(2-Chloro-4-ethynyl-phenyl)-2-{(R)-4-[4-(2-methoxy-ethoxy)-phenyl]-2,5-dioxo-imidazolidin-1-yl}-3-methyl-butyramide

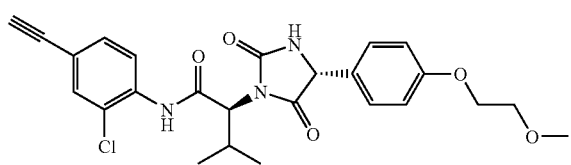

Prepared by the same method as described in example 150 except that (S)-2-tert-butoxycarbonylamino-3-methyl-butyric acid was used in place (2S,3S)-2-tert-butoxycarbonylamino-3-phenyl-butyric acid.

HRMS: Obs Mass (M+Na$^+$), 506.1455. Calcd. Mass, 506.1453 for $C_{25}H_{26}ClN_3NaO_5^+$.

EXAMPLE 153

(2S,3S)-2-{(R)-4-[4-(2-Methoxy-ethoxy)-phenyl]-2,5-dioxo-imidazolidin-1-yl}-3-methyl-pentanoic acid (2-chloro-4-ethynyl-phenyl)-amide

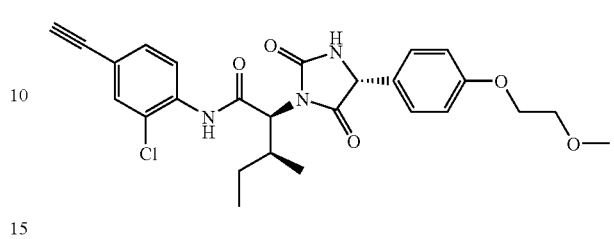

Prepared by the same method as described in example 150 except that (2S,3S)-2-tert-butoxycarbonylamino-3-methyl-pentanoic acid was used in place (2S,3S)-2-tert-butoxycarbonylamino-3-phenyl-butyric acid.

HRMS: Obs Mass (M+Na$^+$), 520.1612. Calcd. Mass, 520.1609 for $C_{26}H_{28}ClN_3NaO_5^+$.

EXAMPLE 154

(2S,3S)—N-(4-Ethynyl-2-methyl-phenyl)-2-{(R)-4-[4-(2-methoxy-ethoxy)-phenyl]-2,5-dioxo-imidazolidin-1-yl}-3-phenyl-butyramide

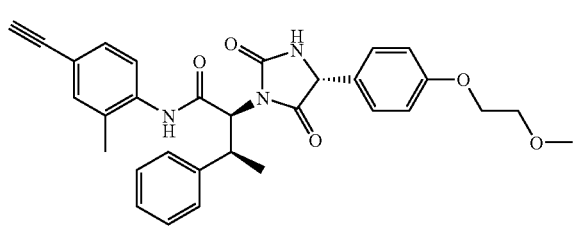

Prepared by the same method as described in example 150 except that 4-iodo-2-methylaniline was used in place of 2-chloro-4-iodomethylaniline.

HRMS: Obs Mass (M+Na$^+$), 548.2154. Calcd. Mass, 548.2156 for $C_{31}H_{31},N_3NaO_5^+$.

EXAMPLE 155

(2S,3S)—N-(4-Ethynyl-2-methyl-phenyl)-2-((R)-4-{4-[2-(2-methoxy-ethoxy)-ethoxy]-phenyl}-2,5-dioxo-imidazolidin-1-yl)-3-phenyl-butyramide

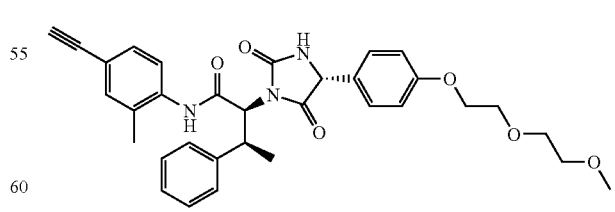

Prepared by the same method as described in example 151 except that 4-iodo-2-methylaniline was used in place of 2-chloro-4-iodomethylaniline.

HRMS: Obs Mass (M+Na$^+$), 592.2411. Calcd. Mass, 592.2418 for $C_{33}H_{35}N_3NaO_6^+$.

EXAMPLE 156

(2S,3S)—N-(4-Cyclopropyl-phenyl)-2-{(R)-4-[4-(2-hydroxy-ethoxy)-phenyl]-2,5-dioxo-imidazolidin-1-yl}-3-phenyl-butyramide

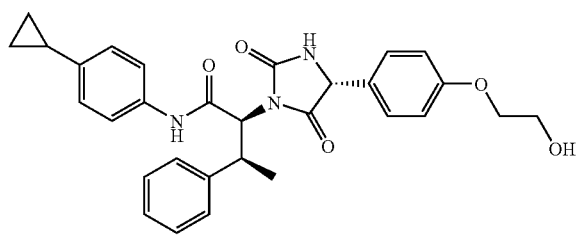

Prepared by the same method as described in example 48 except that 4-cyclopropyl-aniline was used in place of 2-fluoro-4-iodoaniline.

HRMS: Obs Mass (M+H$^+$), 514.2333. Calcd. Mass, 514.2337 for $C_{30}H_{32}N_3O_5^+$.

HRMS: Obs Mass (M+Na$^+$), 536.2153. Calcd. Mass, 536.2156 for $C_{30}H_{31}N_3NaO_5^+$.

EXAMPLE 157

(S)—N-(4-Cyclopropyl-2-fluoro-phenyl)-3-(4-fluoro-phenyl)-2-{(R)-4-[4-(2-hydroxy-ethoxy)-phenyl]-2,5-dioxo-imidazolidin-1-yl}-propionamide

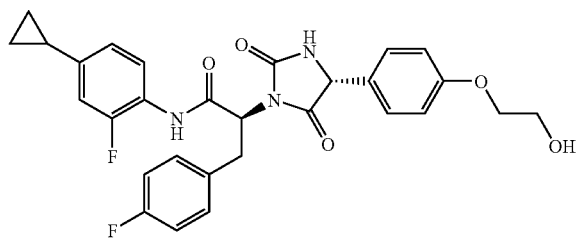

Prepared by the same method as described in example 160 except that (R)-tert-butoxycarbonylamino-{4-[2-(tetrahydro-pyran-2-yloxy)-ethoxy]-phenyl}-acetic was used in place of (R)-tert-butoxycarbonylamino-[4-(2-hydroxy-1-hydroxymethyl-ethoxy)-phenyl]-acetic acid. (R)-tert-Butoxycarbonylamino-{4-[2-(tetrahydro-pyran-2-yloxy)-ethoxy]-phenyl}-acetic acid was prepared as described in example 48.

HRMS: Obs Mass (M+H$^+$), 536.1986. Calcd. Mass, 536.1992 for $C_{29}H_{28}F_2N_3O_5^+$.

EXAMPLE 158

(S)—N-(4-Cyclopropyl-2-fluoro-phenyl)-2-{(R)-4-[4-((R)-2,3-dihydroxy-propoxy)-phenyl]-2,5-dioxo-imidazolidin-1-yl}-3-(4-fluoro-phenyl)-propionamide

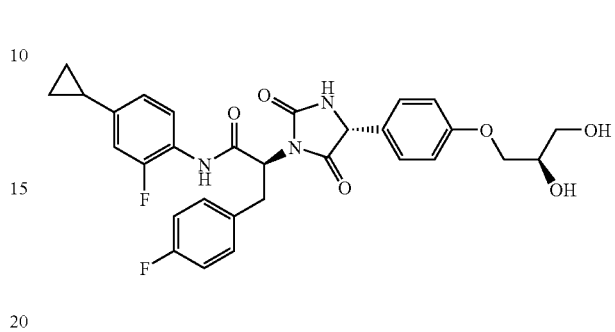

Prepared by the same method as described in example 160 except that (R)-tert-butoxycarbonylamino-[4-((R)-2,2-dimethyl-[1,3]dioxolan-4-ylmethoxy)-phenyl]-acetic acid was used in place of (R)-tert-butoxycarbonylamino-[4-(2-hydroxy-1-hydroxymethyl-ethoxy)-phenyl]-acetic acid. (R)-tert-Butoxycarbonylamino-[4-((R)-2,2-dimethyl-[1,3]dioxolan-4-ylmethoxy)-phenyl]-acetic acid was prepared and used as described in example 114.

HRMS: Obs Mass (M+H$^+$), 566.2099. Calcd. Mass, 566.2097 for $C_{30}H_{30}F_2N_3O_6^+$.

EXAMPLE 159

(S)—N-(4-Cyclopropyl-2-fluoro-phenyl)-2-{(R)-4-[4-((S)-2,3-dihydroxy-propoxy)-phenyl]-2,5-dioxo-imidazolidin-1-yl}-3-(4-fluoro-phenyl)-propionamide

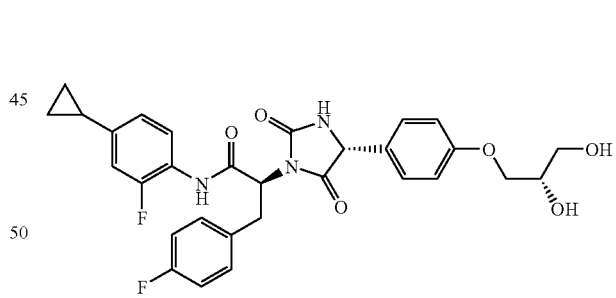

Prepared by the same method as described in example 160 except that (R)-tert-butoxycarbonylamino-[4-((S)-2,2-dimethyl-[1,3]dioxolan-4-ylmethoxy)-phenyl]-acetic acid was used in place of (R)-tert-butoxycarbonylamino-[4-((R)-2,2-dimethyl-[1,3]dioxolan-4-ylmethoxy)-phenyl]-acetic acid. (R)-tert-Butoxycarbonylamino-[4-((S)-2,2-dimethyl-[1,3]dioxolan-4-ylmethoxy)-phenyl]-acetic acid was prepared and used as described in example 116.

HRMS: Obs Mass(M+Na$^+$), 588.1912. Calcd. Mass, 588.1916 for $C_{30}H_{29}F_2N_3NaO_6^+$.

EXAMPLE 160

(S)—N-(4-Cyclopropyl-2-fluoro-phenyl)-3-(4-fluoro-phenyl)-2-{(R)-4-[4-(2-hydroxy-1-hydroxymethyl-ethoxy)-phenyl]-2,5-dioxo-imidazolidin-1-yl}-propionamide

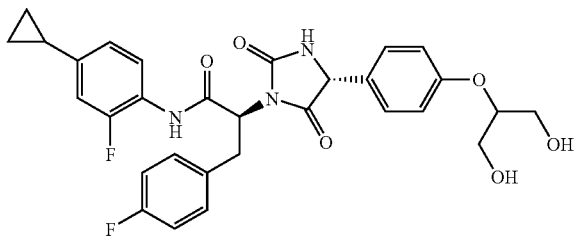

Prepared by the same method as described in example 3 except that (i) (S)-2-tert-butoxycarbonylamino-3-(4-fluoro-phenyl)-propionic acid was used in place of (2S,3S)-2-tert-butoxycarbonylamino-3-phenyl-butyric acid in step 1, (ii) (S)-[1-(2-fluoro-4-iodo-phenylcarbamoyl)-2-(4-fluoro-phenyl)-ethyl]-carbamic acid tert-butyl ester was converted in to (S)-[1-(4-cyclopropyl-2-fluoro-phenylcarbamoyl)-2-(4-fluoro-phenyl)-ethyl]-carbamic acid tert-butyl ester after step 2 and prior to step 3 (using the conditions described below), (iii) (R)-tert-butoxycarbonylamino-[4-(2-hydroxy-1-hydroxymethyl-ethoxy)-phenyl]-acetic acid (prepared as described below) was used in place of (R)-tert-butoxycarbonylamino-{4-[2-(tetrahydro-pyran-2-yloxy)-ethoxy]-phenyl}-acetic acid in step 4, and (iv) the diol functionality contained in (S)-2-{2-amino-2-[4-(2-hydroxy-1-hydroxymethyl-ethoxy)-phenyl]-acetylamino}-N-(4-cyclopropyl-2-fluoro-phenyl)-3-(4-fluoro-phenyl)-propionamide was temporarily protected as the bis-trimethylsilyl ether during step 6 by the same method as described in example 114.

Preparation of (S)-[1-(4-cyclopropyl-2-fluoro-phenylcarbamoyl)-2-(4-fluoro-phenyl)-ethyl]-carbamic acid tert-butyl ester To (S)-[1-(2-fluoro-4-iodo-phenylcarbamoyl)-2-(4-fluoro-phenyl)-ethyl]-carbamic acid tert-butyl ester (4.5 g, 9.0 mmol) and cyclopropylboronic acid (1.0 g, 11.7 mmol) in a mixture of toluene (40 mL) and water (2 mL) were added potassium phosphate tribasic (6.68 g, 31.5 mmol), tricyclohexylphosphine (0.50 g, 1.8 mmol) and palladium acetate (0.20 g, 0.89 mmol). The mixture was heated to 100° C. for 3 hours then additional tricyclohexylphosphine (0.25 g, 0.89 mmol) and palladium acetate (0.10 g, 0.45 mmol) were added. Heating at 100° C. was continued for an additional 3 hours before adding cyclopropylboronic acid (0.2 g, 2.33 mmol) and heating at 100° C. for a final period of 3 hours. The reaction mixture was diluted with ethyl acetate, washed with water (twice), brine (once), dried over sodium sulphate, filtered and concentrated in vacuo. The residue was purified by chromatography over silica gel eluted with 9:1 v/v dichloromethane in hexanes to afford (S)-[1-(4-cyclopropyl-2-fluoro-phenylcarbamoyl)-2-(4-fluoro-phenyl)-ethyl]-carbamic acid tert-butyl ester as a colorless solid (2.0 g, 53%).

LC-MS: Obs. Mass, 417. Calcd. Mass, 417 for $C_{23}H_{27}F_2N_2O_3^+$.

Preparation of (R)-tert-butoxycarbonylamino-[4-(2-hydroxy-1-hydroxymethyl-ethoxy)-phenyl]-acetic acid (1) 2,5-Dichloro-benzenesulfonic acid 2-benzyloxy-1-benzyloxymethyl-ethyl ester was obtained from 1,3-bis-benzyloxy-propan-2-ol according to the procedure of Shimizu, M. et al. (*J. Chem. Soc. Chem. Commun.* 1986, 867).

(2) To a solution of (R)-tert-butoxycarbonylamino-(4-hydroxy-phenyl)-acetic (1.0 g, 3.74 mmol) in dry N,N-dimethylformamide (50 mL) was added sodium hydride (60% suspension in mineral oil) (328 mg, 8.2 mmol) and the mixture was stirred at ambient temperature under an atmosphere of dry argon for 15 minutes. 2,5-Dichloro-benzenesulfonic acid 2-benzyloxy-1-benzyloxymethyl-ethyl ester (2.2 g, 4.57 mmol) dissolved in dry N,N-dimethylformamide (25 mL) was added and the stirred mixture placed in a 110° C. oil bath for 10 minutes. The reaction mixture was cooled to ambient temperature and 0.5 M aqueous hydrochloric acid (16.5 mL, 8.3 mmol) added. The reaction mixture was extracted with ethyl acetate (2×250 mL), the combined organic layers washed with water (2×250 mL), brine (250 mL), dried over sodium sulfate, filtered and concentrated in vacuo. The residue was purified by chromatography over silica gel eluted with 49:1 v/v dichloromethane/methanol containing 0.2% v/v acetic acid to afford (R)-[4-(2-benzyloxy-1-benzyloxymethyl-ethoxy)-phenyl]-tert-butoxycarbonylamino-acetic acid as a colorless solid (1.2 g, 80%).

HRMS: Obs. Mass, 544.2307. Calcd. Mass, 544.2306 for $C_{30}H_{35}NNaO_7^+$.

(3) A hydrogenation vessel containing a solution of (R)-[4-(2-benzyloxy-1-benzyloxymethyl-ethoxy)-phenyl]-tert-butoxycarbonylamino-acetic acid (1.86 g, 3.57 mmol) in methanol (50 mL) was purged with nitrogen and 10% palladium on carbon (100 mg) added. The atmosphere above the methanol solution was exchanged for hydrogen and the reaction mixture stirred vigorously for 30 minutes at ambient temperature. The reaction mixture was filtered through a pad of Celite and concentrated in vacuo to give (R)-tert-butoxycarbonylamino-[4-(2-hydroxy-1-hydroxymethyl-ethoxy)-phenyl]-acetic acid which was of sufficient purity for subsequent use without additional purification (0.88 g, 73%).

HRMS: Obs. Mass, 364.1368. Calcd. Mass, 364.1367 for $C_{16}H_{23}NNaO_7^+$.

HRMS: Obs. Mass, 566.2100. Calcd. Mass, 566.2097 for $C_{30}H_{30}F_2N_3O_6^+$.

EXAMPLE 161

(S)—N-(4-Cyclopropyl-2-fluoro-phenyl)-2-{(R)-4-[4-(2-hydroxy-ethoxy)-phenyl]-2,5-dioxo-imidazolidin-1-yl}-3-(4-methoxy-phenyl)-propionamide

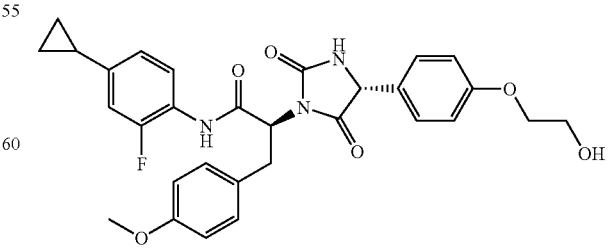

Prepared by the same method as described in example 160 except that (i) (S)-2-tert-butoxycarbonylamino-3-(4-methoxy-phenyl)-propionic acid was used in place of (S)-2-tert-butoxycarbonylamino-3-(4-fluoro-phenyl)-propionic acid, and (ii) (R)-tert-butoxycarbonylamino-{4-[2-(tetrahydro-pyran-2-yloxy)-ethoxy]-phenyl}-acetic was used in place of (R)-tert-butoxycarbonylamino-[4-(2-hydroxy-1-hydroxymethyl-ethoxy)-phenyl]-acetic acid. (R)-tert-Butoxycarbonylamino-{4-[2-(tetrahydro-pyran-2-yloxy)-ethoxy]-phenyl}-acetic acid was prepared as described in example 48.

HRMS: Obs Mass (M+H$^+$), 548.2180. Calcd. Mass, 548.2192 for $C_{30}H_{31}FN_3O_6^+$.

EXAMPLE 162

(S)—N-(4-Cyclopropyl-2-fluoro-phenyl)-2-{(R)-4-[4-((S)-2,3-dihydroxy-propoxy)-phenyl]-2,5-dioxo-imidazolidin-1-yl}-3-(4-methoxy-phenyl)-propionamide

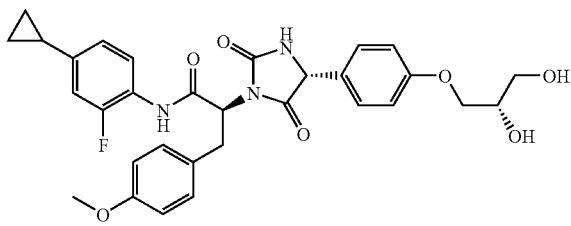

Prepared by the same method as described in example 160 except that (i) (S)-2-tert-butoxycarbonylamino-3-(4-methoxy-phenyl)-propionic acid was used in place of (S)-2-tert-butoxycarbonylamino-3-(4-fluoro-phenyl)-propionic acid, and (ii) (R)-tert-butoxycarbonylamino-[4-((S)-2,2-dimethyl-[1,3]dioxolan-4-ylmethoxy)-phenyl]-acetic acid (prepared as described in example 116) was used in place of (R)-tert-butoxycarbonylamino-[4-(2-hydroxy-1-hydroxymethyl-ethoxy)-phenyl]-acetic acid.

HRMS: Obs Mass (M+Na$^+$), 600.2112. Calcd. Mass, 600.2116 for $C_{31}H_{32}FN_3NaO_7^+$.

EXAMPLE 163

(2S,3S)—N-(4-Cyclopropyl-2-fluoro-phenyl)-2-{(R)-4-[4-(2-hydroxy-ethoxy)-phenyl]-2,5-dioxo-imidazolidin-1-yl}-3-phenyl-butyramide

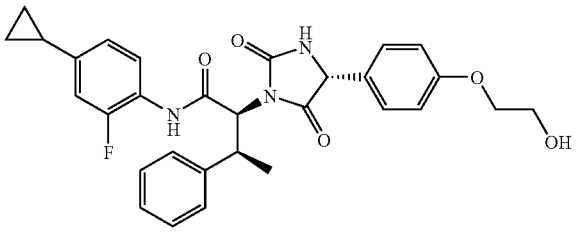

Prepared by the same method as described in example 48 except that (i) 4-cyclopropyl-2-fluoroaniline (prepared as described below) was used in place of 2-fluoro-4-iodoaniline, and (ii) the modified procedure shown below was used to perform step 6.

Preparation of 4-cyclopropyl-2-fluoroaniline:

(According to the procedure of D. Wallace and C. Chen, Tetrahedron Lett., 43, 6987 (2002)) 4-Bromo-2-fluoroaniline (19.0 g, 100 mmol) was reacted with cyclopropyl boronic acid (11.3 g, 131 mmol), palladium(II) acetate (1.12 g, 4.79 mmol), tricyclohexyl phosphine (2.80 g, 13.2 mmol), and potassium phosphate (74.2 g, 265 mmol) in toluene (400 mL) and water (30 mL). The mixture was heated in an oil bath at 100° C. for 2 days, cooled, and the liquid was filtered through a pad of celite. The residual solid in the reaction vessel was triturated with water (200 mL), and the suspension was filtered through celite. The aqueous filtrate was extracted once with hexanes (100 mL), the combined organic layers were dried over anhydrous magnesium sulfate. The dried organic layers were filtered through a silica gel pad, and the pad was washed with 80% v/v dichloromethane in hexanes (250 mL). The filtrates were concentrated in vacuo to give a red oil that was fractionally distilled (Vigreux column, 6 plates). The fraction distilling between 65-73° C. at 6-7 mbar was collected to give 6.8 g (45 mmol, 45%) of 4-cyclopropyl-2-fluoroaniline as a pale yellow liquid.

$^1$H-NMR (300 MHz, CDCl$_3$) δ: 6.69 (m, 3H), 3.57 (br.s., 2H), 1.79 (m, 1H), 0.87 (m, 2H), 0.57 (m, 2H).

Step 6: 2-{2-Amino-2-[4-(2-trimethylsilanyloxy-ethoxy)-phenyl]-acetylamino}-N-(4-cyclopropyl-2-fluorophenyl)-3-phenyl-butyramide (680 mg, 1.2 mmol) and pyridine (3 mL) were dissolved in dichloromethane (60 mL) at −78° C. To this mixture was added a solution of triphosgene (296 mg, 1 mmol) in dichloromethane (15 mL) dropwise. The mixture was allowed to slowly warm to room temperature and stirred overnight at room temperature. The mixture was cooled in an ice bath and 3 M HCl (60 mL) was added slowly and stirring was continued at 0° C. for 30 minutes. The organic layer was separated and dried over anhydrous sodium sulfate. Concentration gave 150 mg of a oily solid that was chromatographed over silica gel (65% v/v ethyl acetate in hexanes) to give N-(4-cyclopropyl-2-fluoro-phenyl)-2-{4-[4-(2-hydroxy-ethoxy)-phenyl]-2,5-dioxo-imidazolidin-1yl}-3-phenyl-butyramide as a yellow solid (70 mg, 0.13 mmol, 13%).

HRMS: Obs Mass (M+H$^+$), 532.2244. Calcd. Mass, 532.2242 for $C_{30}H_{31}FN_3O_5^+$.

EXAMPLE 164

(S)—N-(4-Cyclopropyl-2-fluoro-phenyl)-2-{(R)-4-[4-(2-hydroxy-1-hydroxymethyl-ethoxy)-phenyl]-2,5-dioxo-imidazolidin-1-yl}-3-(4-methoxy-phenyl)-propionamide

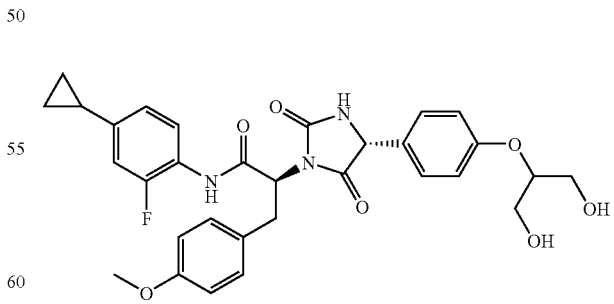

Prepared by the same method as described in example 160 except that (i) (S)-2-tert-butoxycarbonylamino-3-(4-methoxy-phenyl)-propionic acid was used in place of (S)-2-tert-butoxycarbonylamino-3-(4-fluoro-phenyl)-propionic acid in step 1, and (ii) (3-dimethylamino-propyl)-ethyl-carbodiimide hydrochloride was used as the coupling reagent in place of O-benzotriazol-1-yl-N,N,N',N'-tetramethyluronium hexaflurorophosphate in step 4.

HRMS: Obs Mass (M+H$^+$), 578.2295 Calcd. Mass, 578.2297 for $C_{31}H_{33}FN_3O_7^+$.

EXAMPLE 165

(2S,3S)—N-(4-Cyclopropyl-2-fluoro-phenyl)-2-{(R)-4-[4-((R)-2,3-dihydroxy-propoxy)-phenyl]-2,5-dioxo-imidazolidin-1-yl}-3-phenyl-butyramide

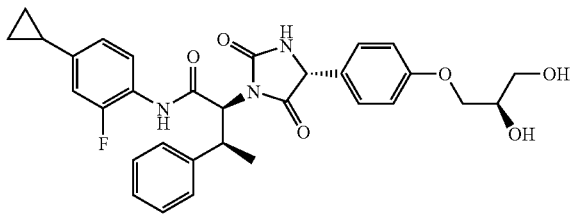

Prepared by the same method as described in example 160 except that (i) (2S,3S)-2-tert-butoxycarbonylamino-3-phenyl-butyric acid was used in place of (S)-2-tert-butoxycarbonylamino-3-(4-fluoro-phenyl)-propionic acid in step 1, and (ii) (R)-tert-butoxycarbonylamino-[4-((R)-2,2-dimethyl-[1,3]dioxolan-4-ylmethoxy)-phenyl]-acetic acid was used in place of (R)-tert-butoxycarbonylamino-{4-[2-(tetrahydro-pyran-2-yloxy)-ethoxy]-phenyl}-acetic acid in step 4. (R)-tert-Butoxycarbonylamino-[4-((R)-2,2-dimethyl-[1,3]dioxolan-4-ylmethoxy)-phenyl]-acetic acid was prepared and used as described in example 114.

HRMS: Obs Mass (M+H$^+$), 562.2349. Calcd. Mass, 562.2348 for $C_{31}H_{33}FN_3O_6^+$.

EXAMPLE 166

(2S,3S)—N-(4-Cyclopropyl-2-fluoro-phenyl)-2-((R)-4-{4-[2-(2-hydroxy-ethoxy)-ethoxy]-phenyl}-2,5-dioxo-imidazolidin-1-yl)-3-phenyl-butyramide

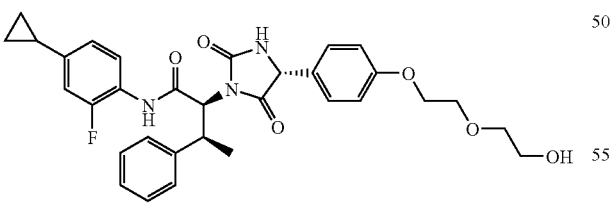

Prepared by the same method as described in example 165 except that (R)-tert-butoxycarbonylamino-(4-{2-[2-(tetrahydro-pyran-2-yloxy)-ethoxy]-ethoxy}-phenyl)-acetic acid was used in place of (R)-tert-butoxycarbonylamino-[4-((S)-2,2-dimethyl-[1,3]dioxolan-4-ylmethoxy)-phenyl]-acetic acid.

HRMS: Obs Mass (M+H$^+$), 576.2504. Calcd. Mass, 576.2505 for $C_{32}H_{35}FN_3O_6^+$.

EXAMPLE 167

(2S,3S)—N-(4-Cyclopropyl-2-fluoro-phenyl)-2-((R)-4-{4-[2-(2-methoxy-ethoxy)-ethoxy]-phenyl}-2,5-dioxo-imidazolidin-1-yl)-3-phenyl-butyramide

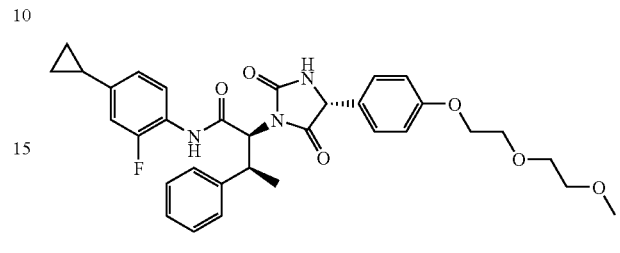

Prepared by the same method as described in example 165 except that (R)-tert-butoxycarbonylamino-{4-[2-(2-methoxy-ethoxy)-ethoxy]-phenyl}-acetic acid was used in place of (R)-tert-butoxycarbonylamino-[4-((S)-2,2-dimethyl-[1,3]dioxolan-4-ylmethoxy)-phenyl]-acetic acid.

HRMS: Obs Mass (M+H$^+$), 590.2656. Calcd. Mass, 590.2661 for $C_{33}H_{37}FN_3O_6^+$. HRMS: Obs Mass (M+Na$^+$), 612.2475. Calcd. Mass, 612.2480 for $C_{33}H_{36}FN_3NaO_6^+$.

EXAMPLE 168

(2S,3S)—N-(4-Cyclopropyl-2-fluoro-phenyl)-2-[(R)-4-(4-methylcarbamoylmethoxy-phenyl)-2,5-dioxo-imidazolidin-1-yl]-3-phenyl-butyramide

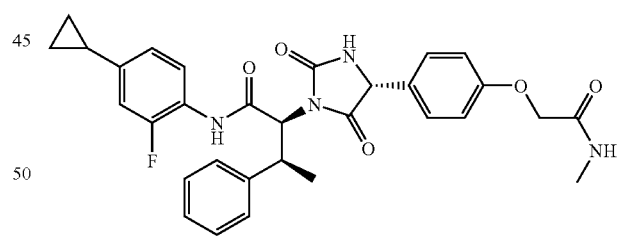

Prepared by the same method as described in example 165 except that (R)-tert-butoxycarbonylamino-(4-methylcarbamoylmethoxy-phenyl)-acetic acid was used in place of (R)-tert-butoxycarbonylamino-[4-((S)-2,2-dimethyl-[1,3]dioxolan-4-ylmethoxy)-phenyl]-acetic acid. (R)-tert-Butoxycarbonylamino-(4-methylcarbamoylmethoxy-phenyl)-acetic acid was prepared as described in example 9.

HRMS: Obs Mass (M+H$^+$), 559.2354. Calcd. Mass, 559.2351 for $C_{31}H_{32}FN_4O_5^+$.

EXAMPLE 169

(S)-2-{(R)-4-[4-((R)-2,3-Dihydroxy-propoxy)-phenyl]-2,5-dioxo-imidazolidin-1-yl}-4-methyl-pentanoic acid (4-cyclopropyl-2-fluoro-phenyl)-amide

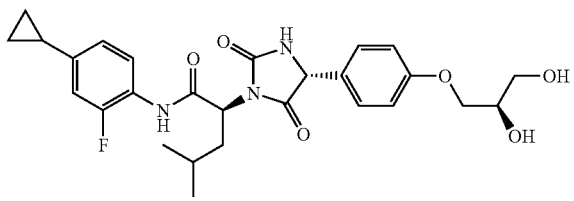

Prepared by the same method as described in example 165 except that (S)-2-tert-butoxycarbonylamino-4-methyl-pentanoic acid was used in place of (2S,3S)-2-tert-butoxycarbonylamino-3-phenyl-butyric acid.

HRMS: Obs Mass (M+H$^+$), 514.2349. Calcd. Mass, 514.2348 for $C_{27}H_{33}FN_3O_6^+$.

EXAMPLE 170

(S)-2-{(R)-4-[4-((S)-2,3-Dihydroxy-propoxy)-phenyl]-2,5-dioxo-imidazolidin-1-yl}-4-methyl-pentanoic acid (4-cyclopropyl-2-fluoro-phenyl)-amide

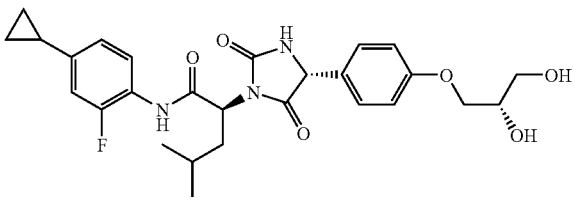

Prepared using the same method as described in example 169 except that (R)-tert-butoxycarbonylamino-[4-((R)-2,2-dimethyl-[1,3]dioxolan-4-ylmethoxy)-phenyl]-acetic acid was used in place of (R)-tert-butoxycarbonylamino-[4-((S)-2,2-dimethyl-[1,3]dioxolan-4-ylmethoxy)-phenyl]-acetic acid in step 4. (R)-tert-butoxycarbonylamino-[4-((R)-2,2-dimethyl-[1,3]dioxolan-4-ylmethoxy)-phenyl]-acetic acid was prepared by the same method as described for the preparation of (R)-tert-butoxycarbonylamino-[4-((S)-2,2-dimethyl-[1,3]dioxolan-4-ylmethoxy)-phenyl]-acetic acid in example 114 except that (R)-2,2-dimethyl-1,3-dioxolane-4-methanol was used in place of (S)-2,2-dimethyl-1,3-dioxolane-4-methanol.

HRMS: Obs Mass (M+Na$^+$), 536.2164. Calcd. Mass, 536.2167 for $C_{27}H_{32}FN_3NaO_6^+$.

EXAMPLE 171

(S)-2-{(R)-4-[4-(2-Hydroxy-1-hydroxymethyl-ethoxy)-phenyl]-2,5-dioxo-imidazolidin-1-yl}-4-methyl-pentanoic acid (4-cyclopropyl-2-fluoro-phenyl)-amide

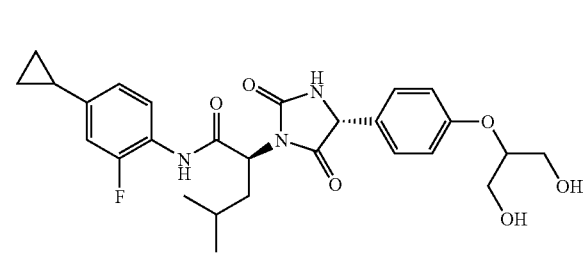

Prepared by the same method as described in example 160 except that (i) (S)-2-tert-butoxycarbonylamino-4-methyl-pentanoic acid was used in place of (S)-2-tert-butoxycarbonylamino-3-(4-fluoro-phenyl)-propionic acid in step 1, and (ii) (3-dimethylamino-propyl)-ethyl-carbodiimide hydrochloride was used as the coupling reagent in place of O-benzotriazol-1-yl-N,N,N',N'-tetramethyluronium hexafluorophosphate in step 4.

HRMS: Obs Mass (M+H$^+$), 514.2347 Calcd. Mass, 514.2348 for $C_{27}H_{33}FN_3O_6^+$.

EXAMPLE 172

(2S,3S)-2-{(R)-4-[4-(2-Methoxy-ethoxy)-phenyl]-2,5-dioxo-imidazolidin-1-yl}-3-phenyl-N-p-tolyl-butyramide

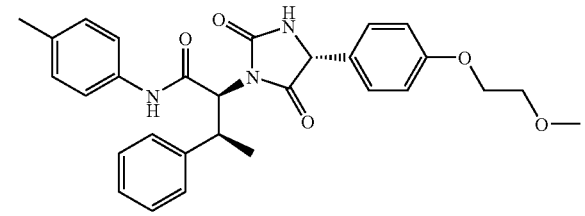

Prepared by the same method as described in example 1 except that (i) 4-methyl-aniline was used in place of 4-bromoaniline in step 2, and (ii) (R)-tert-butoxycarbonylamino-[4-(2-methoxy-ethoxy)-phenyl]-acetic acid was used in place of (R)-tert-butoxycarbonylamino-(4-methoxy-phenyl)-acetic acid in step 4. (R)-tert-Butoxycarbonylamino-[4-(2-methoxy-ethoxy)-phenyl]-acetic acid was prepared as described in example 80.

HRMS: Obs Mass (M+H$^+$), 502.2332. Calcd. Mass, 502.2337 for $C_{29}H_{32}N_3O_5^+$.

EXAMPLE 173

(2S,3S)—N-(4-Ethyl-phenyl)-2-{(R)-4-[4-(2-methoxy-ethoxy)-phenyl]-2,5-dioxo-imidazolidin-1-yl}-3-phenyl-butyramide

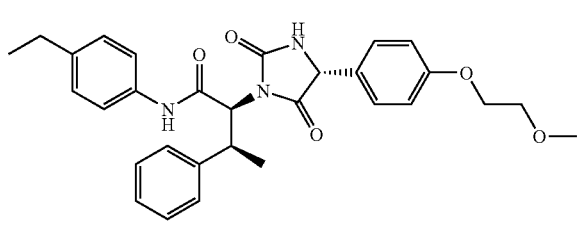

Prepared using the same method as described in example 1 except that (i) 4-ethyl-aniline was used in place of 4-bromoaniline in step 2, and (ii) (R)-tert-butoxycarbonylamino-[4-(2-methoxy-ethoxy)-phenyl]-acetic acid was used in place of (R)-tert-butoxycarbonylamino-(4-methoxy-phenyl)-acetic acid in step 4. (R)-tert-Butoxycarbonylamino-[4-(2-methoxy-ethoxy)-phenyl]-acetic acid was prepared as described in example 80.

HRMS: Obs Mass (M+H$^+$), 516.2489. Calcd. Mass, 516.2493 for $C_{30}H_{34}N_3O_5^+$.

EXAMPLE 174

(2S,3S)—N-(4-Isopropyl-phenyl)-2-{(R)-4-[4-(2-methoxy-ethoxy)-phenyl]-2,5-dioxo-imidazolidin-1-yl}-3-phenyl-butyramide

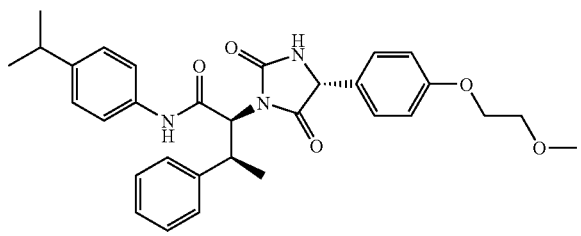

Prepared using the same method as described in example 1 except that (i) 4-isopropyl-aniline was used in place of 4-bromoaniline in step 2, and (ii) (R)-tert-butoxycarbonylamino-[4-(2-methoxy-ethoxy)-phenyl]-acetic acid was used in place of (R)-tert-butoxycarbonylamino-(4-methoxy-phenyl)-acetic acid in step 4. (R)-tert-Butoxycarbonylamino-[4-(2-methoxy-ethoxy)-phenyl]-acetic acid was prepared as described in example 80.

HRMS: Obs Mass (M+H$^+$), 530.2646. Calcd. Mass, 530.2650 for $C_{31}H_{36}N_3O_5^+$.

EXAMPLE 175

(2S,3S)—N-(2-Fluoro-4-methyl-phenyl)-2-{(R)-4-[4-(2-methoxy-ethoxy)-phenyl]-2,5-dioxo-imidazolidin-1-yl}-3-phenyl-butyramide

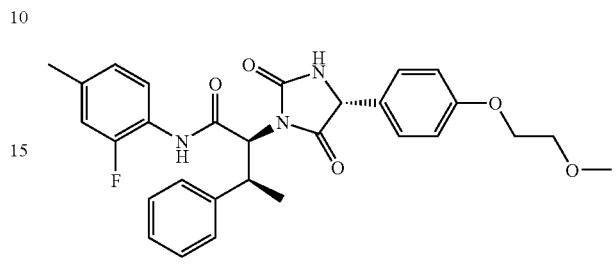

Prepared using the same method as described in example 1 except that (i) 2-fluoro-4-methyl-aniline was used in place of 4-bromoaniline in step 2, and (ii) (R)-tert-butoxycarbonylamino-[4-(2-methoxy-ethoxy)-phenyl]-acetic acid was used in place of (R)-tert-butoxycarbonylamino-(4-methoxy-phenyl)-acetic acid in step 4. (R)-tert-Butoxycarbonylamino-[4-(2-methoxy-ethoxy)-phenyl]-acetic acid was prepared as described in example 80.

HRMS: Obs Mass (M+Na$^+$), 542.2056. Calcd. Mass, 542.2061 for $C_{29}H_{30}FN_3NaO_5^+$.

EXAMPLE 176

(S)—N-(4-tert-Butyl-2-chloro-phenyl)-2-{(R)-4-[4-((R)-2,3-dihydroxy-propoxy)-phenyl]-2,5-dioxo-imidazolidin-1-yl}-3-methyl-butyramide

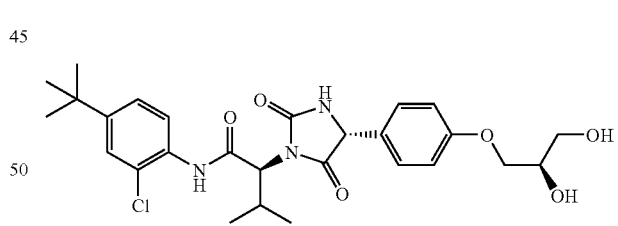

Prepared by the same method as described in example 43 except that (i) (S)-2-(9H-fluoren-9-ylmethoxycarbonylamino)-3-methyl-butyric acid was used in place of (S)-2-(9H-fluoren-9-ylmethoxycarbonylamino)-3-naphthalen-2-yl-propionic acid in step 1, (ii) 4-tert-butyl-2-chlorophenylamine was used in place of 2-fluoro-4-iodoaniline in step 1, and (iii) the steps following step 3 were performed as described in example 114.

LC-MS: Obs Mass (M+H$^+$), 532; Calcd. Mass, 532 for $C_{27}H_{35}ClN_3O_6^+$.

EXAMPLE 177

(2S,3S)—N-(4-Ethoxy-2-fluoro-phenyl)-2-{(R)-4-[4-(2-methoxy-ethoxy)-phenyl]-2,5-dioxo-imidazolidin-1-yl}-3-phenyl-butyramide

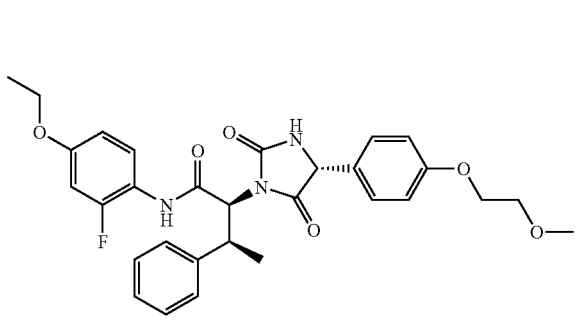

Prepared using the same method as described in example 1 except that (i) 4-ethoxy-2-fluoro-aniline was used in place of 4-bromoaniline in step 2, and (ii) (R)-tert-butoxycarbonylamino-[4-(2-methoxy-ethoxy)-phenyl]-acetic acid was used in place of (R)-tert-butoxycarbonylamino-(4-methoxy-phenyl)-acetic acid in step 4. (R)-tert-Butoxycarbonylamino-[4-(2-methoxy-ethoxy)-phenyl]-acetic acid was prepared as described in example 80.

HRMS: Obs Mass (M+H$^+$), 550.2352. Calcd. Mass, 550.2348 for $C_{30}H_{33}FN_3O_6^+$.

EXAMPLE 178

(2S,3S)—N-(2-Fluoro-4-isopropoxy-phenyl)-2-{(R)-4-[4-(2-methoxy-ethoxy)-phenyl]-2,5-dioxo-imidazolidin-1-yl}-3-phenyl-butyramide

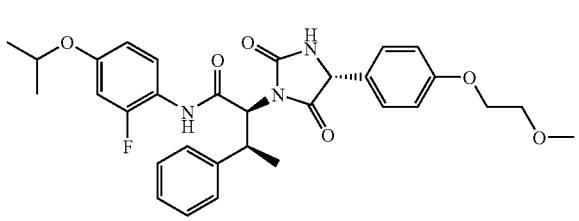

Prepared by the same method as described in example 50 except that 2-fluoro-4-isopropyloxyaniline hydrochloride was used in place of 2-fluoro-4-iodoaniline.

HRMS: Obs Mass (M+H$^+$), 564.2498. Calcd. Mass, 564.2505 for $C_{31}H_{35}FN_3O_6^+$.

EXAMPLE 179

(2S,3S)—N-(4-Azetidin-1-yl-2-fluoro-phenyl)-2-{(R)-4-[4-(2-methoxy-ethoxy)-phenyl]-2,5-dioxo-imidazolidin-1-yl}-3-phenyl-butyramide

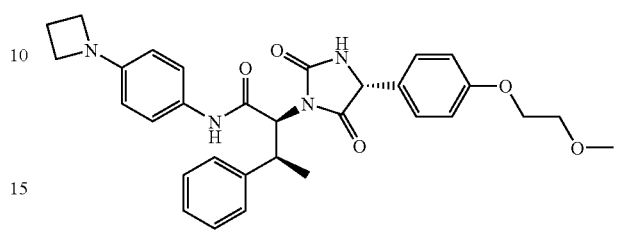

Prepared by the same method as described in example 50 except that 4-azetidin-1-yl-2-fluoro-phenylamine was used in place of 2-fluoro-4-iodoaniline. 4-Azetidin-1-yl-2-fluoro-phenylamine was prepared in the following way:

To a mixture of 2-fluoro-4-iodoaniline (1 g, 4.14 mmol), copper iodide (304 mg, 0.21 mmol) and potassium phosphate (1.75 g, 8.27 mmol) in ethylene glycol (465 µl, 8.27 mmol) and isopropanol (4 mL) in a bomb flask was added azetidine (304 mg, 5.17 mmol). The flask was sealed and heated to 80° C. for 24 hours. The reaction mixture was dissolved in ethyl acetate (50 mL), washed with water (3×50 mL), brine (50 mL), and the brine layer back extracted with ethyl acetate (2×50 mL). The combined organic extracts were dried over sodium sulfate, filtered and concentrated in vacuo to a brown oil. The oil was purified by chromatography over silica gel eluted with 40% v/v ethyl acetate in hexanes. The product containing fractions were combined and concentrated to give 4-azetidin-1-yl-2-fluoro-phenylamine as an orange oil (555 mg, 81% yield).

HRMS: Obs Mass (M+H$^+$), 561.2501. Calcd. Mass, 561.2508 for $C_{31}H_{34}FN_4O_5^+$.

EXAMPLE 180

(2S,3S)—N-(4-Cyano-2-fluoro-phenyl)-2-{(R)-4-[4-(2-methoxy-ethoxy)-phenyl]-2,5-dioxo-imidazolidin-1-yl}-3-phenyl-butyramide

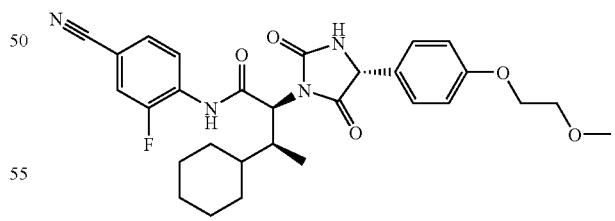

Prepared by the same method as that described in example 50 except that prior to performing step 4 in the reaction sequence the transformation detailed below (step 3a) was performed.

Step 3a: To an argon degassed and dried flask was added (2S,3S)-2-amino-N-(2-fluoro-4-iodo-phenyl)-3-phenyl-butyramide (796 mg, 1.99 mmol), zinc cyanide (352 mg, 2.99 mmol), tetrakis-triphenylphosphine palladium (0) (116 mg, 0.1 mmol) and dry tetrahydrofuran (4 mL). After heating at 80° C. for 8 hours there was no reaction. To the cooled mixture was added 2-dicylohexylphosphino-2'-6'-dimethoxybiphenyl (42 mg, 0.1 mmol) and the reaction mixture heated again to 80° C. for 90 minutes, again no reaction occurred. To the cooled mix was added triethylamine (840 μl, 5.99 mmol) and the reaction mixture heated at 80° C. for 2 hours, again no reaction occurred. To the cooled mix was added 2-dicylohexylphosphino-2'-6'-dimethoxybiphenyl (84 mg, 0.2 mmol) and still no reaction occurred after 2 hours at 85° C. To the cooled mix was added rac-2-2'-bis(diphenylphosphino)-1-1'binaphthyl (125.6 mg, 0.2 mmol) and dry toluene (2 mL). After heating at 85° C. for 40 hours the reaction mix was dissolved in ethyl acetate (50 mL) and washed with 1.5 N aqueous potassium hydrogen sulfate solution, saturated aqueous sodium bicarbonate solution and the aqueous layers were back extracted with ethyl acetate (2×50 mL). The combined organic layers were dried over sodium sulfate and concentrated. The crude residue was purified by chromatography over silica gel gradient eluted from 5 to 15% v/v ethyl acetate in hexanes to give (2S,3S)-2-amino-N-(4-cyano-2-fluoro-phenyl)-3-phenyl-butyramide as a yellow residue after concentration of the product containing fractions (120 mg, 20.2% yield).

HRMS: Obs Mass (M+H$^+$), 531.2035. Calcd. Mass, 531.2038 for $C_{29}H_{28}FN_4O_5^+$.

EXAMPLE 181

(S)—N-(4-Cyano-2-fluoro-phenyl)-2-{(R)-4-[4-(2-hydroxy-ethoxy)-phenyl]-2,5-dioxo-imidazolidin-1-yl}-3-methyl-butyramide

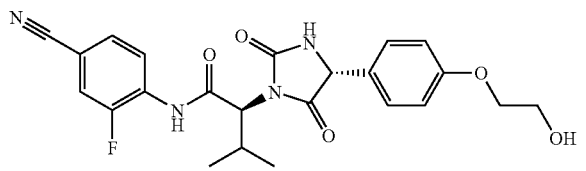

Prepared by the same method as described in example 43 except that step 1 was performed as described below.

Step 1: To a solution of (S)-2-(9H-fluoren-9-ylmethoxycarbonylamino)-3-methyl-butyric acid (2.5 g, 7.37 mmol) and a few drops of N,N-dimethylformamide in dichloromethane (20 mL) was slowly added oxalyl chloride (1.3 mL, 14.74 mmol) at 0° C. under an atmosphere of dry nitrogen. The mixture was stirred for 15 minutes at 0° C. and 2 hours at room temperature. After removal of the solvent, the residue was dissolved in dichloromethane (20 mL) and to the resulting solution was added 4-amino-3-fluoro-benzonitrile (840 mg, 6.14 mmol), 4-dimethylaminopyridine (150 mg, 1.2 mmol) and pyridine (0.78 mL, 9.21 mmol) at 0° C. The mixture was stirred for 2 hrs at 0° C. and overnight at room temperature. The reaction was quenched with 1 M aqueous citric acid solution and then extracted with dichloromethane (three times). The combined organic extracts were washed with 1 M aqueous citric acid solution, brine, saturated aqueous sodium carbonate, brine, dried over sodium sulfate, filtered and concentrated in vacuo. The residue was purified by chromatography over silica gel gradient eluted from 100% dichloromethane up to 10% methanol/90% dichloromethane over 30 minutes. Concentration of the product containing fractions gave [(S)-1-(4-cyano-2-fluoro-phenylcarbamoyl)-2-methyl-propyl]-carbamic acid 9H-fluoren-9-ylmethyl ester as a white solid (2.15 mg, 77%).

LC-MS: Obs Mass (M+H$^+$), 458; Calcd. Mass, 548 for $C_{27}H_{25}FN_3O_3^+$. LC-MS: Obs Mass (M+H$^+$), 455; Calcd. Mass, 455 for $C_{23}H_{24}FN_4O_5^+$.

EXAMPLE 182

(2S,3S)—N-(4-Acetyl-2-fluoro-phenyl)-2-{(R)-2,5-dioxo-4-[4-(2-oxo-2-pyrrolidin-1-yl-ethoxy)-phenyl]-imidazolidin-1-yl}-3-phenyl-butyramide

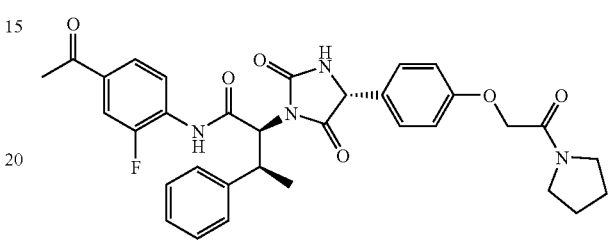

Prepared by the same method as described in example 145 with this compound being obtained as a by-product during the purification in step 6.

HRMS: Obs Mass (M+H$^+$), 601.2454. Calcd. Mass, 601.2457 for $C_{33}H_{34}FN_4O_6^+$.

Compound IC$_{50}$ Determination in MEK Cascade Assay

The evaluation of the compounds as MEK inhibitor was performed in a bead-based FP assay termed IMAP assay with MEK cascade components. In brief, the assay was performed in a reaction solution containing 10 mM HEPES, pH 7.0, 10 mM MgCl$_2$, 50 mM NaCl, 0.1 mM NaVO$_4$, and 1 mM DTT in the presence of 50 uM ATP, 0.45 nM c-RAF, 11.25 nM MEK, 90.5 nM ERK, and 0.5 μM FITC-labeled ERK (FITC-Aca-Ala-Ala-Ala-Thr-Gly-Pro-Leu-Ser-Pro-Gly-Pro-Phe-Ala-NH2). C-RAF, MEK, ERK and the ERK peptide substrates were added sequentially into the reaction buffer. Activated c-Raf phosphorylates MEK, activated MEK phosphorylates ERK, and subsequently activated ERK phosphrylates its peptide substrate. The FITC-labeled peptide substrates, when phosphorylated by the kinase, bind to nanoparticles derivatized with trivalent metal cations through a metal-phospholigand interaction. The result of this bound fluoresceinated phosphorylated product is an increase in polarization signal caused by a decrease in the molecular mobility of the bound product. Ten-point serial dilutions of the compounds were added into the MEK cascade assays before mixing with ERK and ERK peptide substrates. The reaction was incubated at 37° C. for 20 minutes for MEK activation, 20 minutes for ERK activation, 30 minutes for ERK peptide substrate phosphorylation, then was incubated overnight at room temperature for binding of IMAP beads. The IMAP assay was performed in a 384-well plate format. The changes in fluorescence polarization were measured by LJL instrument at 485 nm for excitation and 530 for emission. Polarization value (MP) was calculated as the following:

(MP)=1000×(intensity$_{vertical}$−intensity$_{horizontal}$)/(intensity$_{vertical}$+intensity$_{horizontal}$).

The IC$_{50}$ values were generated using Excel XLfit3 wizard. Percent activity and percent inhibition of reactions in the presence of a compound were calculated by comparing their MP values to those without a compound (as 100% activity).

The compounds of formula I in the above assay exhibit IC$_{50}$ values of less than 10 micromolar.

What is claimed is:

1. A compound of formula I:

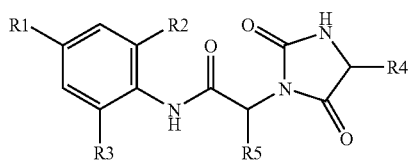

wherein:
R1 is selected from the group consisting of bromo, iodo, ethynyl, cycloalkyl, alkoxy, azetidinyl, acetyl, heterocycyl, cyano, straight-chained alkyl and branched-chain alkyl;
R2 is selected from the group consisting of hydrogen, chloro, fluoro, and alkyl;
R3 is selected from the group consisting of hydrogen and fluoro;
R4 is selected from the group consisting of optionally substituted aryl, alkyl, and cycloalkyl;
R5 is selected from the group consisting of hydrogen and

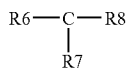

wherein R6 is selected from the group consisting of hydroxyl, alkoxy, cycloalkyl, trihaloalkyl, alkyl, optionally substituted aryl, and optionally substituted heteroaryl;
R7 and R8 are independently selected from the group consisting of hydrogen, alkyl, and trihaloalkyl; or
R6 and R7 can together form a cycloalkyl group and R8 is hydrogen;
and pharmaceutically acceptable salts or esters thereof.

2. The compound of claim 1 with the formula:

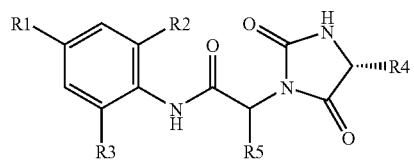

wherein:
R1 is selected from the group consisting of bromo, iodo, ethynyl, cycloalkyl, alkoxy, acetyl, alkylthio, heterocycyl, cyano, straight-chained lower alkyl and branched-chain lower alkyl;
R2 is selected from the group consisting of hydrogen, chloro, fluoro, and lower alkyl;
R3 is selected from the group consisting of hydrogen and fluoro;
R4 is selected from the group consisting of optionally substituted aryl, lower alkyl, and cycloalkyl;
R5 is selected from the group consisting of hydrogen and

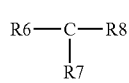

wherein R6 is selected from the group consisting of hydroxyl, alkoxy, cycloalkyl, trihalo lower alkyl, lower alkyl, optionally substituted aryl, and optionally substituted heteroaryl;
R7 and R8 are independently selected from the group consisting of hydrogen, lower alkyl, and trihalo lower alkyl; or
R6 and R7 can together form a cycloalkyl group and R8 is hydrogen;
and pharmaceutically acceptable salts or esters thereof.

3. The compound of claim 2 wherein R1 is selected from the group consisting of iodo, ethynyl, and cyclopropyl.

4. The compound of claim 3 wherein R2 is selected from the group consisting of hydrogen, chloro, and fluoro.

5. The compound of claim 4 wherein R3 is hydrogen.

6. The compound of claim 5 wherein R5 is

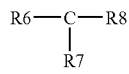

and R7 and R8 are independently selected from the group consisting of hydrogen and methyl.

7. The compound of claim 6 wherein R4 is optionally substituted aryl.

8. The compound of claim 7 wherein R1 is selected from the group consisting of iodo, ethynyl, and cyclopropyl, R2 is selected from the group consisting of hydrogen, fluoro, and chloro, R3 is hydrogen, R4 is optionally substituted phenyl, R5 is

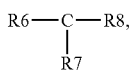

R6 is optionally substituted phenyl, R7 is methyl, and R8 is hydrogen.

9. The compound of claim 8 wherein R4 is phenyl substituted with alkoxy.

10. The compound of claim 9 wherein R1 is iodo and R2 is selected from the group consisting of chloro and fluoro.

11. The compound of claim 10, wherein R6 is phenyl and R4 is phenyl substituted with a member selected from a 2,3-dihydroxy-propoxy group and a 2-hydroxy-ethoxy group.

12. A compound selected from the group consisting of:
(2S,3S)—N-(4-Bromo-phenyl)-2-[(R)-4-(4-methoxy-phenyl)-2,5-dioxo-imidazolidin-1-yl]-3-phenyl-butyramide;
(2S,3S)—N-(4-Iodo-phenyl)-2-[(R)-4-(4-methoxy-phenyl)-2,5-dioxo-imidazolidin-1-yl]-3-phenyl-butyramide;
(2S,3S)—N-(4-Ethynyl-2-fluoro-phenyl)-2-{(R)-4-[4-(2-hydroxy-ethoxy)-phenyl]-2,5-dioxo-imidazolidin-1-yl}-3-phenyl-butyramide;
(2R,3S)—N-(4-Ethynyl-2-fluoro-phenyl)-2-{(R)-4-[4-(2-hydroxy-ethoxy)-phenyl]-2,5-dioxo-imidazolidin-1-yl}-3-phenyl-butyramide;

(2S,3S)—N-(2-Chloro-4-iodo-phenyl)-2-{(R)-4-[4-(2-hydroxy-ethoxy)-phenyl]-2,5-dioxo-imidazolidin-1-yl}-3-phenyl-butyramide;

(2S,3S)-2-{(R)-4-[4-(2-Hydroxy-ethoxy)-phenyl]-2,5-dioxo-imidazolidin-1-yl}-N-(4-iodo-2-methyl-phenyl)-3-phenyl-butyramide;

(2S,3S)—N-(2-Chloro-4-iodo-phenyl)-2-{(R)-4-[4-((R)-2,3-dihydroxy-propoxy)-phenyl]-2,5-dioxo-imidazolidin-1-yl}-3-phenyl-butyramide;

(2S,3S)—N-(2-Chloro-4-iodo-phenyl)-2-{(R)-4-[4-((S)-2,3-dihydroxy-propoxy)-phenyl]-2,5-dioxo-imidazolidin-1-yl}-3-phenyl-butyramide;

(2S,3S)-2-{(R)-2,5-Dioxo-4-[4-(2-oxo-2-pyrrolidin-1-yl-ethoxy)-phenyl]-imidazolidin-1-yl}-N-(2-fluoro-4-iodo-phenyl)-3-phenyl-butyramide;

(2S,3S)-2-((R)-2,5-Dioxo-4-thiophen-3-yl-imidazolidin-1-yl)-N-(4-iodo-phenyl)-3-phenyl-butyramide;

(S)-2-[(R)-4-(2,3-Dihydro-benzo[1,4]dioxin-6-yl)-2,5-dioxo-imidazolidin-1-yl]-N-(2-fluoro-4-iodo-phenyl)-3-phenyl-propionamide;

(S)-2-[(R)-4-(4-Acetylamino-phenyl)-2,5-dioxo-imidazolidin-1-yl]-N-(2-fluoro-4-iodo-phenyl)-3-phenyl-propionamide;

(4-{(R)-1-[(1S,2S)-1-(2-Fluoro-4-iodo-phenylcarbamoyl)-2-phenyl-propyl]-2,5-dioxo-imidazolidin-4-yl}-phenoxymethyl)-phosphonic acid dimethyl ester;

(2S,3S)—N-(2-Fluoro-4-iodo-phenyl)-2-((R)-4-isopropyl-2,5-dioxo-imidazolidin-1-yl)-3-phenyl-butyramide;

(S)—N-(2-Fluoro-4-iodo-phenyl)-2-{(R)-4-[4-(2-hydroxy-ethoxy)-phenyl]-2,5-dioxo-imidazolidin-1-yl}-3-methyl-butyramide;

(S)—N-(2-Fluoro-4-iodo-phenyl)-2-[(R)-4-(4-methoxy-phenyl)-2,5-dioxo-imidazolidin-1-yl]-3-o-tolyl-propionamide;

(S)—N-(2-Fluoro-4-iodo-phenyl)-2-[(R)-4-(4-methoxy-phenyl)-2,5-dioxo-imidazolidin-1-yl]-3-m-tolyl-propionamide;

(S)—N-(2-Fluoro-4-iodo-phenyl)-2-[(R)-4-(4-methoxy-phenyl)-2,5-dioxo-imidazolidin-1-yl]-3-p-tolyl-propionamide; and (S)—N-(4-Cyclopropyl-2-fluoro-phenyl)-3-(4-fluoro-phenyl)-2-{(R)-4-[4-(2-hydroxy-1-hydroxymethyl-ethoxy)-phenyl]-2,5-dioxo-imidazolidin-1-yl}-propionamide.

13. A compound selected from the group consisting of:
(2S,3S)—N-(2-Fluoro-4-iodo-phenyl)-2-{(R)-4-[4-(2-hydroxy-ethoxy)-phenyl]-2,5-dioxo-imidazolidin-1-yl}-3-phenyl-butyramide;

(2S,3S)-2-{(R)-4-[4-((R)-2,3-dihydroxy-propoxy)-phenyl]-2,5-dioxo-imidazolidin-1-yl}-N-(2-fluoro-4-iodo-phenyl)-3-phenyl-butyramide;

(2S,3S)—N-(2-Chloro-4-iodo-phenyl)-2-{(R)-4-[4-((R)-2,3-dihydroxy-propoxy)-phenyl]-2,5-dioxo-imidazolidin-1-yl}-3-phenyl-butyramide;

(2S,3S)—N-(2-Chloro-4-iodo-phenyl)-2-{(R)-4-[4-((S)-2,3-dihydroxy-propoxy)-phenyl]-2,5-dioxo-imidazolidin-1-yl}-3-phenyl-butyramide; and (2S,3S)—N-(4-Cyclopropyl-2-fluoro-phenyl)-2-{(R)-4-[4-(2-hydroxy-ethoxy)-phenyl]-2,5-dioxo-imidazolidin-1-yl}-3-phenyl-butyramide.

14. A pharmaceutical composition comprising a compound of claim 1 and a pharmaceutically acceptable diluent, excipient, or adjuvant.

15. A pharmaceutical composition comprising a compound of claim 11 and a pharmaceutically acceptable diluent, excipient, or adjuvant.

16. A pharmaceutical composition comprising a compound of claim 13 and a pharmaceutically acceptable diluent, excipient, or adjuvant.

* * * * *